US010450326B2

(12) United States Patent
Wang et al.

(10) Patent No.: US 10,450,326 B2
(45) Date of Patent: Oct. 22, 2019

(54) THIAZOLOPYRIMIDINONE COMPOUNDS AND PREPARATION METHODS AND USE THEREOF

(71) Applicant: PEKING UNIVERSITY, Beijing (CN)

(72) Inventors: Kewei Wang, Beijing (CN); Qi Sun, Beijing (CN); Wenxuan Jiao, Beijing (CN); Jingshu Tang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 15/577,725

(22) PCT Filed: Jun. 3, 2016

(86) PCT No.: PCT/CN2016/084691
§ 371 (c)(1),
(2) Date: Nov. 29, 2017

(87) PCT Pub. No.: WO2016/192667
PCT Pub. Date: Dec. 8, 2016

(65) Prior Publication Data
US 2018/0155366 A1    Jun. 7, 2018

(30) Foreign Application Priority Data

Jun. 3, 2015  (CN) .......................... 2015 1 0299946

(51) Int. Cl.
| | |
|---|---|
| *A61K 31/429* | (2006.01) |
| *C07D 513/04* | (2006.01) |
| *A61P 25/28* | (2006.01) |
| *A61P 25/00* | (2006.01) |
| *A61P 25/16* | (2006.01) |

(52) U.S. Cl.
CPC ............ *C07D 513/04* (2013.01); *A61P 25/00* (2018.01); *A61P 25/16* (2018.01); *A61P 25/28* (2018.01)

(58) Field of Classification Search
CPC ........................... A61K 31/429; C07D 513/04
USPC ...................... 514/243, 260.1; 544/184, 255
See application file for complete search history.

(56) References Cited

U.S. PATENT DOCUMENTS

| | | | | |
|---|---|---|---|---|
| 6,806,273 | B1 * | 10/2004 | Austin ................. | C07D 513/04 514/260.1 |
| 8,921,361 | B2 * | 12/2014 | Cmiljanovic ........ | C07D 251/18 514/232.2 |
| 2007/0135454 | A1 * | 6/2007 | Bayliss ................ | C07D 471/04 514/260.1 |
| 2014/0171408 | A1 * | 6/2014 | Blench ................. | C07D 513/04 514/210.21 |

FOREIGN PATENT DOCUMENTS

| | | |
|---|---|---|
| CN | 102666540 A | 9/2012 |
| DE | 208355 A1 | 5/1984 |
| WO | 2008/092861 A1 | 8/2008 |
| WO | WO 2008/092861 * | 8/2008 |
| WO | 2011/045258 A1 | 4/2011 |

OTHER PUBLICATIONS

Gewald et al., 4-Amino-Thiazole, Journal fuer Praktische Chemie, vol. 35, No. 1-2, pp. 97-104 (Year: 1967).*
Sekiya et al., Reaction of 2-(Acylamino)Thioacetamides, Leading to 5-Aminothiazoles and to Thiazolo[5,4-d]pyrimidines, Chemical & Pharmaceutical Bulletin, vol. 13, No. 11, pp. 1319-1325 (Year: 1965).*
Ahluwalia, V.K., et al., One-step synthesis of thiazolo[4,5-d]pyrimidines. Indian Journal of Chemistry, Sect. B: Organic Chemistry Including Medicinal Chemistry, Dec. 31, 1989;28(11):964-5.
Chande, M.S., et al., Synthesis of pyrazolothiazole and pyrimidinothiazole derivatives. Indian Journal of Chemistry. Sect. B: Organic Chemistry Including Medical Chemistry, 1995;34(11):985-9.
International Search Report for Application No. PCT/CN2016/084691, dated Sep. 8, 2016 (8 pages).
Lin, R.H., et al., Synthesis and evaluation of 2,7-diamino-thiazolo[4,5-d] pyrimidine analogues as anti-tumor epidermal growth factor receptor (EGFR) tyrosine kinase inhibitors. Bioorg Med Chem Lett. Apr. 15, 2009;19(8):2333-7. doi: 10.1016/j.bmcl.2009.02.067. Epub Feb. 21, 2009.
Prickaerts, J., et al., EVP-6124, a novel and selective α7 nicotinic acetylcholine receptor partial agonist, improves memory performance by potentiating the acetylcholine response of α7 nicotinic acetylcholine receptors. Neuropharmacology. Feb. 2012;62(2):1099-110. doi: 10.1016/j.neuropharm.2011.10.024. Epub Nov. 10, 2011.
Schmalhofer, W.A., et al., A pharmacologically validated, high-capacity, functional thallium flux assay for the human Ether-à-go-go related gene potassium channel. Assay Drug Dev Technol. Dec. 2010;8(6):714-26. doi: 10.1089/adt.2010.0351.
Wallace, T.L., et al., RG3487, a novel nicotinic α7 receptor partial agonist, improves cognition and sensorimotor gating in rodents. J Pharmacol Exp Ther. Jan. 2011;336(1):242-53. doi: 10.1124/jpet.110.171892. Epub Oct. 19, 2010.
Wobig, D., [Thiazolderivate, VI. Darstellung von Thiazolo[4,5-d]v-triazin-7(6H)-onen.] Thiazole Derivatives, VI. Synthesis of thiazolo[4,5-d]-v-triazin-7(6H)-ones. Liebigs Annalen der Chemie, Dec. 31, 1984;12:1994-7. German language document. English abstract only.
Wobig, D., [Thiazolderivate, VII. Darstellung von Thiazolo[4,5-d]pyrimidin-Derivaten.] Thiazole Derivatives, VII. Synthesis of thiazolo[4,5-d]pyrimidine derivatives. Liebigs Annalen der Chemie, Dec. 31, 1989;12:409-11. German anguage document. English abstract only.
Dineley KT, Pandya AA, Yakel JL. Nicotinic ACh receptors as therapeutic targets in CNS disorders. Trends Pharmacol Sci. 2015; 36: 96-108.

(Continued)

*Primary Examiner* — Brenda L Coleman
(74) *Attorney, Agent, or Firm* — Nutter McClennen & Fish LLP

(57) ABSTRACT

The present invention provides structural details of a thiazolopyrimidinone compound, a preparation method thereof, and use thereof in the manufacture of a medicament for the treatment of central nervous system diseases.

5 Claims, 3 Drawing Sheets

(56) References Cited

OTHER PUBLICATIONS

Freedman R. alpha7-nicotinic acetylcholine receptor agonists for cognitive enhancement in schizophrenia. Annu Rev Med. 2014; 65: 245-261.
Gewald, K., et al., "4-Amino-thiazole," Journal fur Praktische Chemie, 1967, v. 35, issue 1-2, p. 104 (abstract with machine translation).
Gotti C, Zoli M, Clementi F. Brain nicotinic acetylcholine receptors: native subtypes and their relevance. Trends Pharmacol Sci. 2006; 27:482-491.
Sekiya, M., et al., Azole Series. I. Reaction of 2-(Acylamino)thioacetamides, leading to 5-Aminothiazoles and to Thiazolo[5,4-d]pyrimidines, Chem Pharm Bull, 1965, v. 13, pp. 1319-1325.
Taly A, Conringer PJ, Guedin D, Lestage P, Changeux JP. Nicotinic receptors: allosteric transitions and therapeutic targets in the nervous system. Nat Rev Drug Discov. 2009; 8: 733-750.
Wonnacott S. Presynaptic nicotinic ACh receptors. Trends Neurosci. 1997; 20: 92-98.
Yang T, Xiao T, Sun Q, Wang K, The current agonists and positive allosteric modulators of alpha7 nAChR for CNS indications in clinical trials. Acta Pharm Sin B. 2017; 7:611-622].

\* cited by examiner

THIAZOLOPYRIMIDINONE COMPOUNDS AND PREPARATION METHODS AND USE THEREOF

FIELD OF THE INVENTION

The present invention relates to thiazolopyrimidinone compounds, their preparation methods, and their uses in the manufacture of medicaments for the treatment of central nervous system diseases.

BACKGROUND

Senile Dementia, also known as Alzheimer's disease, is a progressive and lethal neurodegenerative disease. The clinical manifestations of patients are the deteriorated cognitive and memory function, the progressive decline of living ability, and a variety of neuropsychiatric symptoms and behavioral disorders. Many studies have clearly shown that lack of acetylcholine and decreased expression of nicotinic acetylcholine receptors (nAChRs) are common in patient's brain.

According to the literature, α7 nicotinic acetylcholine receptor positive allosteric modulator (PAM) has an effect of increasing the ability of learning and memory. Experiments show that compared to the control group of mice having α7nAChR subunit, mice lacking α7nAChR subunit have lower learning and memory ability in the water maze test. α7nAChR PAMs function differently from agonists, with less possibility of causing desensitization, and the potential side effects will be greatly reduced. By regulating the pathway of α7 nicotinic acetylcholine receptors, we hope to find a new type of therapy for the treatment of a series of central nervous system diseases such as Alzheimer's disease and Parkinson's disease.

SUMMARY

Accordingly, an object of the present invention is to provide a pharmaceutically active ingredient for the treatment of a series of central nervous system diseases such as Alzheimer's disease and Parkinson's disease.

The present inventors have developed a variety of one-pot tandem reaction and metal-catalyzed desulfurization coupling reaction, and have used these reactions to synthesize nearly a hundred compounds of various structures. In vitro activity screening showed that a number of compounds had certain agonistic or antagonistic activities against α7 nicotinic acetylcholine receptors, in which the compound numbered LD486 is a novel thiazolopyrimidinone compound. The results showed that the compound was of strong activity as an α7nAChRPAM, with the Ki value being about 3 μM, and the dose-effect relationship between activity and concentration was obvious, its selectivity was high with no effect on other subtypes, it had no effect on the hERG ion channel expressed by CHO cells and the risk of cardiotoxicity was low.

Accordingly, the present invention provides a thiazolopyrimidinone compound having a structure represented by Formula (I):

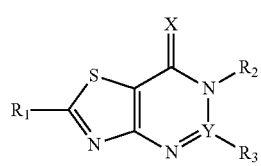

Formula (I)

wherein, X=O or S, Y=C or N, when Y=C, R3 is selected from the group consisting of H, C1-C12 hydrocarbonyl, phenyl, phenyl substituted by one or more of halogen, hydroxyl, carboxyl, an ester group, C1-C4 alkyl and C1-C4 alkoxy, and five or six membered heterocyclyl;

R2 is selected from the group consisting of H, C1-C12 hydrocarbonyl, C1-C6 alkoxy, C1-C6 alkylthio, C1-C6 alkylamino, phenyl, phenyl substituted by one or more of halogen, hydroxyl, carboxyl, an ester group, C1-C4 alkyl and C1-C4 alkoxy, benzyl, benzyl substituted by one or more of halogen, hydroxyl, carboxyl, an ester group, C1-C4 alkyl and C1-C4 alkoxy, five or six membered heterocyclyl, and five or six membered heterocyclyl substituted by one or more of halogen, hydroxyl, carboxyl, an ester group, C1-C4 alkyl and C1-C4 alkoxy;

$R_1$ is selected from the group consisting of H, C1-C6 alkyl, C1-C6 alkoxy, C1-C6 alkylthio, C1-C6 alkylamino, phenyl, phenyl substituted by one or more of halogen, an ester group, carboxyl, C1-C4 alkyl and C1-C4 alkoxy, phenylthio, phenylthio substituted by one or more of halogen, an ester group, carboxyl, C1-C4 alkyl and C1-C4 alkoxy, benzylthio, benzylthio substituted by one or more of halogen, an ester group, carboxyl, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, and arylcarboxamido substituted by one or more of halogen, C1-C4 alkyl, C1-C4 alkoxy, five or six membered heterocyclyl and five or six membered heterocyclyl substituted by C1-C4 alkyl or hydroxyl.

Preferably, in Formula (I) of the thiazolopyrimidinone compound provided by the present invention, X=O, Y=C, $R_1$ is selected from the group consisting of C1-C6 alkylthio, C1-C6 alkylamino, phenyl, phenyl substituted by one or more of halogen, an ester group, carboxyl, C1-C4 alkyl and C1-C4 alkoxy, phenylthio, phenylthio substituted by one or more of halogen, an ester group, carboxyl, C1-C4 alkyl and C1-C4 alkoxy, benzylthio, benzylthio substituted by one or more of halogen, an ester group, carboxyl, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, arylcarboxamido substituted by one or more of halogen, C1-C4 alkyl, C1-C4 alkoxy, five or six membered heterocyclyl and five or six membered heterocyclyl substituted by C1-C4 alkyl or hydroxyl; $R_2$ is selected from phenyl substituted by one or more of halogen, hydroxyl, carboxyl, an ester group, C1-C4 alkyl and C1-C4 alkoxy; $R_3$=H.

The present invention also provides the preparation method of a compound represented by Formula (I), which comprises:

(1) reacting chloroacetyl chloride with $R_2$—$NH_2$, to give a compound II;

(2) reacting compound II with dipotassium cyanodithiomidocarbonate as well as iodomethane, iodoethane, halogenated C1-C6 alkyl, halogenated C1-C6 alkylamine, phenyl substituted by one or more of halogen, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, or benzyl halide substituted by one or more of halogen, an ester group, carboxyl, C1-C4 alkyl and C1-C4 alkoxy, to give a compound III (2-alkylthio-4-amino-thiazole-5-carboxamide);

(3) reacting compound III with formic acid or NaNO₂, to give a compound IV (2-(alkylthio)thiazolo[4,5-d]pyrimidin-7 (6H)-one or 6-(alkylthio)thiazolo[4,5-d][1,2,3]triazin-4(3H)-one), which is a ring closure product;

when R1 is C1-C6 alkylthio or benzylthio substituted by one or more of halogen, an ester group, carboxyl, C1-C4 alkyl and C1-C4 alkoxy, compound IV described above is represented by Formula (I); or when R1 is C1-C6 alkylamino, phenyl, phenyl substituted by one or more of halogen, an ester group, carboxyl, C1-C4 alkyl and C1-C4 alkoxy, phenylthio, phenylthio substituted by one or more of halogen, an ester group, carboxyl, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, arylcarboxamido substituted by one or more of halogen, C1-C4 alkyl, C1-C4 alkoxy, five or six membered heterocyclyl and five or six membered heterocyclyl substituted by C1-C4 alkyl or hydroxyl, compound IV is subjected to step (4), or compound IV is transformed to a compound V (2-(alkylsulfonyl)thiazolo[4,5-d]pyrimidin-7 (6H)-one or 6-(alkylsufonyl)thiazolo[4,5-d][1,2,3]triazin-4-(3H)-one) under the action of an oxidizing agent and then subjected to step (4);

(4) reacting compound IV or V with C1-C6 alkylamine, phenylboronic acid, phenylboronic acid substituted by one or more of halogen, an ester group, carboxyl, C1-C4 alkyl and C1-C4 alkoxy, thiophenol, thiophenol substituted by one or more of halogen, an ester group, carboxyl, C1-C4 alkyl and C1-C4 alkoxy, arylamine, arylamine substituted by one or more of halogen, C1-C4 alkyl, C1-C4 alkoxy, five or six membered heterocyclyl and five or six membered heterocyclyl substituted by C1-C4 alkyl or hydroxyl, arylcarboxamide, arylcarboxamide substituted by one or more of halogen, C1-C4 alkyl, C1-C4 alkoxy, five or six membered heterocyclyl and five or six membered heterocyclyl substituted by C1-C4 alkyl or hydroxyl, to give a compound represented by Formula (I);

wherein, R1' in compound III, IV and V is selected from the group consisting of C1-C6 alkyl, phenyl, phenyl substituted by one or more of halogen, an ester group, carboxyl, C1-C4 alkyl and C1-C4 alkoxy, benzyl, benzyl substituted by one or more of halogen, an ester group, carboxyl, C1-C4 alkyl and C1-C4 alkoxy, five or six membered heterocyclyl and five or six membered heterocyclyl substituted by one or more of halogen, hydroxyl, carboxyl, an ester group, C1-C4 alkyl and C1-C4 alkoxy.

(II)

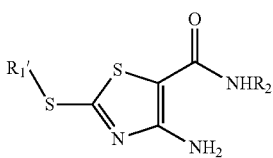

(III)

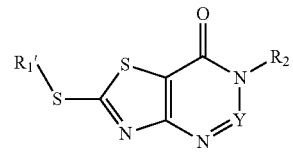

(IV)

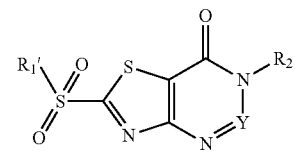

(V)

In particular, for different compounds of Formula (I), the preparation method may be any one of the following four synthetic routes.

Synthetic Route 1:

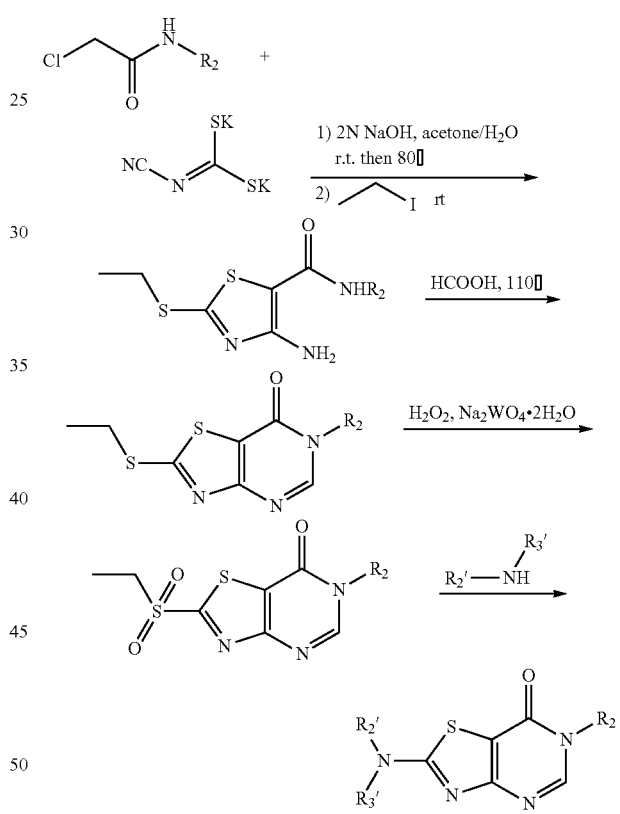

Wherein, the substituent

represents C1-C6 alkylamino, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, arylcarboxamido substituted by one or more of halogen, C1-C4 alkyl, C1-C4 alkoxy, five or six membered heterocyclyl and five or six membered heterocyclyl substituted by C1-C4 alkyl or hydroxyl, or —NH—R$_2$.

Synthetic Route 2:

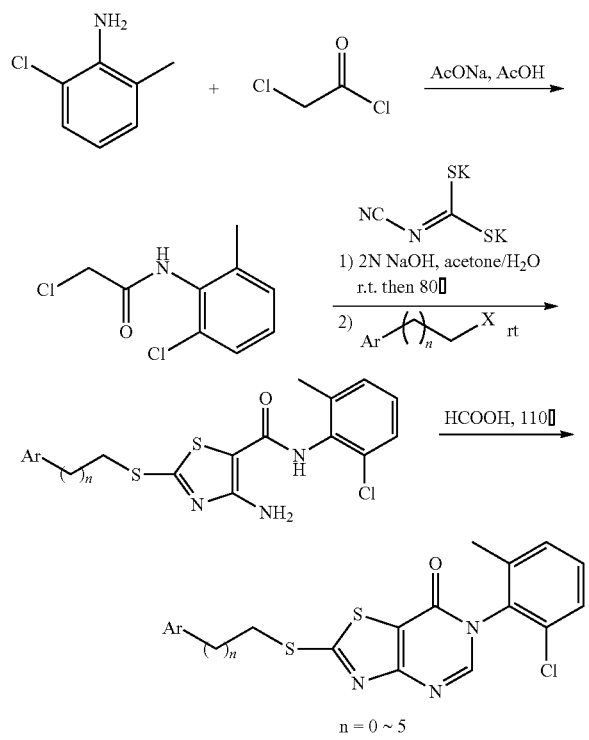

Synthetic Route 3:

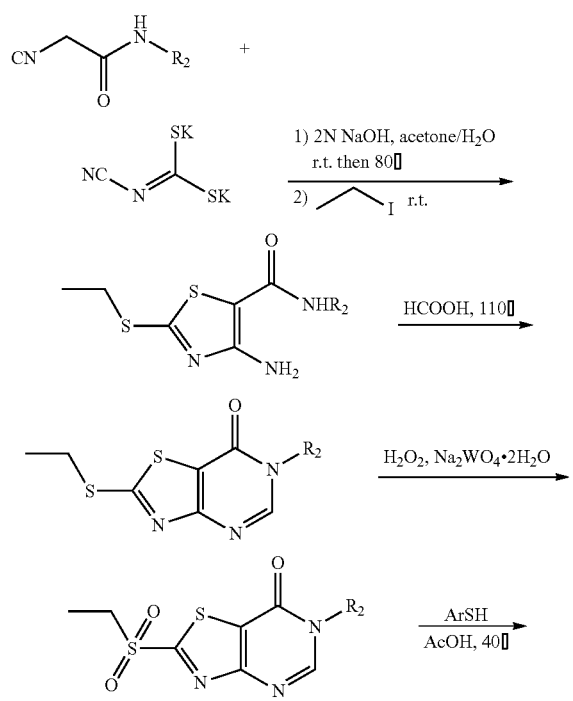

Synthetic Route 4:

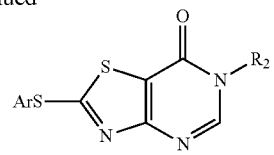

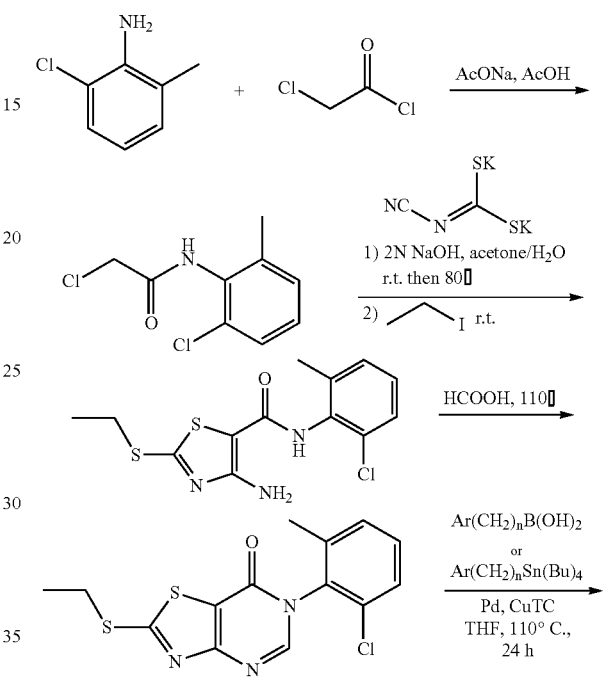

The present invention also provides use of a thiazolopyrimidinone compound of Formula (I) in the manufacture of a medicament for the treatment of central nervous system diseases.

The present invention also provides a method for treating central nervous system diseases, comprising administering to a subject in need thereof a thiazolopyrimidinone compound represented by the Formula (I) of the present invention.

The present invention also provides a thiazolopyrimidinone compound represented by Formula (I) for the treatment of central nervous system diseases.

The present invention also provides the use of a thiazolopyrimidinone compound represented by Formula (I) of the present invention in the preparation of a positive allosteric modulator of α7 nicotinic acetylcholine receptor.

The present invention also provides a thiazolopyrimidinone compound represented by Formula (I) of the present invention as a postive allosteric modulator of the α7 nicotinic acetylcholine receptor.

The thiazolopyrimidinones of the present invention has the following beneficial effects: the activity as an α7 nicotinic acetylcholine receptor positive allosteric modulator is strong, with the $EC_{50}$ value being 0.1 to 100 μM, and the dose-effect relationship between activity and concentration is obvious; its selectivity is high with no effect on other subtypes, it has no effect on the hERG ion channel expressed by CHO cells and the risk of cardiotoxicity is low.

BRIEF DESCRIPTION OF THE DRAWINGS

Hereinafter, embodiments of the present invention will be described in detail with reference to the accompanying drawings, in which.

DETAILED DESCRIPTION

Figure 1:
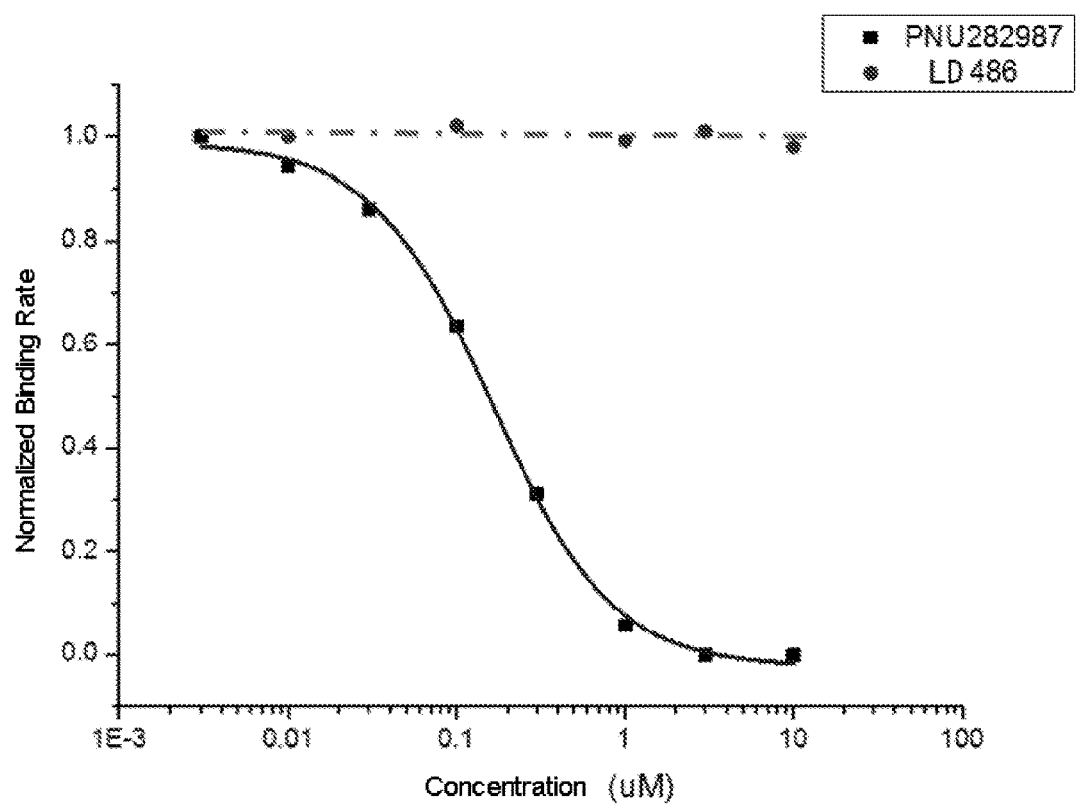
FIG. 1 is a rate curve for which endogenous ligand antagonist PNU-282987 or LD486 with a gradual increase in the concentration replace the [$^3$H]-Methyllycaconitine radioligand that bound to rat brain cell membrane.

The invention will be described in further detail below with reference to specific embodiments thereof, the examples are given for the purpose of illustrating the invention and not intended to limit the scope of the invention.

Example 1: Preparation of 6-(2-Chloro-6-methylphenyl)-2-(phenylamino)thiazolo[4,5-d]pyrimidin-7(6H)-one (JWX-A0824)

1. Synthesis of 2-chloro-N-(2-chloro-6-methylphenyl)acetamide (A2)

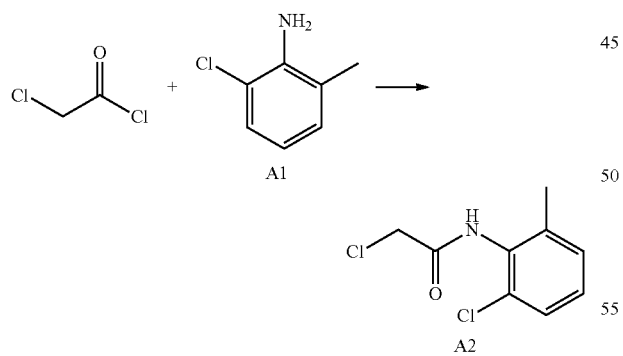

Compound A1 (14.2 g, 100 mmol) was dissolved in acetic acid (100 mL) and saturated aqueous solution of sodium acetate (80 mL). Chloroacetyl chloride (17.0 g, 150 mmol) was added dropwise under ice-bath and turbidity quickly appeared. The reaction mixture was slowly warmed to room temperature and stirred overnight. Water (100 mL) was added, the precipitated solid was filtered by vacuum, washed with water and dried to obtain compound A2 as a white solid. Yield: 12.7 g, 58.0%. The crude product was used in the next step without purification.

2. Synthesis of 4-Amino-N-(2-chloro-6-methylphenyl)-2-(ethylthio)thiazole-5-carboxamide (A3)

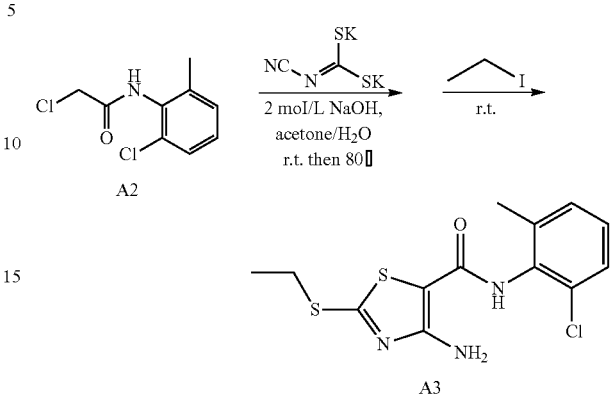

Compound A2 (10.90 g, 50 mmol) was dissolved in acetone (100 mL). Then, the solution of dipotassium cyanodithiomidocarbonate (9.70 g, 50 mmol) in water (100 mL) was added to the system and 2 mol/L NaOH aqueous solution (25 mL) was added to the solution. The reaction mixture was stirred for 2 h at room temperature, then heated to 80° C. for 0.5 h. Afterward, the reaction mixture was cooled to room temperature. To the mixture Iodoethane (7.80 g, 50 mmol) was added dropwise and a large quantity of yellow solid appeared. After reaction for 1 h at room temperature, the reaction mixture was poured into ice water, the precipitated solid was filtered by vacuum, washed with water and dried to obtain compound A3 as a yellow solid. Yield: 13.3 g, 81%.

3. Synthesis of 6-(2-Chloro-6-methylphenyl)-2-(ethylsulfonyl)thiazolo[4,5-d]pyrimidin-7(6H)-one (A5)

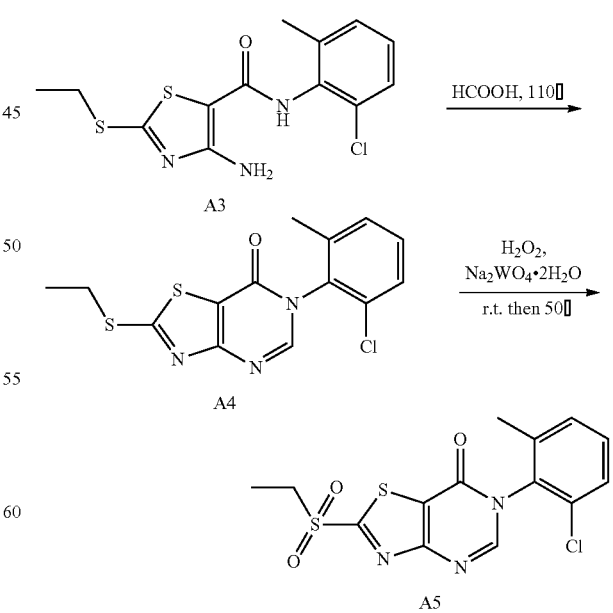

Compound A3 (6.60 g, 20 mmol) was dissolved in HCOOH (15 mL). The reaction was held at reflux for 1 h, then cooled to room temperature. Water (100 mL) was added, and the reaction mixture was extracted with ethyl acetate (20 mL×5), concentrated to dryness on a rotary evaporator to afford A4. Ethanol (100 mL) was added, and Na$_2$WO$_4$.2H$_2$O (1.00 g, 3 mmol) was added. To the mixture 30% hydrogen peroxide solution (20 mL) was added slowly, and the reaction mixture was reacted for 1 h at room temperature, then heated to 50° C. for 1 h. Afterward, water (100 mL) was added, the precipitated solid was filtered by vacuum, washed with water and dried to obtain compound A5 as a white solid. Yield: 3.98 g, 54.0%.

4. Synthesis of 6-(2-Chloro-6-methylphenyl)-2-(phenylamino)thiazolo[4,5-d]pyrimidin-7(6H)-one (JWX-A0824)

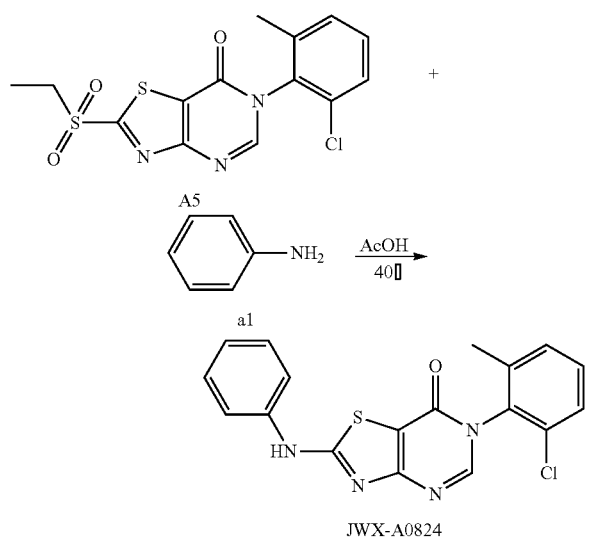

Compound A5 (370 mg, 1.0 mmol) was dissolved in acetic acid (7 mL). Then, aniline (189 mg, 2.0 mmol) was added to the solution. The reaction was held at 40° C. overnight. Afterward, water was added, the precipitated solid was filtered by vacuum, washed with water and dried to obtain JWX-A0824 as a white solid. Yield: 0.155 g, 42%, m.p.: 150-153° C.

$^1$H-NMR (400 MHz, CDCl$_3$) δ 10.42 (s, 1H), 8.04-6.91 (m, 9H), 2.13 (s, 3H). $^{13}$C-NMR (101 MHz, CDCl$_3$) δ 170.7, 166.1, 155.7, 149.2, 139.1, 138.7, 133.7, 132.9, 130.9, 129.7, 129.5, 128.1, 125.0, 120.5, 108.6, 18.4. HRMS: m/z calcd. for C$_{18}$H$_{14}$ClN$_4$OS [M+H]$^+$ 369.0571; found 369.0573.

Example 2: Preparation of 2-((6-Chloro-2-methyl-pyrimidin-4-yl) amino)-6-(2-chloro-6-methylphenyl) thiazolo[4,5-d]pyrimidin-7(6H)-one (LD486)

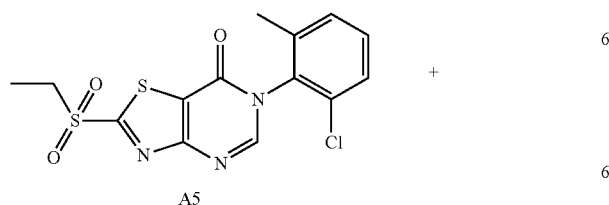

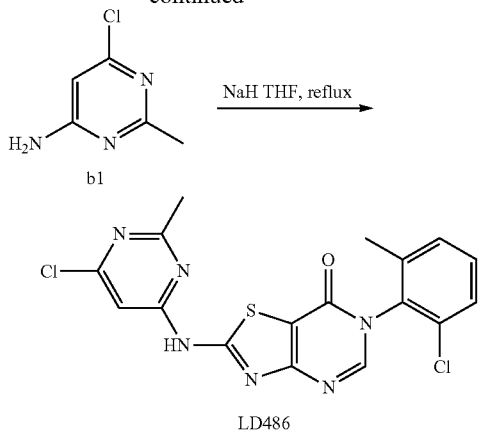

Compound A5 (370 mg, 1.0 mmol) and 2-methyl-4-amino-6-chloropyrimidine (287 mg, 2.0 mmol) were dissolved in anhydrous THF (3 mL). Then, NaH (48 mg, 2.0 mmol) was added to the solution, dry condenser tube was equipped with a balloon on the top. The reaction was held at reflux for 0.5 h, then the reaction was stopped and cooled to room temperature, the reaction mixture was poured into ice water, the pH was adjusted to neutral by adding dilute hydrochloric acid dropwise, a large amount of solid was precipitated out. The precipitated solid was filtered by vacuum, washed with water and dried to obtain LD486 as a yellow solid. Yield: 398 mg, 95.0%. The solid was recrystallized in ethanol, m.p.: 315-317° C.

$^1$H-NMR (400 MHz, DMSO-d$_6$) δ 8.44 (s, 1H), 7.65-7.40 (m, 3H), 6.99 (s, 1H), 2.56 (s, 3H), 2.15 (s, 3H). $^{13}$C-NMR (101 MHz, DMSO-d$_6$) δ 167.8, 164.0, 159.5, 158.1, 155.9, 150.9, 139.1, 134.0, 132.3, 131.4, 130.3, 128.1, 112.0, 104.6, 25.5, 18.2. HRMS: m/z calcd. for C$_{17}$H$_{13}$Cl$_2$N$_6$OS [M+H]$^+$ 419.0243; found 419.0243.

Example 3: Preparation of 6-(2-Chloro-6-methyl-phenyl)-2-(p-tolylamino)thiazolo[4,5-d]pyrimidin-7(6H)-one (JWX-A1029)

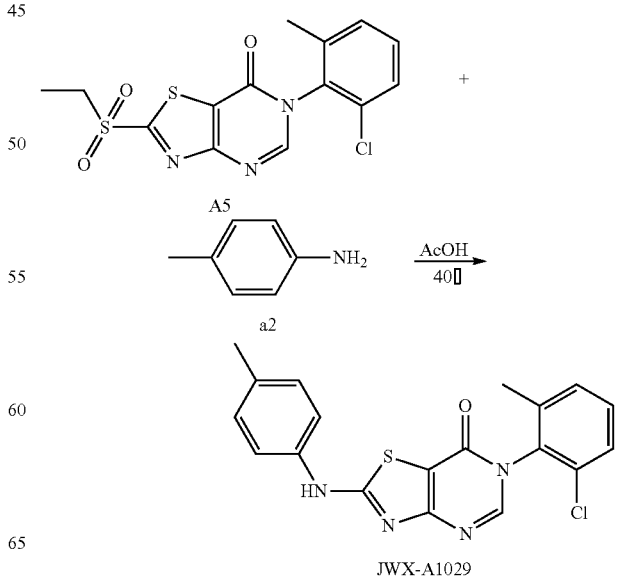

The title compound was prepared following the general procedure of compound JWX-A0824. JWX-A1029 was obtained as a white solid. Yield: 88%, m.p.: 241-246° C.

¹H-NMR (400 MHz, CDCl₃) δ 10.08 (s, 1H), 7.81 (s, 1H), 7.45 (d, J=8.3 Hz, 2H), 7.33 (d, J=7.8 Hz, 1H), 7.26 (t, J=7.8 Hz, 1H), 7.19 (d, J=9.8 Hz, 1H), 7.12 (d, J=8.2 Hz, 2H), 2.27 (s, 3H), 2.13 (s, 3H). ¹³C-NMR (101 MHz, CDCl₃) δ 171.41, 165.98, 155.47, 149.13, 138.64, 136.39, 135.17, 133.73, 132.90, 130.77, 130.08, 129.59, 128.03, 121.07, 108.21, 21.02, 18.35.

Example 4: Preparation of 6-(2-Chloro-6-methylphenyl)-2-((4-methoxyphenyl)amino)thiazolo[4,5-d]pyrimidin-7(6H)-one (JWX-A1030)

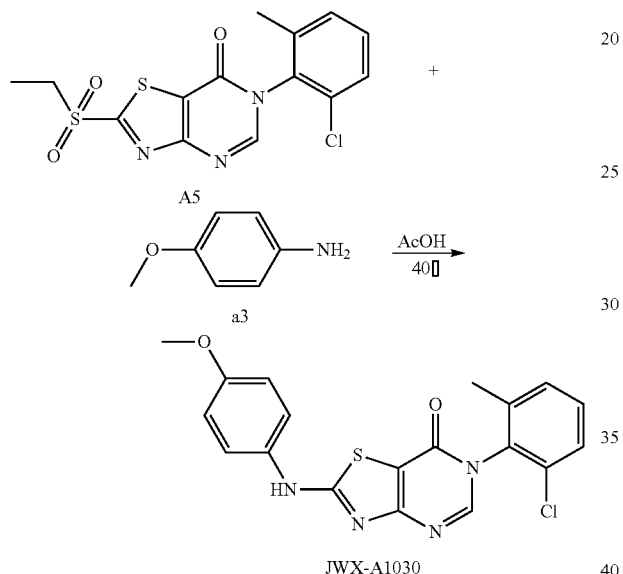

The title compound was prepared following the general procedure of JWX-A0824. JWX-A1030 was obtained as an off-white solid. Yield: 75%. m.p.: 214-218° C.

¹H-NMR (400 MHz, CDCl₃) δ 10.21 (s, 1H), 7.90 (s, 1H), 7.58 (d, J=8.9 Hz, 2H), 7.46-7.25 (m, 3H), 6.96 (d, J=8.9 Hz, 2H), 3.85 (s, 3H), 2.23 (s, 3H). ¹³C-NMR (101 MHz, CDCl₃) δ 172.46, 166.09, 157.67, 155.39, 149.16, 138.64, 133.75, 132.90, 131.86, 130.73, 129.57, 128.01, 123.67, 114.82, 108.10, 55.55, 18.33.

Example 5: Preparation of 6-(2-Chloro-6-methylphenyl)-2-((4-chlorophenyl)amino)thiazolo[4,5-d]pyrimidin-7(6H)-one (JWX-A1104)

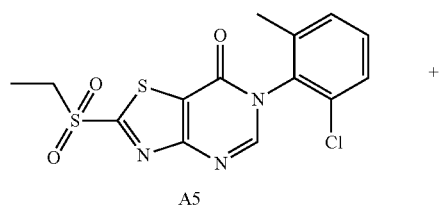

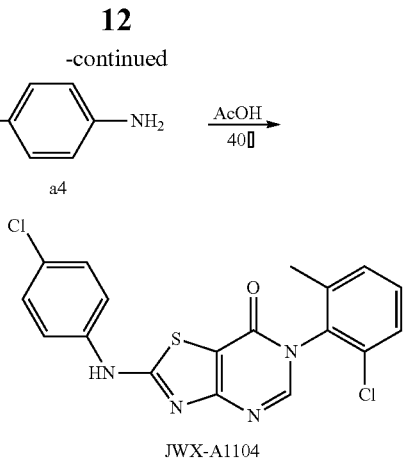

The title compound was prepared following the general procedure of JWX-0824. JWX-A1104 was obtained as a white solid. Yield: 94%. m.p.: 258-264° C.

¹H-NMR (400 MHz, DMSO-d₆) δ 11.28 (s, 1H), 8.40 (s, 1H), 7.78 (d, J=8.7 Hz, 2H), 7.62-7.33 (m, 5H), 2.13 (s, 3H). ¹³C-NMR (101 MHz, DMSO-d₆) δ 167.46, 166.29, 155.15, 150.81, 139.08, 138.92, 133.98, 132.28, 131.40, 130.21, 129.55, 128.05, 127.41, 120.56, 108.67, 18.16.

Example 6: Preparation of 6-(2-chloro-6-methylphenyl)-2-((4-Bromophenyl)amino)-thiazolo[4,5-d]pyrimidin-7(6H)-one (JWX-A1105)

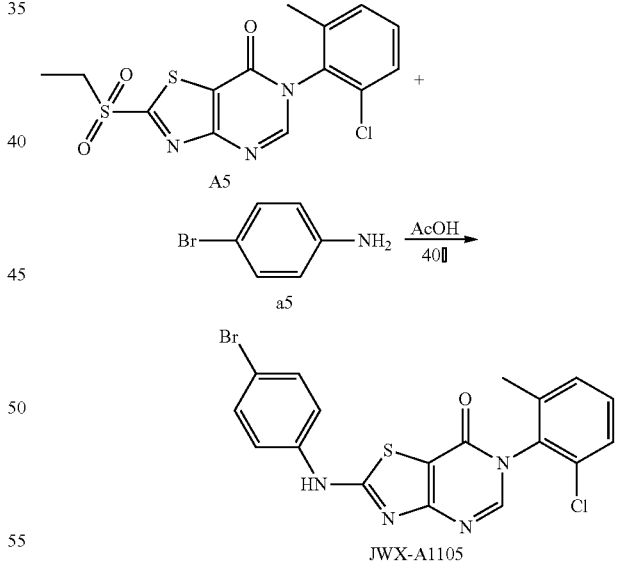

The title compound was prepared following the general procedure of JWX-A0824. JWX-A1105 was obtained as a white solid. Yield: 82.7% m.p.: 281-286° C.

¹H-NMR (400 MHz, DMSO-d₆) δ 11.28 (s, 1H), 8.40 (s, 1H), 7.73 (d, J=8.5 Hz, 2H), 7.51 (ddd, J=19.5, 15.6, 8.0 Hz, 5H), 2.13 (s, 3H). ¹³C-NMR (101 MHz, DMSO-d₆) δ 167.40, 166.28, 155.15, 150.83, 139.33, 139.08, 133.97, 132.45, 132.28, 131.41, 130.22, 128.05, 120.91, 115.37, 108.70, 18.17.

Example 7: Preparation of 6-(2-chloro-6-methylphenyl)-2-((3-methoxyphenyl)amino)thiazolo[4,5-d]pyrimidin-7(6H)-one (JWX-A1106)

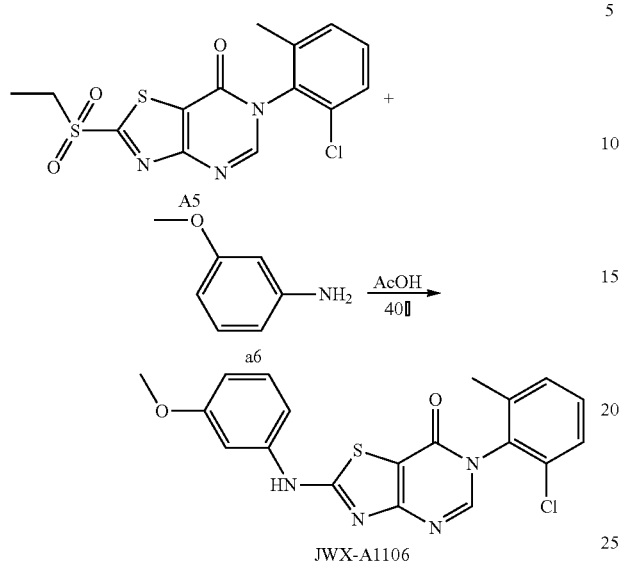

The title compound was prepared following the general procedure of JWX-A0824. JWX-A1106 was obtained as a reddish brown solid. Yield: 85.5%. m.p.: 194-197° C.

¹H-NMR (400 MHz, DMSO-d$_6$) δ 11.16 (s, 1H), 8.39 (s, 1H), 7.68-7.13 (m, 6H), 6.71 (d, J=6.6 Hz, 1H), 3.78 (s, 3H), 2.13 (s, 3H). ¹³C-NMR (101 MHz, DMSO-d$_6$) δ 167.74, 166.39, 160.39, 155.15, 150.75, 141.06, 139.09, 134.02, 132.31, 131.37, 130.52, 130.19, 128.04, 111.50, 109.19, 108.36, 105.25, 55.60, 18.17.

Example 8: Preparation of 6-(2-chloro-6-methylphenyl)-2-((3-Bromophenyl)amino)-thiazolo[4,5-d]pyrimidin-7(6H)-one (JWX-A1113)

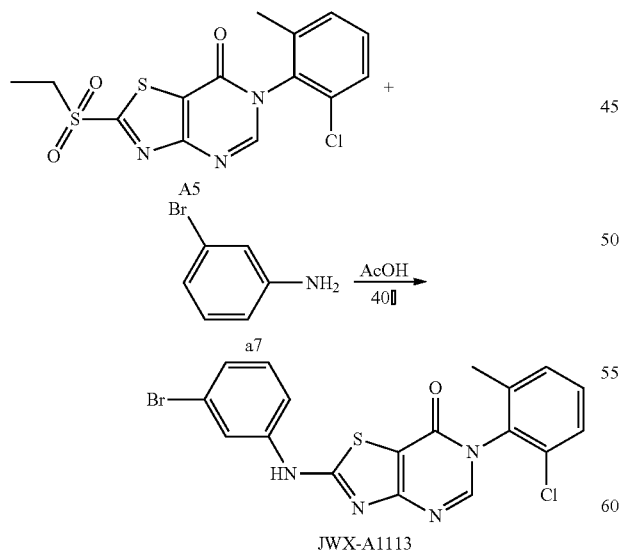

The title compound was prepared following the general procedure of JWX-A0824. JWX-A1113 was obtained as a white solid. Yield: 75.0%. m.p.: 261-265° C.

¹H-NMR (400 MHz, DMSO-d$_6$) δ 11.33 (s, 1H), 8.42 (s, 1H), 8.16 (s, 1H), 7.65-7.26 (m, 6H), 2.14 (s, 3H). ¹³C-NMR (101 MHz, DMSO-d$_6$) δ 167.36, 166.17, 155.17, 150.87, 141.49, 139.08, 133.96, 132.28, 131.59, 131.43, 130.23, 128.06, 126.33, 122.46, 121.18, 117.84, 108.87, 18.18.

Example 9: Preparation of 6-(2-Chloro-6-methylphenyl)-2-((3-chlorophenyl)amino)thiazolo[4,5-d]pyrimidin-7(6H)-one (JWX-A1116)

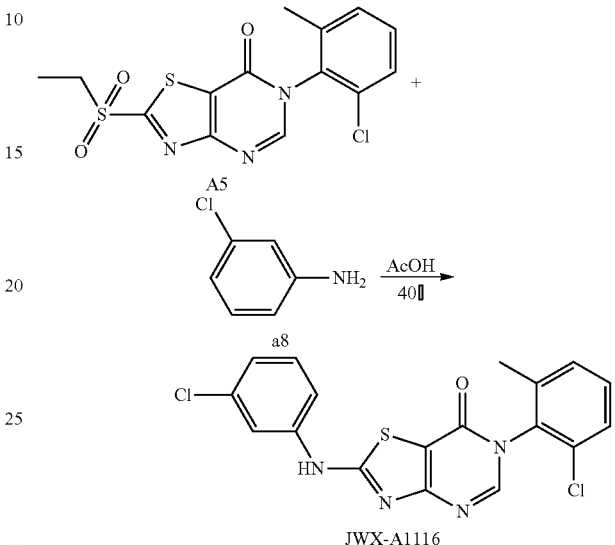

The title compound was prepared following the general procedure of JWX-A0824. JWX-A1116 was obtained as a white solid. Yield: 81.1%. m.p.: 244-252° C.

¹H-NMR (400 MHz, DMSO-d$_6$) δ 11.33 (s, 1H), 8.41 (s, 1H), 8.02 (s, 1H), 7.60-7.37 (m, 5H), 7.16 (d, J=7.9 Hz, 1H), 2.13 (s, 3H). ¹³C-NMR (101 MHz, DMSO-d$_6$) δ 167.39, 166.17, 155.17, 150.86, 141.35, 139.07, 134.01, 133.95, 132.27, 131.42, 131.29, 130.22, 128.05, 123.42, 118.37, 117.46, 108.87, 18.16.

Example 10: Preparation of 6-(2-Chloro-6-methylphenyl)-2-((4-fluorophenyl)amino)thiazolo[4,5-d]pyrimidin-7(6H)-one (JWX-A1119)

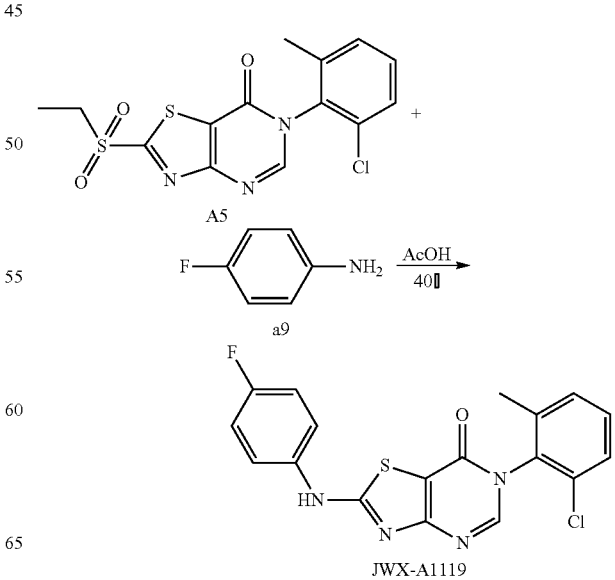

The title compound was prepared following the general procedure of JWX-A0824. JWX-A119 was obtained as a reddish white solid. Yield: 73%. m.p.: 285-291° C.

¹H-NMR (400 MHz, DMSO-d₆) δ 11.18 (s, 1H), 8.38 (s, 1H), 7.76 (dd, J=8.6, 4.7 Hz, 2H), 7.62-7.41 (m, 3H), 7.27 (t, J=8.7 Hz, 2H), 2.13 (s, 3H). ¹³C-NMR (101 MHz, DMSO-d₆) δ 167.94, 166.43, 159.87, 157.47, 155.11, 150.77, 139.09, 136.41, 134.01, 132.30, 131.38, 130.20, 128.04, 121.15, 121.07, 116.45, 116.22, 108.33, 18.16.

Example 11: Preparation of 6-(2-Chloro-6-methylphenyl)-2-(methyl(phenyl)amino)thiazolo[4,5-d]pyrimidin-7(6H)-one (JWX-A1114)

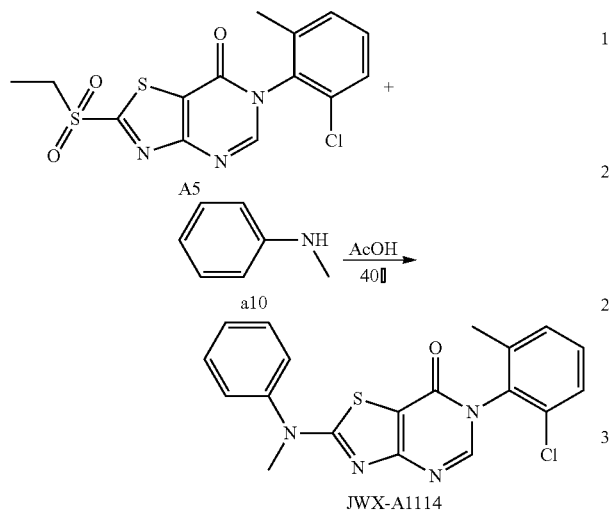

The title compound was prepared following the general procedure of JWX-A0824. JWX-A114 was obtained as a yellow green solid. Yield: 34.7%. m.p.: 169-177° C.

¹H-NMR (400 MHz, DMSO-d₆) δ 8.35 (s, 1H), 7.51 (m, 8H), 3.60 (s, 3H), 2.10 (s, 3H). ¹³C-NMR (101 MHz, DMSO-d₆) δ 173.08, 166.80, 154.92, 150.84, 144.60, 139.09, 134.03, 132.32, 131.36, 130.80, 130.18, 128.94, 128.04, 126.46, 108.41, 41.22, 18.13.

Example 12: Preparation of 6-(2-Chloro-6-methylphenyl)-2-(m-tolylamino)thiazolo[4,5-d]pyrimidin-7(6H)-one (JWX-A1211)

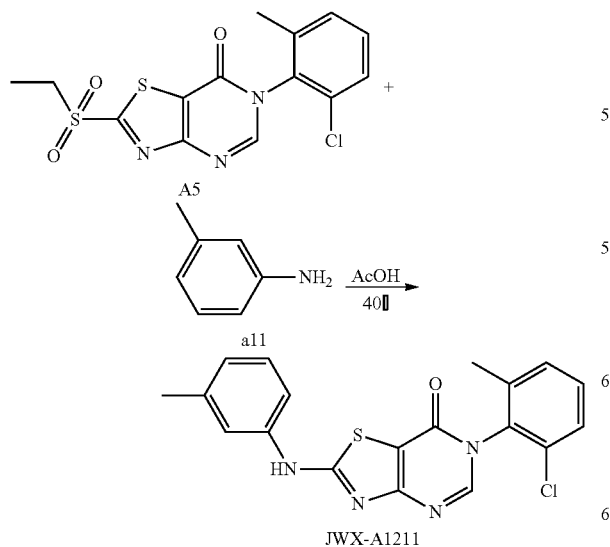

The title compound was prepared following the general procedure of JWX-A0824. JWX-A1211 was obtained as a brown solid. Yield: 78.3%. m.p.: 203-209° C.

¹H-NMR (400 MHz, DMSO-d₆) δ 11.09 (s, 1H), 8.37 (s, 1H), 7.61-7.42 (m, 5H), 7.29 (t, J=8.0 Hz, 1H), 6.95 (d, J=7.4 Hz, 1H), 2.34 (s, 3H), 2.13 (s, 3H). ¹³C-NMR (101 MHz, DMSO-d₆) δ 168.46, 166.97, 155.64, 151.21, 140.41, 139.58, 134.52, 132.80, 131.89, 130.71, 130.07, 128.54, 125.35, 120.19, 116.99, 108.68, 22.21, 18.67.

Example 13: Preparation of 6-(2-Chloro-6-methylphenyl)-2-((3-fluorophenyl)amino)thiazolo[4,5-d]pyrimidin-7(6H)-one (JWX-A1214)

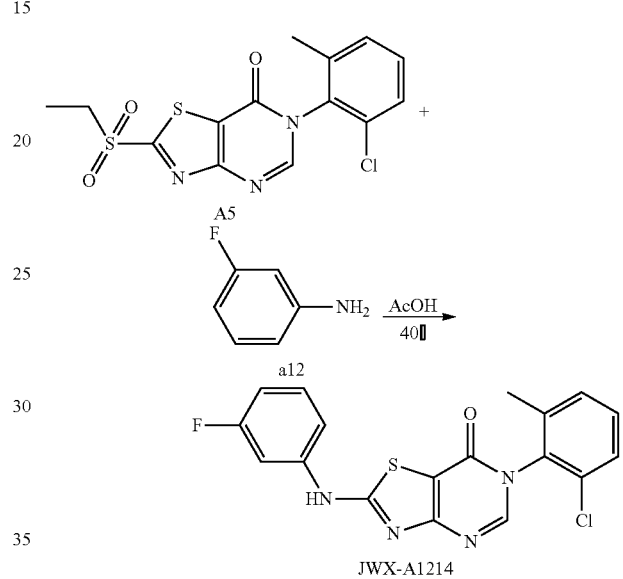

The title compound was prepared following the general procedure of JWX-A0824. JWX-A1214 was obtained as a white solid. Yield: 93.6%. m.p.: 238-245° C.

¹H-NMR (400 MHz, DMSO-d₆) δ 11.38 (s, 1H), 8.41 (s, 1H), 7.82 (d, J=10.9 Hz, 1H), 7.64-7.34 (m, 5H), 6.94 (s, 1H), 2.13 (s, 3H). ¹³C-NMR (101 MHz, DMSO-d₆) δ 167.42, 166.19, 164.10, 161.69, 155.21, 150.87, 141.63, 141.52, 139.08, 133.94, 132.26, 131.44, 131.36, 131.27, 130.24, 128.06, 114.83, 110.32, 110.11, 108.82, 106.00, 105.73, 18.16.

Example 14: Preparation of 6-(2-Chloro-6-methylphenyl)-2-(p-tolylamino)thiazolo[4,5-d]pyrimidin-7(6H)-one (JWX-A1218)

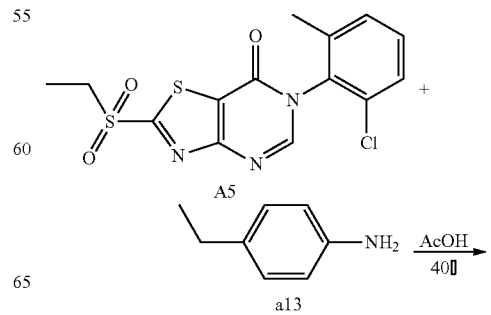

-continued

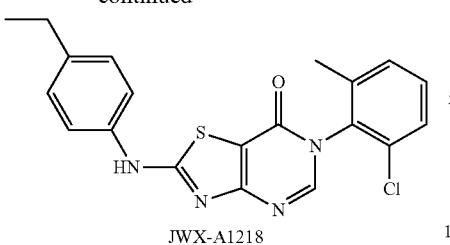

JWX-A1218

The title compound was prepared following the general procedure of JWX-A0824. JWX-A1218 was obtained as a white solid. Yield: 63.2%. m.p.: 236-244° C.

$^1$H-NMR (400 MHz, DMSO-d$_6$) δ 11.03 (s, 1H), 8.35 (s, 2H), 7.81-7.39 (m, 10H), 7.24 (d, J=7.9 Hz, 4H), 2.59 (dd, J=14.5, 7.1 Hz, 4H), 2.13 (s, 6H), 1.18 (t, J=7.4 Hz, 6H). $^{13}$C-NMR (101 MHz, DMSO-d$_6$) δ 168.08, 166.65, 155.07, 150.60, 139.58, 139.11, 138.06, 134.11, 132.34, 131.31, 130.17, 128.89, 128.02, 119.54, 107.87, 28.09, 18.17, 16.12.

Example 15: Preparation of 6-(2-Chloro-6-methylphenyl)-2-((3,4-dimethylphenyl)amino)thiazolo[4,5-d]pyrimidin-7(6H)-one (JWX-A0315)

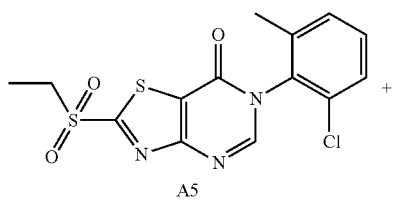

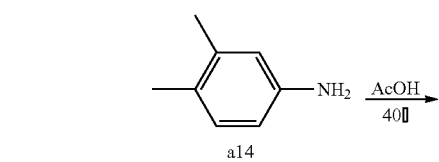

JWX-A0315

The title compound was prepared following the general procedure of JWX-A0824. JWX-A0315 was obtained as a white needle-like solid. Yield: 87.7%. m.p.: 226-228° C.

$^1$H-NMR (400 MHz, DMSO-d$_6$) δ 11.03 (s, 1H), 8.38 (s, 1H), 7.57 (d, J=7.5 Hz, 1H), 7.47 (dd, J=20.9, 8.3 Hz, 4H), 7.17 (d, J=7.8 Hz, 1H), 2.25 (s, 3H), 2.21 (s, 3H), 2.13 (s, 3H). $^{13}$C-NMR (101 MHz, DMSO-d$_6$) δ 168.16, 166.58, 155.10, 150.72, 139.10, 137.71, 137.55, 134.06, 132.31, 131.39, 130.59, 130.21, 128.05, 120.60, 117.01, 107.88, 20.17, 19.31, 18.18.

Example 16: Preparation of 6-(2-Chloro-6-methylphenyl)-2-((3,4,5-trimethylphenyl)amino)thiazolo[4,5-d]pyrimidin-7(6H)-one (JWX-A0322)

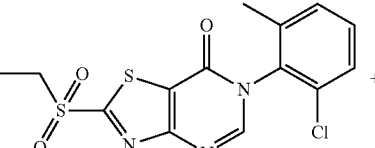

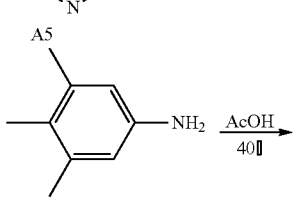

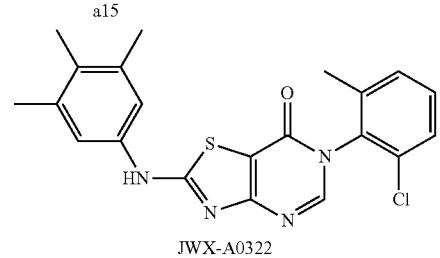

JWX-A0322

The title compound was prepared following the general procedure of JWX-A0824. JWX-A0322 was obtained as a light yellow solid. Yield: 82.0%. m.p.: 260-262° C.

$^1$H-NMR (400 MHz, DMSO-d$_6$) δ 10.97 (s, 1H), 8.37 (s, 1H), 7.56 (d, J=7.3 Hz, 1H), 7.47 (dd, J=19.2, 7.2 Hz, 2H), 7.31 (s, 2H), 2.26 (s, 6H), 2.13 (s, 3H), 2.10 (s, 3H). $^{13}$C-NMR (101 MHz, DMSO-d$_6$) δ 168.36, 166.60, 155.09, 150.67, 139.10, 137.35, 136.94, 134.08, 132.32, 131.37, 130.95, 130.20, 128.04, 118.75, 107.75, 20.97, 18.18, 15.17.

Example 17: Preparation of 6-(2-Chloro-6-methylphenyl)-2-(pyridin-2-ylamino)thiazolo[4,5-d]pyrimidin-7(6H)-one (JWX-A0828)

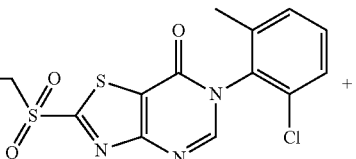

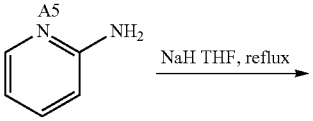

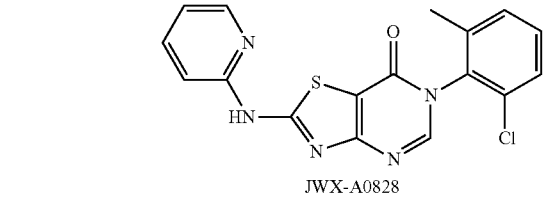

JWX-A0828

Compound A5 (370 mg, 1.0 mmol) and 2-aminopyridine b2 (189 mg, 2.0 mmol) were dissolved in anhydrous THF (3 mL). Then, NaH (48 mg, 2.0 mmol) was added to the solution, dry condenser tube was equipped with a balloon on the top. The reaction was held at reflux for 0.5 h, then the reaction was stopped and cooled to room temperature, and residual NaH was destroyed by adding a small amount of ethanol. The reaction mixture was concentrated and purified by column chromatography (CH$_2$Cl$_2$:MeOH=50:1) to yield JWX-A0828 as a yellow solid. Yield: 208 mg, 56.2%. m.p.: 270-271° C.

$^1$H-NMR (400 MHz, DMSO-d$_6$) δ 12.33 (s, 1H), 8.50-8.42 (m, 1H), 8.38 (s, 1H), 7.89-7.80 (m, 1H), 7.59-7.45 (m, 3H), 7.19 (d, J=8.3 Hz, 1H), 7.13-7.10 (m, 1H), 2.13 (s, 3H). $^{13}$C-NMR (101 MHz, DMSO-d$_6$) δ 164.3, 164.0, 155.4, 150.7, 150.0, 146.4, 138.7, 133.7, 131.9, 130.8, 129.7, 127.6, 117.8, 111.8, 109.5, 17.7. HRMS: m/z calcd. for C$_{17}$H$_{13}$ClN$_5$OS [M+H]$^+$ 370.0524; found 370.0526.

Example 18: Preparation of 6-(2-Chloro-6-methyl-phenyl)-2-((6-chloropyrimidin-4-yl)amino)thiazolo[4,5-d]pyrimidin-7(6H)-one (JWX-A0912)

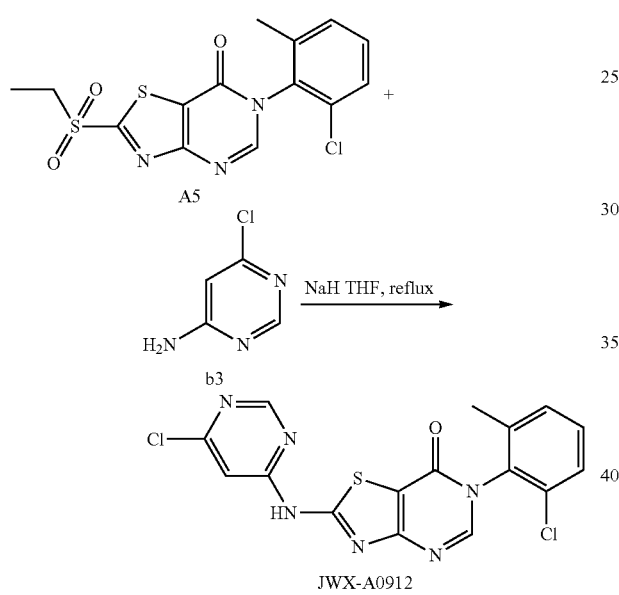

The title compound was prepared following the general procedure of LD486. JWX-A0912 was obtained. Yield: 65.0%. m.p.: 335-337° C.

$^1$H-NMR (400 MHz, DMSO-d$_6$) δ 12.90 (s, 1H), 8.88 (s, 1H), 8.46 (s, 1H), 7.65-7.40 (m, 3H), 7.20 (s, 1H), 2.15 (s, 3H). $^{13}$C-NMR (101 MHz, DMSO-d$_6$) δ 163.97, 159.66, 158.17, 155.89, 150.94, 139.13, 133.96, 132.30, 131.45, 130.25, 128.08, 112.07, 107.83, 18.21.

Example 19: Preparation of 6-(2-Chloro-6-methyl-phenyl)-2-((6-chloropyridazin-3-yl)amino)thiazolo[4,5-d]pyrimidin-7(6H)-one (JWX-A0918)

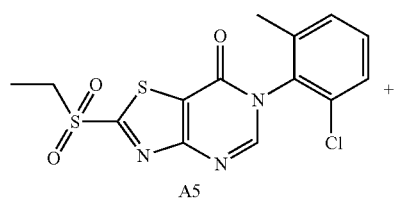

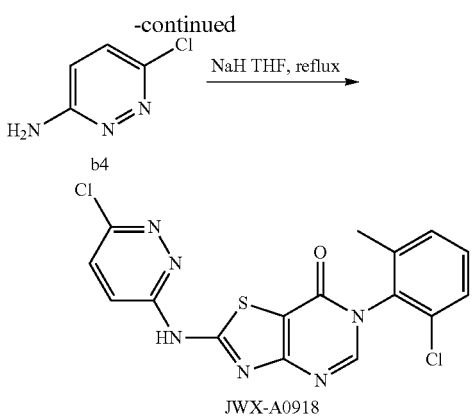

The title compound was prepared following the general procedure of LD486. JWX-A0918 was obtained as a grey solid. Yield: 99.9%. m.p.: 272-274° C.

$^1$H-NMR (400 MHz, DMSO-d$_6$) δ 12.77 (s, 1H), 8.46 (s, 1H), 7.91 (d, J=9.3 Hz, 1H), 7.53 (ddd, J=19.2, 15.3, 8.3 Hz, 4H), 2.16 (s, 3H). $^{13}$C-NMR (101 MHz, DMSO-d$_6$) δ 163.97, 155.96, 153.10, 151.05, 150.89, 139.15, 134.04, 132.34, 131.42, 131.35, 130.24, 128.07, 121.44, 18.21.

Example 20: Preparation of 6-(2-Chloro-6-methyl-phenyl)-2-((6-(4-(2-hydroxyethyl)piperazin-1-yl)-2-methylpyrimidin-4-yl)amino)thiazolo[4,5-d]pyrimidin-7(6H)-one (JWX-A0728)

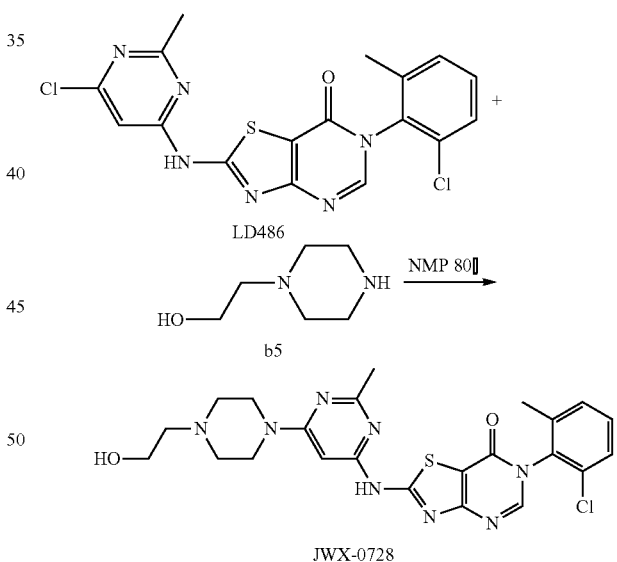

Compound LD486 (500 mg, 1.2 mmol) was dissolved in anhydrous NMP (5 mL), and hydroxyethylpiperazine b5 was added (0.31 g, 2.4 mmol). The reaction was held at 80° C. for 2 h, then cooled to room temperature. The reaction was poured into ice water, the precipitated solid was filtered by vacuum, washed with water and dried to obtain JWX-A0728 as a yellow solid. Yield: 0.62 g, 95.6%. The solid was recrystallized in ethanol, m.p.: 284-285° C.

$^1$H-NMR (400 MHz, CDCl$_3$) δ 7.86 (s, 1H), 7.55-7.31 (m, 3H), 6.92 (s, 1H), 3.86-3.59 (m, 6H), 2.65-2.50 (m, 9H), 2.25 (s, 3H). $^{13}$C-NMR (101 MHz, DMSO-d$_6$) δ 165.5, 165.0, 164.3, 162.9, 157.2, 155.9, 150.4, 139.1, 134.2, 132.4, 131.3, 130.2, 128.0, 111.2, 83.8, 60.6, 59.0, 53.2, 44.1, 25.9, 18.2. HRMS: m/z calcd. for $C_{23}H_{26}ClN_8O_2S$ [M+H]+ 513.1583; found 513.1592.

Example 21: Preparation of 6-(2-Chloro-6-methylphenyl)-2-((2-methyl-6-morpholinopyrimidin-4-yl)amino)thiazolo[4,5-d]pyrimidin-7(6H)-one (JWX-A1012)

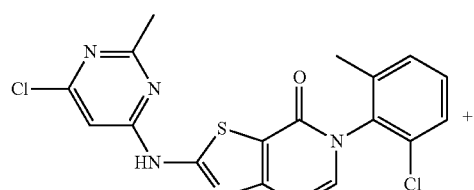

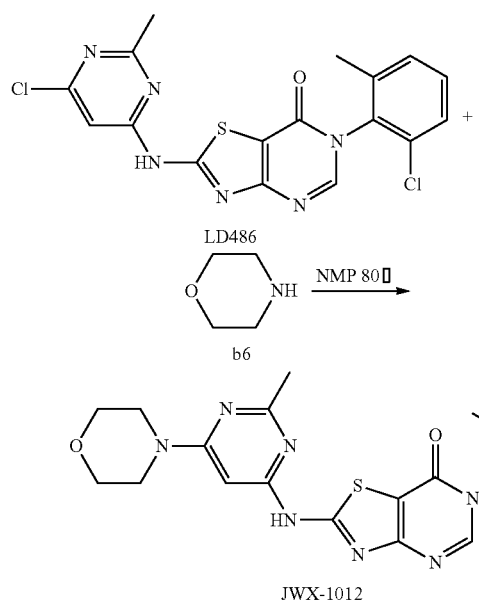

The title compound was prepared following the general procedure of JWX-A0728. JWX-A1012 was obtained as a white solid. Yield: 49.6%. m.p.: 325-327° C.

$^1$H-NMR (400 MHz, DMSO-$d_6$) δ 12.12 (s, 1H), 8.34 (s, 1H), 7.54 (d, J=7.3 Hz, 1H), 7.45 (dd, J=18.8, 7.1 Hz, 3H), 6.06 (s, 1H), 3.65 (s, 4H), 3.49 (s, 4H), 2.42 (s, 3H), 2.10 (s, 3H). $^{13}$C-NMR (101 MHz, DMSO-$d_6$) δ 165.59, 164.96, 164.30, 163.15, 157.21, 155.94, 150.52, 139.14, 134.18, 132.35, 131.35, 130.22, 128.07, 111.17, 83.95, 66.22, 44.39, 25.87, 18.18.

Example 22: Preparation of 6-(2-Chloro-6-methylphenyl)-2-((2-methyl-6-(4-methylpiperazin-1-yl)pyrimidin-4-yl)amino)thiazolo[4,5-d]pyrimidin-7(6H)-one (JWX-A1022)

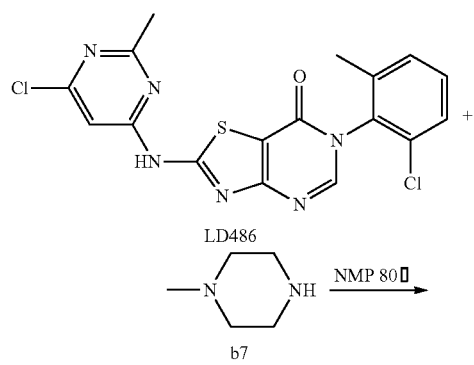

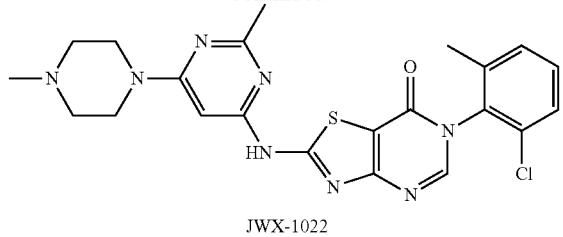

The title compound was prepared following the general procedure of JWX-A0728. JWX-A1022 was obtained as a white solid. Yield: 95.4%. m.p.: 325-327° C.

$^1$H-NMR (400 MHz, DMSO-$d_6$) δ 12.08 (s, 1H), δ 8.31 (s, 1H), 7.51 (d, J=7.5 Hz, 1H), 7.47-7.37 (m, 2H), 6.04 (s, 1H), 3.48 (s, 4H), 2.38 (s, 3H), 2.31 (s, 4H), 2.15 (s, 3H), 2.08 (s, 3H). $^{13}$C-NMR (101 MHz, DMSO-$d_6$) δ 165.55, 165.00, 164.31, 162.88, 157.19, 155.93, 150.48, 139.14, 134.18, 132.35, 131.33, 130.21, 128.06, 111.15, 83.87, 54.58, 46.18, 43.94, 25.88, 18.18.

Example 23: Preparation of 6-Mesityl-2-(phenylamino)thiazolo[4,5-d]pyrimidin-7(6H)-one (LD252)

1. Synthesis of 2-chloro-N-mesitylacetamide (B2)

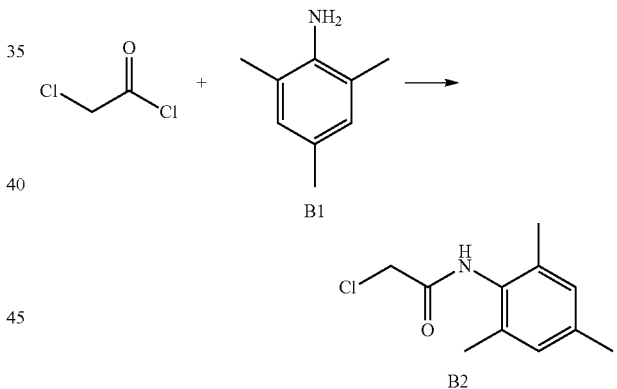

The title compound was prepared following the general procedure of A2. B2 was obtained as a white solid. Yield: 57%. The crude product was used in the next step without purification.

2. Synthesis of 4-Amino-N-mesityl-2-(ethylthio)thiazole-5-carboxamide (B3)

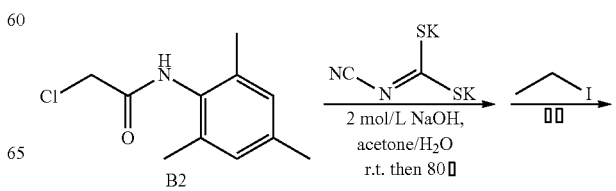

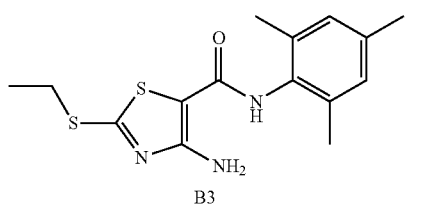

The title compound was prepared following the general procedure of A3. B3 was obtained as a light yellow solid. Yield: 84.0%.

3. Synthesis of 6-mesityl-2-(Ethylsulfonyl)thiazolo[4,5-d]pyrimidin-7(6H)-one (B5)

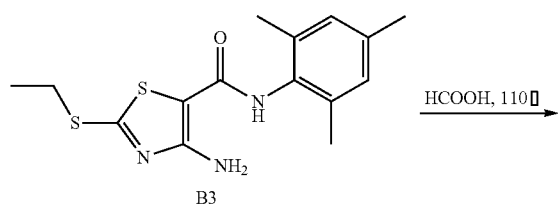

The title compound was prepared following the general procedure of A5. B5 was obtained as a white solid. Yield: 77.0%.

4. Synthesis of 6-Mesityl-2-(phenylamino)thiazolo[4,5-d]pyrimidin-7(6H)-one (LD252)

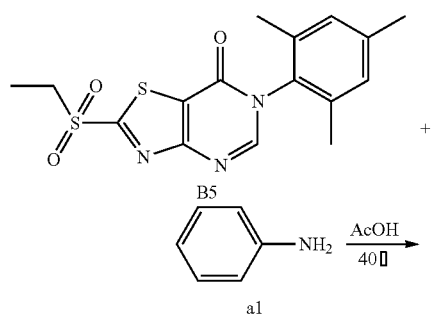

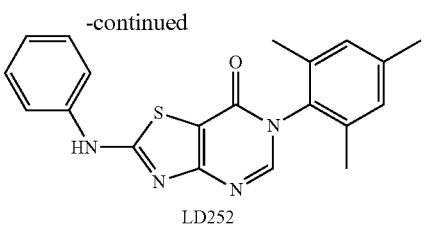

The title compound was prepared following the general procedure of JWX-A0824. LD252 was obtained as a white solid. Yield: 73.0%. m.p.: 151-153° C.

$^1$H-NMR (400 MHz, CDCl$_3$) δ 10.25 (s, 1H), 7.91 (s, 1H), 7.63 (d, J=7.8 Hz, 2H), 7.32 (t, J=7.5 Hz, 2H), 7.12 (t, J=7.1 Hz, 1H), 6.98 (s, 2H), 2.30 (s, 3H), 2.08 (s, 6H). $^{13}$C-NMR (101 MHz, CDCl$_3$) δ 169.2, 165.2, 155.3, 148.6, 138.8, 138.2, 134.5, 131.8, 128.6, 128.3, 123.7, 119.3, 108.0, 20.1, 16.9. HRMS: m/z calcd. for C$_{20}$H$_{19}$N$_4$OS [M+H]$^+$ 363.1274; found 363.1276.

Example 24: Preparation of 6-Mesityl-2-(pyridin-2-ylamino)thiazolo[4,5-d]pyrimidin-7(6H)-one (LD286)

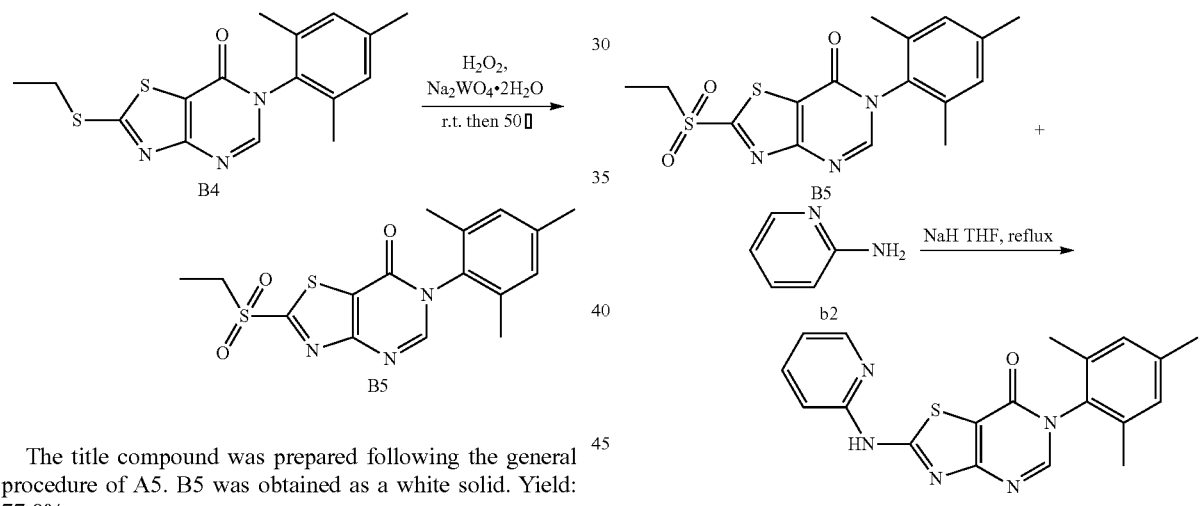

The title compound was prepared following the general procedure of JWX-A0828. LD286 was obtained.

Example 25: Preparation of 6-Mesityl-2-(pyridin-4-ylamino)thiazolo[4,5-d]pyrimidin-7(6H)-one (LD293)

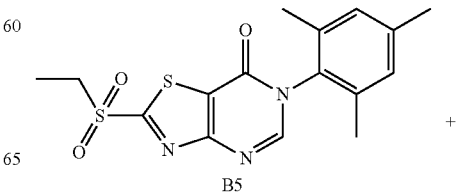

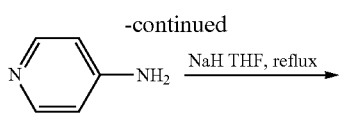

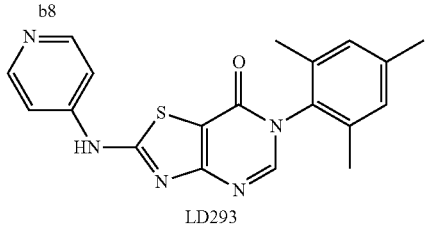

The title compound was prepared following the general procedure of JWX-A0828. LD293 was obtained.

Example 26: Preparation of 6-(2,6-Dichlorophenyl)-2-(methylthio) thiazolo[4,5-d]pyrimidin-7(6H)-one (LD493)

1. Synthesis of 2-chloro-N-(2,6-dichlorophenyl)acetamide (C2)

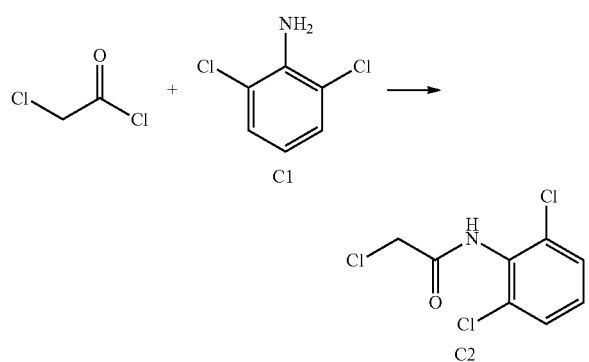

The title compound was prepared following the general procedure of A2. C2 was obtained as a white scaly solid. Yield: 98.0%. The crude product was used in the next step without purification.

2. Synthesis of 4-amino-N-(2,6-dichlorophenyl)-2-(methylthio) thiazole-5-carboxamide (C3)

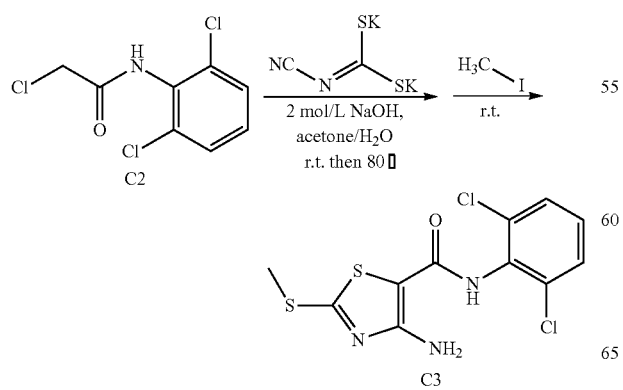

The title compound was prepared following the general procedure of A3. C3 was obtained as an orange-red solid. Yield: 59.0%.

3. Synthesis of 6-(2,6-dichlorophenyl)-2-(methylthio)thiazolo[4,5-d]pyrimidin-7(6H)-one (LD493)

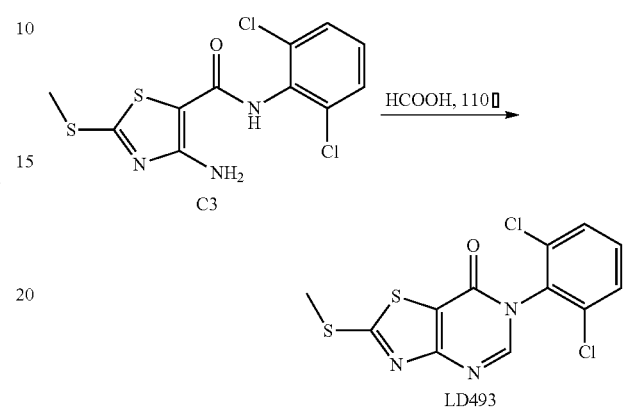

The title compound was prepared following the general procedure of A4. LD493 was obtained as a light yellow solid. Yield: 93.0%. m.p.: 134-135° C.

Example 27: Preparation of 6-(((6-Chloro-2-methylpyrimidin-4-yl) amino)-3-(2-chloro-6-methylphenyl) thiazolo[4,5-d][1,2,3]triazin-4(3H)-one (JWX-A3N)

1. Synthesis of 3-(2-chloro-6-methylphenyl)-6-(ethylsulfonyl)thiazolo[4,5-d][1,2,3]triazin-4(3H)-one (A5')

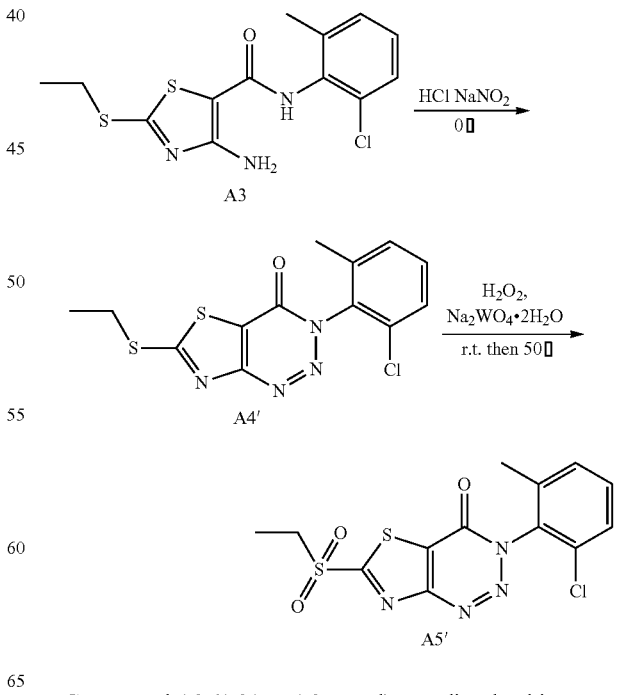

Compound A3 (1.31 g, 4.0 mmol) was dissolved in conc. HCl (4 mL) and cooled to 0° C. A solution of NaNO$_2$ (0.35 g, 5.0 mmol) in water (1.0 mL) was slowly added. The reaction was warmed slowly to room temperature and held for 2 h. Water (20 mL) was added, the precipitated solid was filtered by vacuum, washed with water and dried to obtain compound A4' as a pink solid.

Compound A4' (6.78 g, 20 mmol) was suspended in ethanol (100 mL) and Na$_2$WO$_4$.2H$_2$O (1.00 g, 3 mmol) was added. 30% hydrogen peroxide solution (15 mL) was added dropwise slowly, and the reaction mixture was reacted for 1 h at room temperature, then heated to 50° C. for 1 h. After the completion of reaction, water (100 mL) was added, and no solid precipitated. The reaction mixture was extracted with ethyl ether (20 mL×5), the organic phase was combined, washed with saturated brine, dried with Na$_2$SO$_4$, and concentrated to afford the compound A5' as a yellow foamy solid. Yield: 70.0%. The crude product was used in the next step without purification.

2. Synthesis of 6-((6-chloro-2-methylpyrimidin-4-yl)amino)-3-(2-chloro-6-methylphenyl)thiazolo[4,5-d][1,2,3]triazin-4(3H)-one (JWX-A3N)

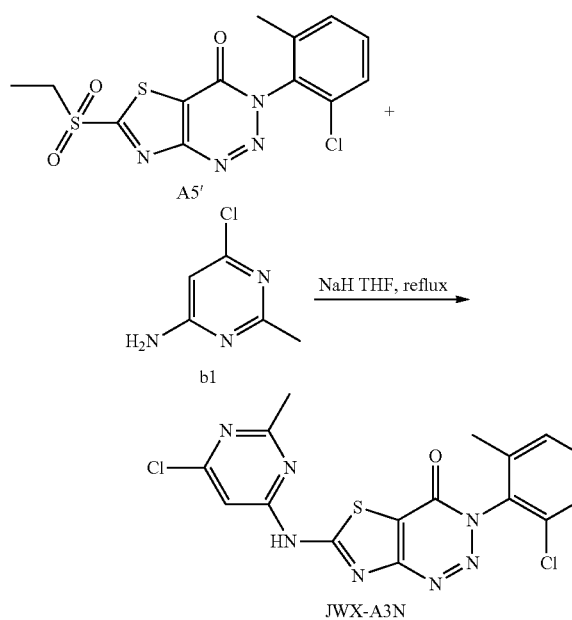

Compound A5' (370 mg, 1.0 mmol) and 2-methyl-4-amino-6-chloropyrimidine b1 (287 mg, 2.0 mmol) were dissolved in anhydrous THF (3 mL). NaH (48 mg, 2.0 mmol) was added to the solution, and dry condenser tube was equipped with a balloon on the top. The reaction was held at reflux for 0.5 h, then the reaction was stopped and cooled to room temperature, the reaction mixture was poured into ice water, the pH was adjusted to neutral by adding dilute hydrochloric acid dropwise, a large amount of solid was precipitated out. The precipitated solid was filtered by vacuum, washed with water and dried to obtain JWX-A3N as a yellow solid. Yield: 294 mg, 70.0%. m.p.: 315-317° C.

$^1$H-NMR (400 MHz, DMSO-d$_6$) δ 13.19 (s, 1H), 7.64-7.48 (m, 3H), 7.06 (s, 1H), 2.67 (s, 3H), 2.14 (s, 3H).

$^{13}$C-NMR (101 MHz, CDCl$_3$) δ 172.58, 169.59, 165.26, 164.54, 162.57, 157.32, 143.67, 139.97, 136.74, 135.14, 132.90, 122.16, 109.72, 30.21, 22.62.

Example 28: Preparation of 3-(2,6-Dichlorophenyl)-6-(methylthio) thiazolo[4,5-d][1,2,3]triazin-4(3H)-one (LD496)

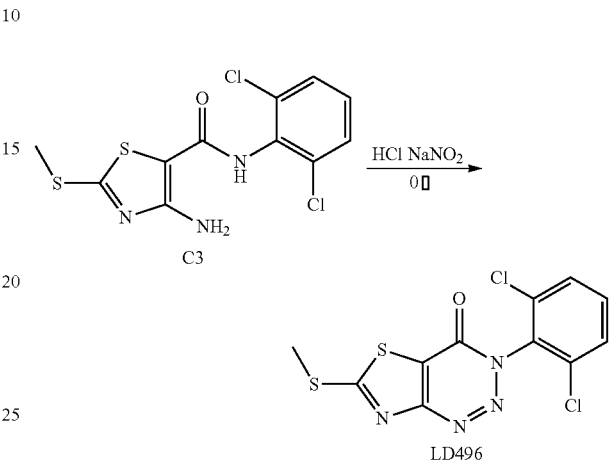

The title compound was prepared following the general procedure of A4'. LD496 was obtained as a reddish brown solid. Yield: 84.0%.

Example 29: Preparation of 6-(2-Chloro-6-methylphenyl)-2-hydroxythiazolo[4,5-d]pyrimidin-7(6H)-one (JWX-A0903)

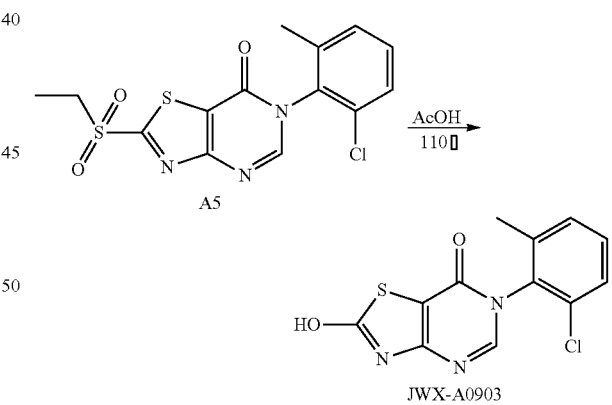

Compound A5 (0.37 g, 1.0 mmol) was dissolved in AcOH (7 mL). The reaction was held at 110° C. for 2 h. Water was added and solid was precipitated out. The precipitated solid was filtered by vacuum and dried to obtain JWX-A0903 as a white solid. Yield: 0.218 g, 74.2%. m.p.: 230-233° C.

$^1$H-NMR (400 MHz, DMSO-d$_6$) δ 13.05 (s, 1H), δ 8.46 (s, 1H), 7.61-7.54 (m, 1H), 7.48 (dt, J=14.7, 7.3 Hz, 2H), 2.14 (s, 3H). $^{13}$C-NMR (101 MHz, DMSO-d$_6$) δ 169.57, 153.89, 153.71, 151.96, 138.99, 133.60, 132.10, 131.60, 130.28, 128.07, 101.68, 18.13.

Example 30: Preparation of 6-(2-chloro-6-methylphenyl)-2-(Benzylthio)thiazolo[4,5-d]pyrimidin-7(6H)-one (JWX-A1223)

1. Synthesis of 4-amino-N-(2-chloro-6-methylphenyl)-2-(benzylthio)thiazole-5-carboxamide (A3-1)

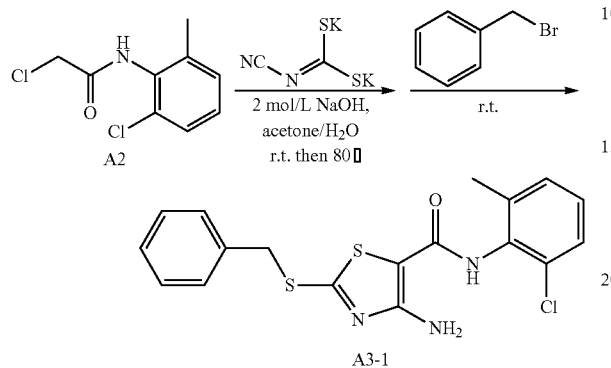

Compound A2 (10.9 g, 50 mmol) was dissolved in acetone (100 mL). Then, the solution of dipotassium cyanodithiomidocarbonate (9.7 g, 50 mmol, 100 ml) in water (100 mL) was added to the system and 2 mol/L NaOH aqueous solution (25 mL) were added to the solution. The reaction mixture was stirred for 2 h at room temperature, then heated to 80° C. for 0.5 h. Afterward, the reaction mixture was cooled to room temperature. To the mixture benzyl bromide (8.55 g, 50 mmol) was added dropwise and a large quantity of yellow solid quickly appeared. After reaction for 1 h at room temperature, the reaction mixture was poured into ice water. the precipitated solid was filtered by vacuum, washed with water and dried to obtain compound A3-1 as a yellow solid. Yield: 16.2 g, 83.1%.

2. Synthesis of 6-(2-chloro-6-methylphenyl)-2-(benzylthio)thiazolo[4,5-d]pyrimidin-7(6H)-one (JWX-A1223)

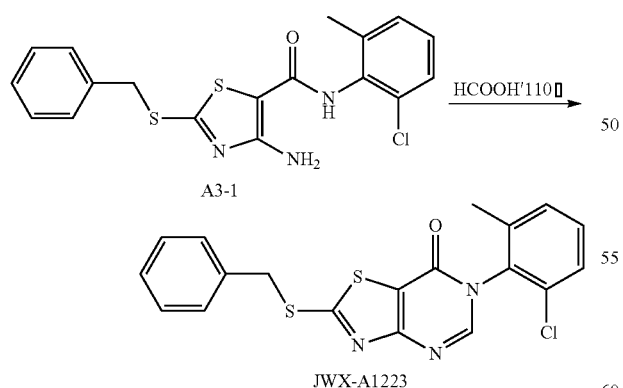

Compound A3-1(1.17 g, 3 mmol) was dissolved in HCOOH (2 mL). The reaction was held at reflux for 1 h, then cooled to room temperature. Water was added, the reaction mixture was allowed to stand, and the water layer was discarded. Ethyl ether was added, and after dissolution, $Na_2SO_4$ was added to dry. The solution was concentrated and purified by column chromatography concentrated (petroleum ether:EtOAc=10:1) to afford JWX-A1223 as a yellow solid. Yield: 21.3%. m.p.: 134-138° C.

$^1$H-NMR (400 MHz, DMSO-$d_6$) δ 8.52 (s, 1H), 7.44 (m, 8H), 4.70 (s, 2H), 2.13 (s, 3H). $^{13}$C-NMR (101 MHz, DMSO-$d_6$) δ 175.72, 166.23, 155.04, 151.27, 139.06, 136.22, 133.57, 130.31, 129.62, 129.15, 128.90, 128.30, 128.10, 116.81, 37.54, 18.15.

Example 31: Preparation of 6-(2-chloro-6-methylphenyl)-2-(Benzylamino)thiazolo[4,5-d]pyrimidin-7(6H)-one (JWX-A1228)

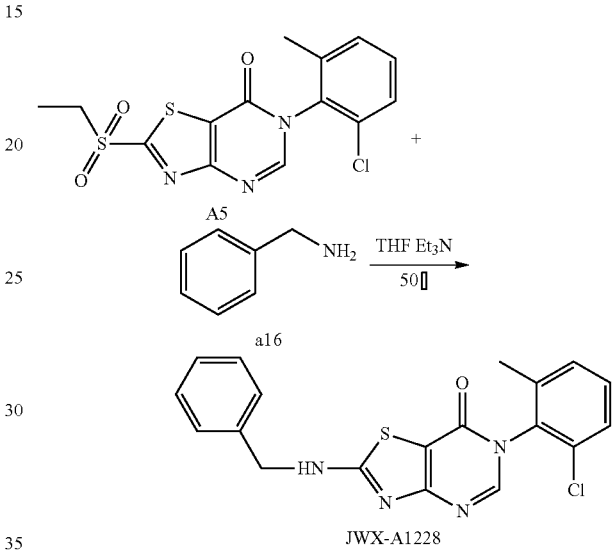

Compound A5 (370 mg, 1.0 mmol) was dissolved in anhydrous THF (5 mL). Then, benzylamine a16 (321 mg, 3.0 mmol) and $Et_3N$ (0.5 mL) were added to the solution, and the reaction was held at 50° C. overnight. The reaction mixture was concentrated and purified by column chromatography ($CH_2Cl_2$:MeOH=150:1) to afford the compound JWX-A1228 as a white solid. Yield: 0.127 g, 33.2%. m.p.: 155-161° C.

$^1$H-NMR (400 MHz, DMSO-$d_6$) δ 9.44 (s, 1H), 8.28 (s, 1H), 7.62-7.21 (m, 8H), 4.65 (s, 2H), 2.12 (s, 3H). $^{13}$C-NMR (101 MHz, DMSO-$d_6$) δ 172.04, 166.93, 155.00, 150.43, 139.12, 138.27, 134.18, 132.38, 131.25, 130.12, 128.99, 128.03, 127.99, 127.83, 107.36, 48.13, 18.17.

Example 32: Preparation of 6-(2-Chloro-6-methylphenyl)-2-(n-propylamino)thiazolo[4,5-d]pyrimidin-7(6H)-one (JWX-A1229)

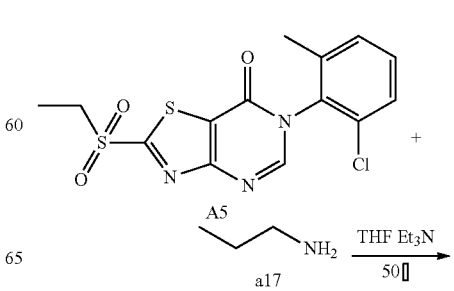

-continued

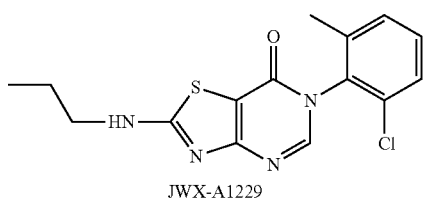

JWX-A1229

The title compound was prepared following the general procedure of JWX-A1228. JWX-A1228 was obtained as a light yellow solid. Yield: 60.7%. m.p.: 193-196° C.

$^1$H-NMR (400 MHz, DMSO-d$_6$) δ 8.94 (s, 1H), 8.27 (s, 1H), 7.73-7.23 (m, 3H), 3.35 (m, 2H), 2.12 (s, 3H), 1.81-1.48 (m, 2H), 0.94 (t, J=7.3 Hz, 3H). $^{13}$C-NMR (101 MHz, DMSO-d$_6$) δ 172.00, 167.12, 154.94, 150.37, 139.12, 134.21, 132.37, 131.23, 130.11, 127.98, 106.78, 46.66, 22.19, 18.15, 11.78, 11.30.

Example 33: Preparation of 6-(2-Chloro-6-methylphenyl)-2-((3-fluoro-4-methylphenyl)amino)thiazolo[4,5-d]pyrimidin-7(6H)-one (JWX-A0108)

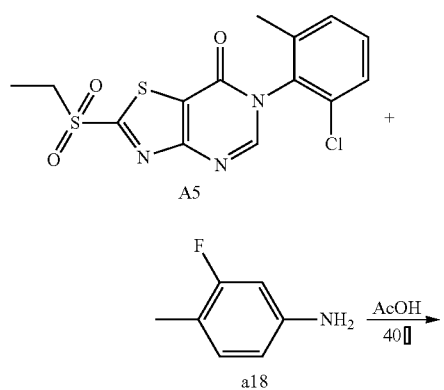

JWX-A0108

The title compound was prepared following the general procedure of JWX-A0824. JWX-A0108 was obtained as a white solid. Yield: 91.3%. m.p.: 222-226° C.

$^1$H-NMR (400 MHz, DMSO-d$_6$) δ 11.27 (s, 1H), 8.41 (s, 1H), 7.74 (d, J=12.6 Hz, 1H), 7.57 (dd, J=7.7, 1.0 Hz, 1H), 7.53-7.43 (m, 2H), 7.34-7.28 (m, 2H), 2.22 (s, 3H), 2.13 (s, 3H). $^{13}$C-NMR (101 MHz, DMSO-d$_6$) δ 167.47, 166.30, 162.18, 159.78, 155.15, 150.85, 139.22, 139.09, 133.99, 132.38, 132.28, 131.42, 130.23, 128.06, 119.28, 119.11, 114.76, 108.51, 106.03, 105.75, 18.17, 14.13.

Example 34: Preparation of N-(6-(2-Chloro-6-methylphenyl)-7-oxo-6,7-dihydrothiazolo[4,5-d]pyrimidin-2-yl)benzamide (JWX-A0121)

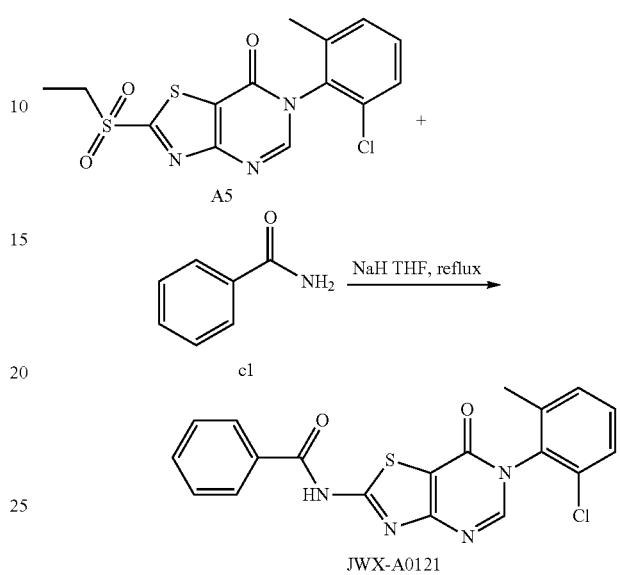

JWX-A0121

The title compound was prepared following the general procedure of JWX-A0828. JWX-A0121 was obtained as a light yellow solid. Yield: 45.5%. m.p.: 253-256° C.

$^1$H-NMR (400 MHz, DMSO-d$_6$) δ 13.49 (s, 1H), 8.50 (s, 1H), 8.18 (d, J=7.5 Hz, 2H), 7.70 (t, J=7.2 Hz, 1H), 7.60 (t, J=7.1 Hz, 3H), 7.55-7.45 (m, 2H), 2.15 (s, 3H). $^{13}$C-NMR (101 MHz, DMSO-d$_6$) δ 166.95, 165.01, 163.81, 156.13, 151.04, 139.13, 133.97, 133.85, 132.31, 131.64, 131.49, 130.29, 129.27, 128.97, 128.10, 111.68, 18.2.

Example 35: Preparation of N-(6-(2-Chloro-6-methylphenyl)-7-oxo-6,7-dihydrothiazolo[4,5-d]pyrimidin-2-yl)-4-methylbenzamide (JWX-A0310)

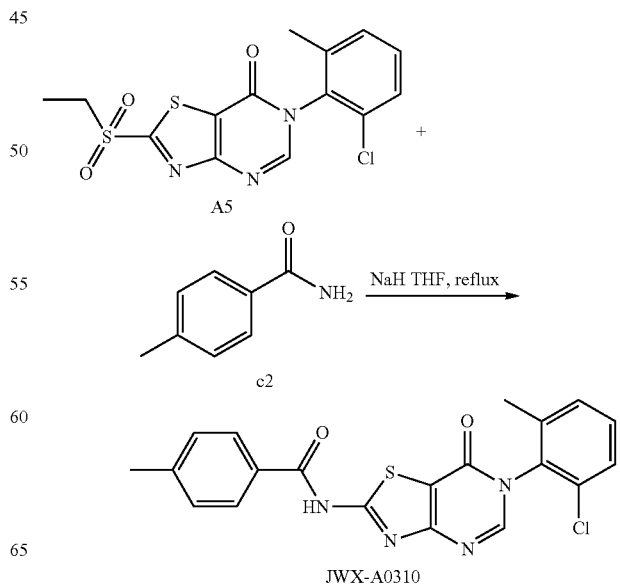

JWX-A0310

The title compound was prepared following the general procedure of JWX-A0828. JWX-A0310 was obtained as a white solid. Yield: 47.0%. m.p.: 272-274° C.

$^1$H-NMR (400 MHz, DMSO-d$_6$) δ 13.41 (s, 1H), 8.49 (s, 1H), 8.08 (d, J=8.0 Hz, 2H), 7.61-7.43 (m, 3H), 7.37 (d, J=8.0 Hz, 2H), 2.38 (s, 3H), 2.15 (s, 3H). $^{13}$C-NMR (101 MHz, DMSO-d$_6$) δ 166.63, 164.96, 163.81, 156.14, 150.98, 144.30, 139.13, 133.98, 132.32, 131.45, 130.26, 129.79, 129.00, 128.71, 128.09, 111.70, 21.63, 18.21.

Example 36: Preparation of 6-(2-Chloro-6-methylphenyl)-2-phenylthiazolo[4,5-d]pyrimidin-7(6H)-one (JWX-C1200)

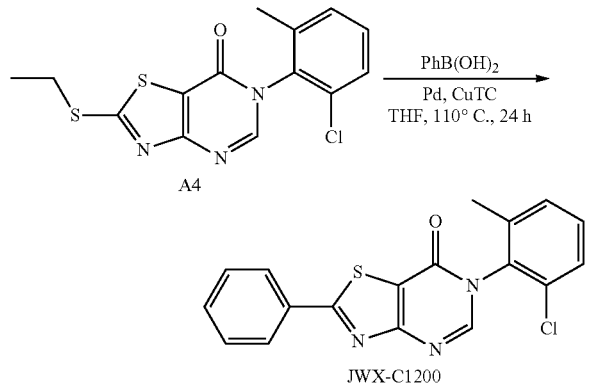

Compound A4 (100 mg, 0.3 mmol) was dissolved in anhydrous THF (5 mL). Then, Benzene boronic acid (73 mg, 0.6 mmol), CuTC (190 mg, 1 mmol) and Tetrakis(triphenylphosphine)palladium (34 mg, 0.015 mmol) was added to the solution, the reaction was held at 110° C. overnight. After filtered through celite, the reaction mixture was extracted with ethyl acetate and aqueous solution of NaHCO$_3$ (×3). Ethyl acetate layer was concentrated and purified by column chromatography (petroleum ether:EtOAc=10:1) to afford compound JWX-C1200 as a white solid. Yield: 148 mg, 84.0%. m.p.: 135-136° C.

$^1$H-NMR (400 MHz, CDCl$_3$) δ 8.16 (dd, J=8.1, 1.5 Hz, 1H), 8.03 (s, 1H), 7.59-7.50 (m, 2H), 7.46 (d, J=7.0 Hz, 1H), 7.40 (t, J=7.8 Hz, 1H), 7.33 (d, J=7.6 Hz, 1H), 2.24 (s, 2H). $^{13}$C-NMR (101 MHz, CDCl$_3$) δ 175.28, 166.9, 155.99, 149.43, 138.51, 133.44, 132.81, 132.54, 132.33, 130.97, 129.70, 129.30, 128.15, 127.53, 118.30, 18.32. HRMS: m/z calcd. for C$_{18}$H$_{13}$ClN$_3$OS [M+H]$^+$ 354.04624; found 354.04635.

Example 37: Preparation of 6-(o-Tolyl)-2-(p-tolylamino)thiazolo[4,5-d]pyrimidin-7(6H)-one (JWX-A0414)

1. Synthesis of 2-chloro-N-(2-methylphenyl)acetamide (D2)

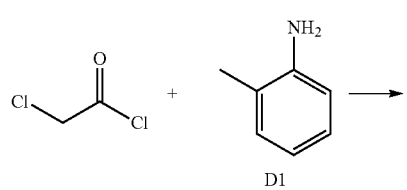

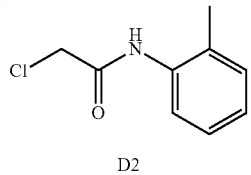

The title compound was prepared following the general procedure of A2. D2 was obtained as a white solid. Yield: 33.1%. The crude product was used in the next step without purification.

2. Synthesis of 4-amino-N-(2-methylphenyl)-2-(ethylthio)thiazole-5-carboxamide (D3)

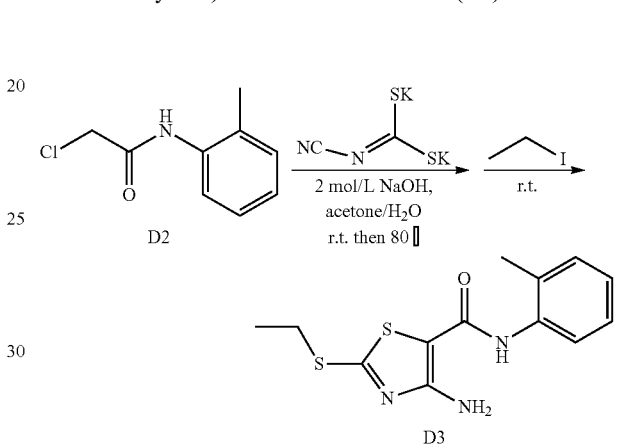

The title compound was prepared following the general procedure of A3. D3 was obtained as a white solid. Yield: 87.6%.

3. Synthesis of 6-(2-methylphenyl)-2-(ethylsulfonyl)thiazolo[4,5-d]pyrimidin-7(6H)-one (D5)

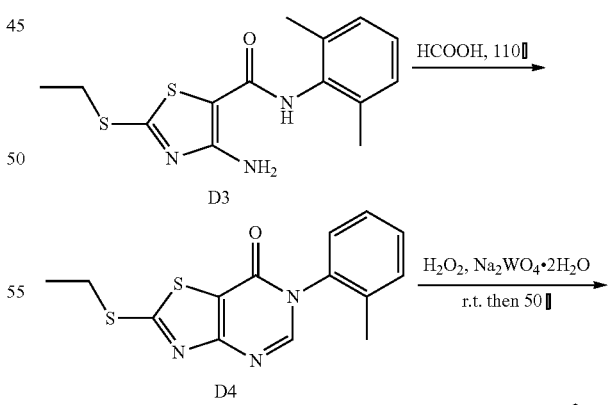

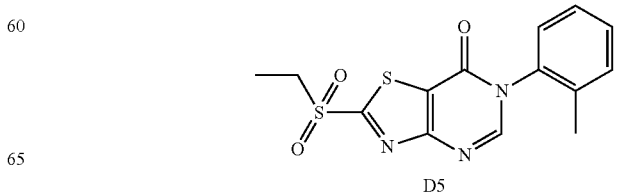

The title compound was prepared following the general procedure of A5. D5 was obtained as a white solid. Yield: 77.5%. The crude product was used in the next step without purification.

4. Synthesis of 6-(2-methylphenyl)-2-(p-tolylamino) thiazolo[4,5-d]pyrimidin-7(6H)-one (JWX-A0414)

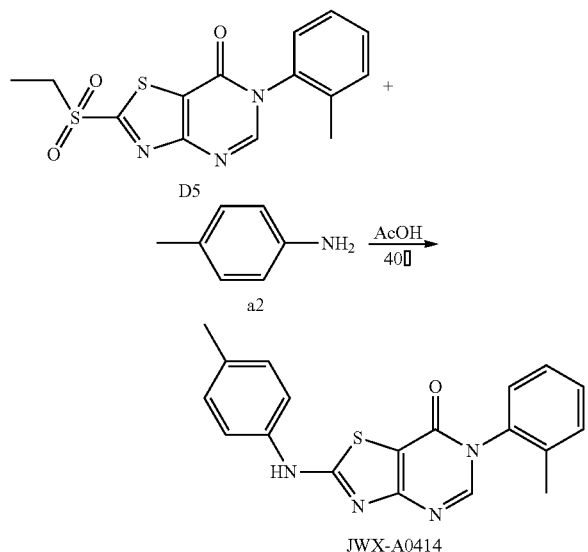

The title compound was prepared following the general procedure of JWX-A0824. JWX-A0414 was obtained as a white solid. Yield: 34.7%.

$^1$H-NMR (400 MHz, DMSO-$d_6$) δ 11.06 (s, 1H), 8.32 (s, 1H), 7.62 (d, J=8.2 Hz, 2H), 7.51-7.31 (m, 4H), 7.21 (d, J=8.2 Hz, 2H), 2.29 (s, 3H), 2.10 (s, 3H). $^{13}$C-NMR (101 MHz, DMSO-$d_6$) δ 167.70, 166.45, 155.81, 150.69, 137.63, 136.89, 136.05, 133.06, 131.23, 130.07, 129.96, 128.84, 127.47, 119.23, 108.15, 20.93, 17.67.

Example 38: Preparation of 6-(2-Chlorophenyl)-2-(p-tolylamino) thiazolo[4,5-d]pyrimidin-7(6H)-one (JWX-A0415)

1. Synthesis of 2-chloro-N-(2-chlorophenyl)acetamide (E2)

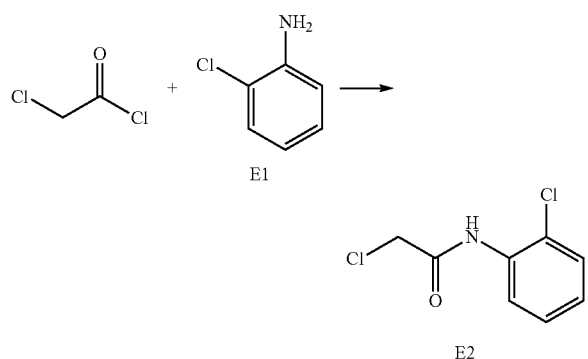

The title compound was prepared following the general procedure of A2. E2 was obtained as a white solid. Yield: 75.5%. The crude product was used in the next step without purification.

2. Synthesis of 4-amino-N-(2-chlorophenyl)-2-(ethylthio)thiazole-5-carboxamide (E3)

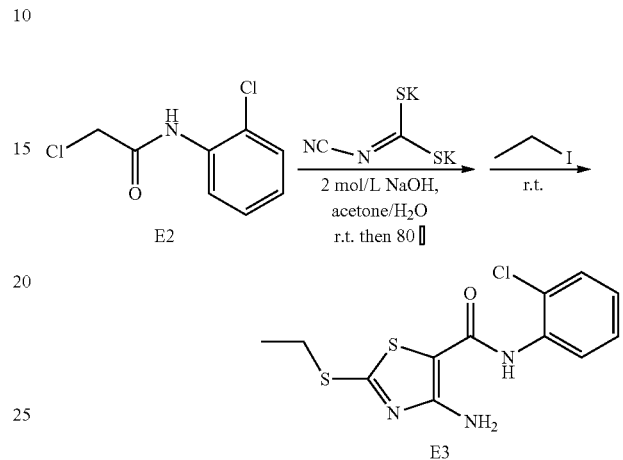

The title compound was prepared following the general procedure of A3. E3 was obtained as a yellow solid. Yield: 77.2%.

3. Synthesis of 6-(2-chlorophenyl)-2-(ethylsulfonyl) thiazolo[4,5-d]pyrimidin-7(6H)-one (E5)

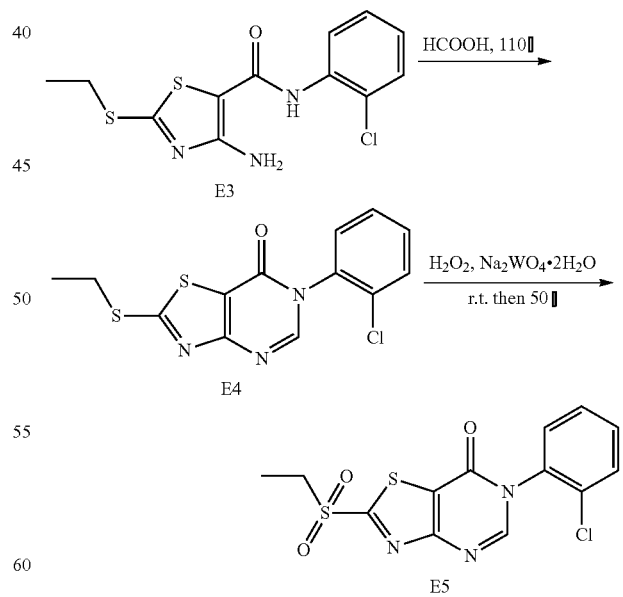

The title compound was prepared following the general procedure of A5. E5 was obtained as a yellow solid. Yield: 63.4%. The crude product was used in the next step without purification.

4. Synthesis of 6-(2-chlorophenyl)-2-(p-tolylamino)thiazolo[4,5-d]pyrimidin-7(6H)-one (JWX-A0415)

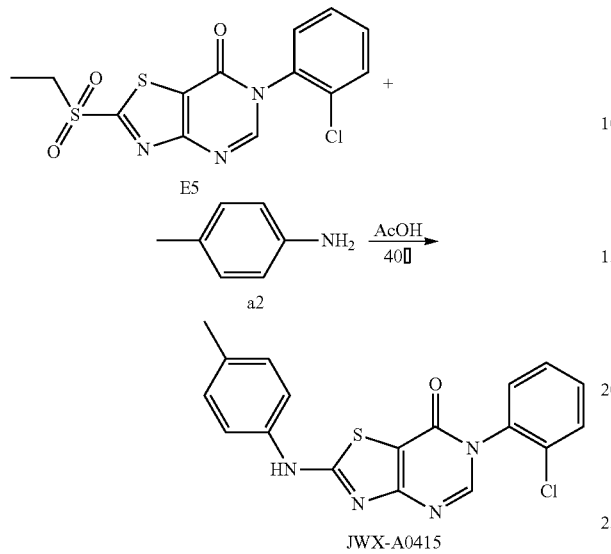

The title compound was prepared following the general procedure of JWX-A0824. JWX-A0415 was obtained as a yellow solid. Yield: 49.8%.

$^1$H-NMR (400 MHz, DMSO-d$_6$) δ 11.07 (s, 1H), 8.40 (s, 1H), 7.79-7.66 (m, 2H), 7.65-7.51 (m, 4H), 7.22 (d, J=8.1 Hz, 2H), 2.29 (s, 3H). $^{13}$C-NMR (101 MHz, DMSO-d$_6$) δ 167.85, 166.42, 155.50, 150.62, 137.55, 135.11, 133.17, 132.01, 131.80, 131.14, 130.48, 130.09, 128.82, 119.30, 107.92, 20.94.

Example 39: Preparation of 6-(2-Chloro-6-methylphenyl)-2-((2-fluorobenzyl)thio)thiazolo[4,5-d]pyrimidin-7(6H)-one (LYH150309-2F)

1. Synthesis of 4-amino-N-(2-chloro-6-methylphenyl)-2-((2-fluorobenzyl)thio)thiazole-5-carboxamide (A3-2)

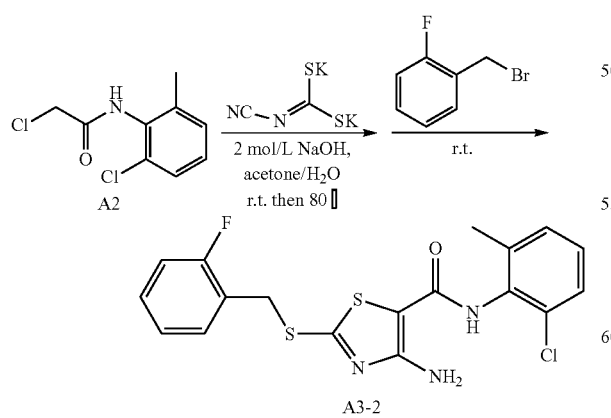

The title compound was prepared following the general procedure of A3-1. A3-1 was obtained as a yellow solid. Yield: 65.8%.

2. Synthesis of 6-(2-chloro-6-methylphenyl)-2-((2-fluorobenzyl)thio) thiazolo[4,5-d]pyrimidin-7(6H)-one (LYH150309-2F)

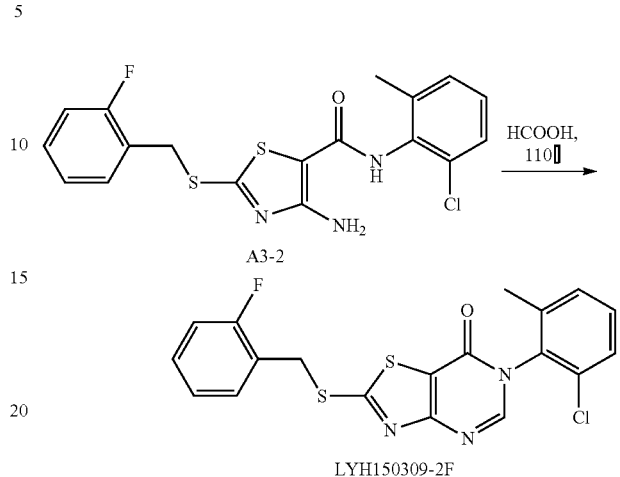

The title compound was prepared following the general procedure of JWX-A1223. LYH150309-2F was obtained as a yellow solid. Yield: 44.1%.

$^1$H-NMR (400 MHz, DMSO-d$_6$) δ 8.54 (s, 1H), 7.65 (td, J=7.7, 1.4 Hz, 1H), 7.58 (d, J=6.8 Hz, 1H), 7.55-7.44 (m, 2H), 7.39 (tt, J=5.2, 2.6 Hz, 1H), 7.32-7.18 (m, 2H), 4.74 (s, 2H), 2.13 (s, 3H). $^{13}$C-NMR (101 MHz, DMSO-d$_6$) δ 175.04, 166.18, 159.78, 155.08, 151.34, 139.06, 133.54, 132.16, 132.01, 131.97, 131.63, 130.82, 130.74, 130.34, 128.11, 125.20, 125.17, 123.36, 123.22, 116.97, 116.19, 115.98, 31.24, 18.13.

Example 40: Preparation of 6-(2-Chloro-6-methylphenyl)-2-((3-fluorobenzyl)thio)thiazolo[4,5-d]pyrimidin-7(6H)-one (LYH150310-3F)

1. Synthesis of 4-amino-N-(2-chloro-6-methylphenyl)-2-((3-fluorobenzyl)thio)thiazole-5-carboxamide (A3-3)

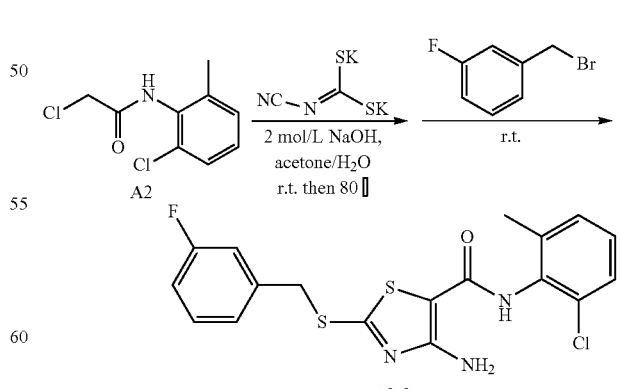

The title compound was prepared following the general procedure of A3-1. A3-3 was obtained as a yellow solid. Yield: 84.5%.

2. Synthesis of 6-(2-chloro-6-methylphenyl)-2-((3-fluorobenzyl)thio) thiazolo[4,5-d]pyrimidin-7(6H)-one (LYH150310-3F)

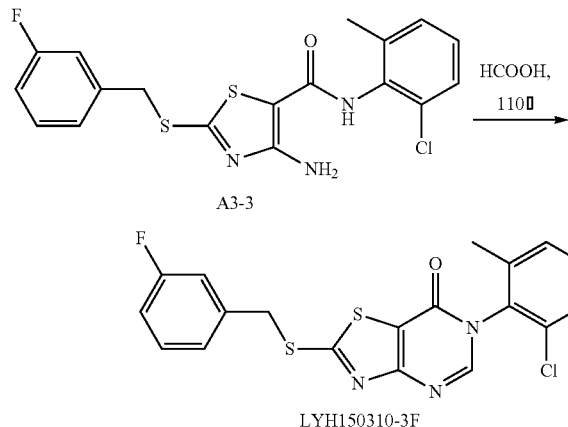

The title compound was prepared following the general procedure of JWX-A1223. LYH150310-3F was obtained as a yellow solid. Yield: 32.2%.

$^1$H-NMR (400 MHz, DMSO-$d_6$) δ 8.53 (s, 1H), 7.61-7.54 (m, 1H), 7.53-7.35 (m, 5H), 7.15 (ddd, J=9.4, 6.9, 2.1 Hz, 1H), 4.72 (s, 2H), 2.13 (s, 3H). $^{13}$C-NMR (101 MHz, DMSO-$d_6$) δ 175.39, 166.17, 163.75, 161.32, 155.06, 151.33, 139.41, 139.33, 139.06, 133.54, 132.17, 131.62, 131.15, 131.07, 130.33, 128.11, 125.77, 116.91, 116.51, 116.29, 115.27, 115.06, 36.79, 18.14.

Example 41: Preparation of 6-(2-Chloro-6-methylphenyl)-2-((4-fluorobenzyl)thio)thiazolo[4,5-d]pyrimidin-7(6H)-one (LYH150312-4F)

1. Synthesis of 4-amino-N-(2-chloro-6-methylphenyl)-2-((4-fluorobenzyl)thio)thiazole-5-carboxamide (A3-4)

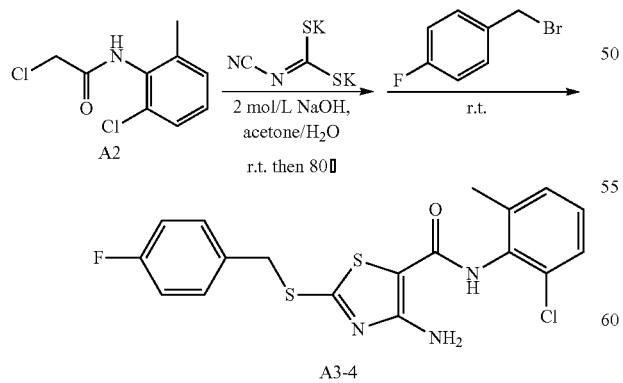

The title compound was prepared following the general procedure of A3-1. A3-4 was obtained as a yellow solid. Yield: 73.5%.

2. Synthesis of 6-(2-chloro-6-methylphenyl)-2-((4-fluorobenzyl)thio)thiazolo[4,5-d]pyrimidin-7(6H)-one (LYH150312-4F)

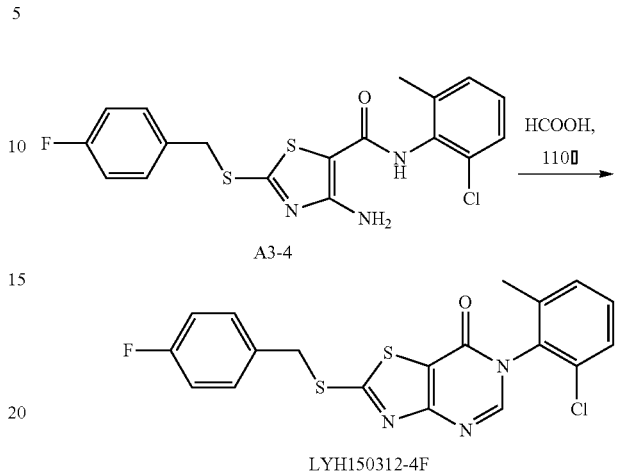

The title compound was prepared following the general procedure of JWX-A1223. LYH150312-4F was obtained as a yellow solid. Yield: 25.6%.

$^1$H-NMR (400 MHz, DMSO-$d_6$) δ 8.53 (s, 1H), 7.64-7.54 (min, 3H), 7.53-7.42 (min, 2H), 7.26-7.16 (min, 2H), 4.70 (s, 2H), 2.13 (s, 3H). $^{13}$C-NMR (101 MHz, DMSO-$d_6$) δ 175.55, 166.20, 163.34, 155.05, 151.31, 139.06, 133.55, 132.66, 132.63, 132.17, 131.77, 131.69, 131.62, 130.33, 128.11, 116.82, 116.08, 115.87, 36.65, 18.13.

Example 42: Preparation of 6-(2-Chloro-6-methylphenyl)-2-((4-methylbenzyl)thio)thiazolo[4,5-d]pyrimidin-7(6H)-one (LYH150318-4Me)

1. Synthesis of 4-amino-N-(2-chloro-6-methylphenyl)-2-((4-methylbenzyl)thio)thiazole-5-carboxamide (A3-5)

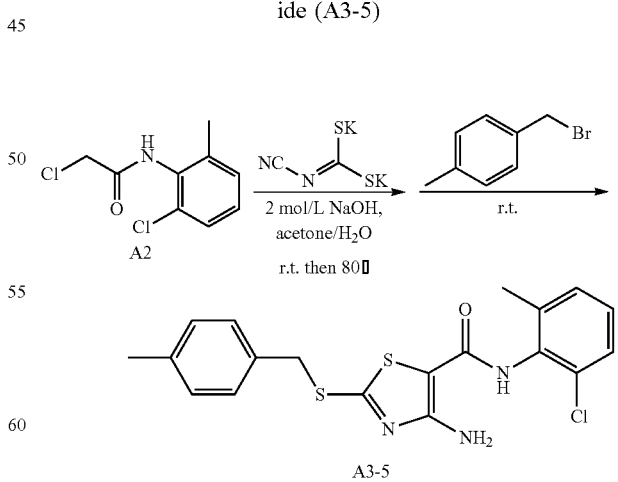

The title compound was prepared following the general procedure of A3-1. A3-5 was obtained as a yellow solid. Yield: 77.8%.

2. Synthesis of 6-(2-chloro-6-methylphenyl)-2-((4-methylbenzyl)thio)thiazolo[4,5-d]pyrimidin-7(6H)-one (LYH150318-4Me)

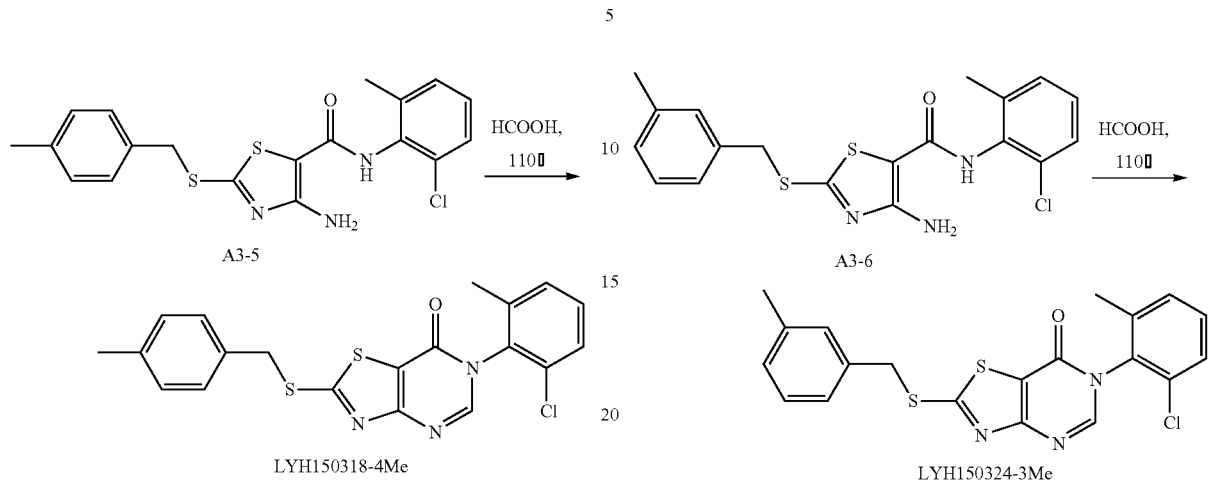

The title compound was prepared following the general procedure of JWX-A1223. LYH150318-4Me was obtained as a yellow solid. Yield: 63.8%.

$^{1}$H-NMR (400 MHz, DMSO-$d_6$) δ 8.52 (s, 1H), 7.62-7.56 (m, 1H), 7.54-7.39 (m, 4H), 7.18 (d, J=7.9 Hz, 2H), 4.65 (s, 2H), 2.28 (s, 3H), 2.12 (s, 3H). $^{13}$C-NMR (101 MHz, DMSO-$d_6$) δ 175.83, 175.75, 166.23, 155.04, 151.29, 139.05, 137.65, 133.55, 133.03, 132.17, 131.62, 130.33, 129.72, 129.56, 128.11, 116.71, 37.33, 21.19, 18.13.

Example 43: Preparation of 6-(2-Chloro-6-methyl-phenyl)-2-((3-methylbenzyl)thio)thiazolo[4,5-d]pyrimidin-7(6H)-one (LYH150324-3Me)

1. Synthesis of 4-amino-N-(2-chloro-6-methylphenyl)-2-((3-methylbenzyl)thio)thiazole-5-carboxamide (A3-6)

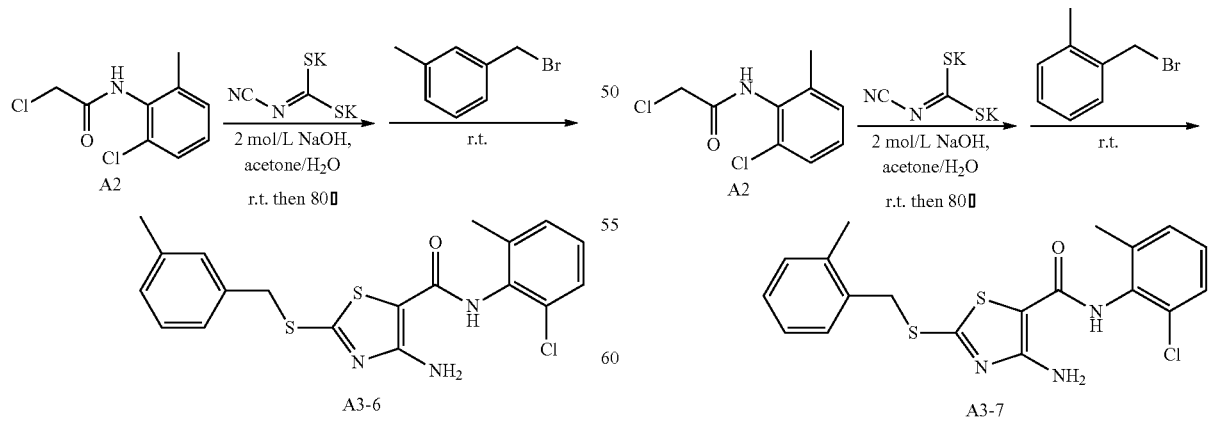

The title compound was prepared following the general procedure of A3-1. A3-6 was obtained as a yellow solid. Yield: 85.3%.

2. Synthesis of 6-(2-chloro-6-methylphenyl)-2-((3-methylbenzyl)thio)thiazolo[4,5-d]pyrimidin-7(6H)-one (LYH150324-3Me)

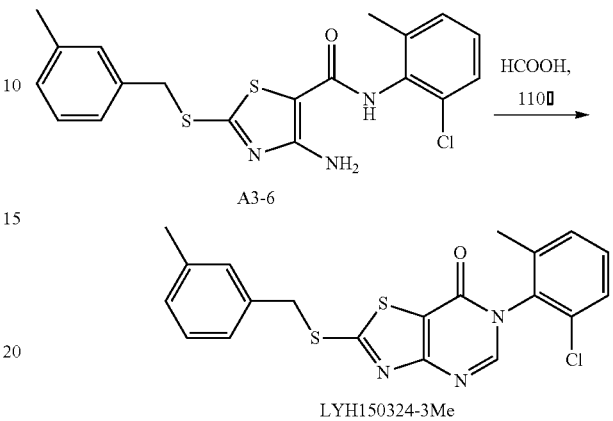

The title compound was prepared following the general procedure of JWX-A1223. LYH150324-3Me was obtained as a yellow solid. Yield: 30.2%.

$^{1}$H-NMR (400 MHz, DMSO-$d_6$) δ 8.52 (s, 1H), 7.58 (d, J=7.8 Hz, 1H), 7.47 (s, 1H), 7.33 (d, J=8.6 Hz, 2H), 7.27 (d, J=7.5 Hz, 1H), 7.13 (d, J=7.4 Hz, 1H), 4.65 (s, 2H), 2.30 (s, 3H), 2.12 (s, 3H). $^{13}$C-NMR (101 MHz, DMSO-$d_6$) δ 175.80, 166.23, 151.32, 139.05, 138.36, 135.97, 133.54, 130.12, 129.00, 128.10, 116.74, 21.41, 18.12.

Example 44: Preparation of 6-(2-Chloro-6-methyl-phenyl)-2-((2-methylbenzyl)thio)thiazolo[4,5-d]pyrimidin-7(6H)-one (LYH150325-2Me)

1. Synthesis of 4-amino-N-(2-chloro-6-methylphenyl)-2-((2-methylbenzyl)thio)thiazole-5-carboxamide (A3-7)

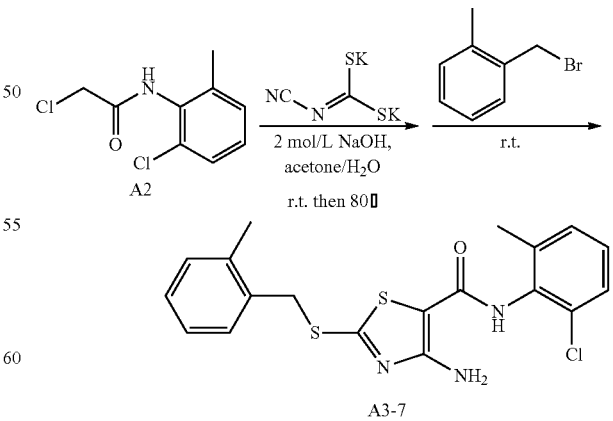

The title compound was prepared following the general procedure of A3-1. A3-7 was obtained as a yellow solid. Yield: 78.9%.

2. Synthesis of 6-(2-chloro-6-methylphenyl)-2-((2-methylbenzyl)thio)thiazolo[4,5-d]pyrimidin-7(6H)-one (LYH150325-2Me)

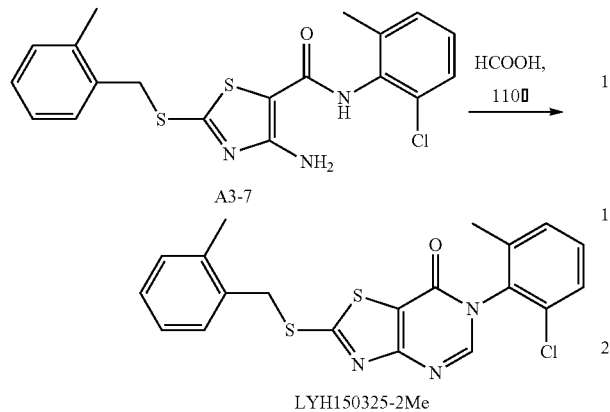

The title compound was prepared following the general procedure of JWX-A1223. LYH150325-2Me was obtained as a yellow solid. Yield: 63.9%.

$^1$H-NMR (400 MHz, DMSO-d$_6$) δ 8.54 (s, 1H), 7.58 (d, J=7.7 Hz, 1H), 7.55-7.44 (m, 3H), 7.28-7.17 (m, 3H), 4.71 (s, 2H), 2.42 (s, 3H), 2.13 (s, 3H). $^{13}$C-NMR (101 MHz, DMSO-d$_6$) δ 175.52, 166.23, 155.07, 151.32, 139.06, 137.49, 133.53, 132.16, 131.63, 131.02, 130.55, 130.34, 128.74, 128.11, 126.73, 116.81, 36.11, 19.32, 18.13.

Example 45: Preparation of 6-(2-Chloro-6-methylphenyl)-2-((4-methoxybenzyl)thio)thiazolo[4,5-d]pyrimidin-7(6H)-one (LYH150326-4OCH3)

1. Synthesis of 4-amino-N-(2-chloro-6-methylphenyl)-2-((4-methoxybenzyl)thio)thiazole-5-carboxamide (A3-8)

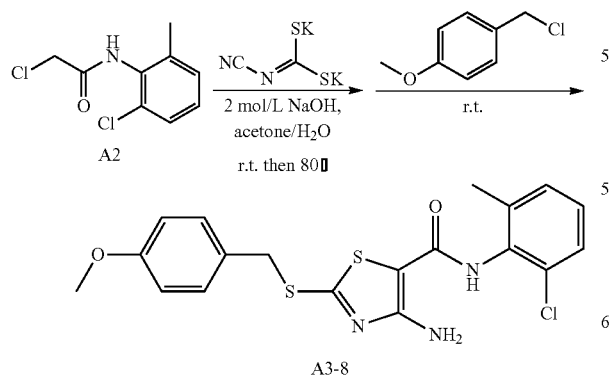

The title compound was prepared following the general procedure of A3-1. A3-8 was obtained as a yellow solid. Yield: 52.8%.

2. Synthesis of 6-(2-chloro-6-methylphenyl)-2-((4-methoxybenzyl)thio)thiazolo[4,5-d]pyrimidin-7(6H)-one (LYH150326-4OCH3)

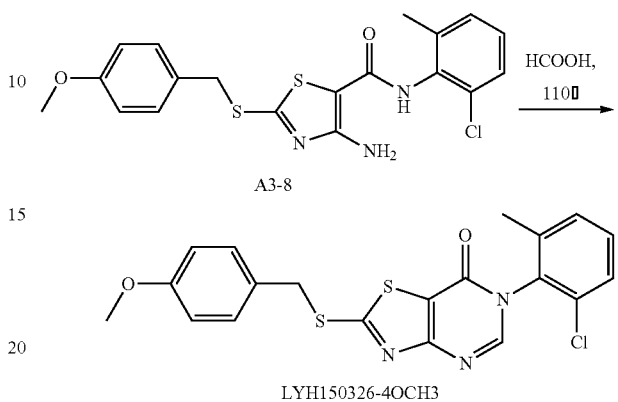

The title compound was prepared following the general procedure of JWX-A1223. LYH150326-4OCH3 was obtained as a yellow solid. Yield: 47.0%.

$^1$H-NMR (400 MHz, DMSO-d$_6$) δ 8.52 (s, 1H), 7.58 (d, J=7.2 Hz, 1H), 7.54-7.44 (m, 4H), 6.94 (d, J=8.6 Hz, 2H), 4.64 (s, 2H), 3.74 (s, 3H), 2.12 (s, 3H). $^{13}$C-NMR (101 MHz, DMSO-d$_6$) δ 175.87, 166.24, 159.38, 155.05, 151.30, 139.06, 133.57, 132.17, 131.62, 130.96, 130.34, 128.11, 127.79, 116.68, 114.57, 55.59, 37.17, 18.13.

Example 46: Preparation of 6-(2-Chloro-6-methylphenyl)-2-((4-(trifluoromethyl)benzyl)thio)thiazolo[4,5-d]pyrimidin-7(6H)-one (LYH150409-4CF3)

1. Synthesis of 4-amino-N-(2-chloro-6-methylphenyl)-2-((4-(trifluoromethyl)benzyl)thio)thiazole-5-carboxamide (A3-9)

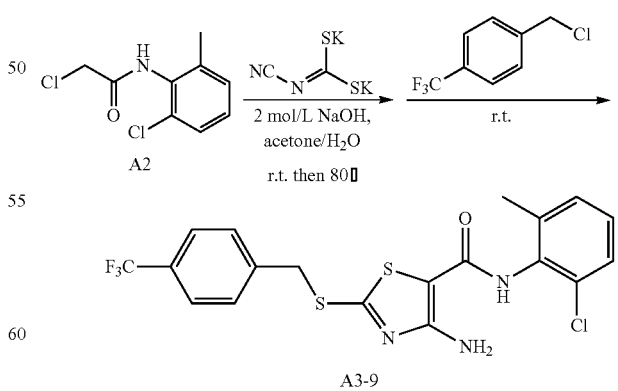

The title compound was prepared following the general procedure of A3-1. A3-9 was obtained as a yellow solid. Yield: 58.9%.

2. Synthesis of 6-(2-chloro-6-methylphenyl)-2-((4-(trifluoromethyl)benzyl)thio)thiazolo[4,5-d]pyrimidin-7(6H)-one (LYH150409-4CF3)

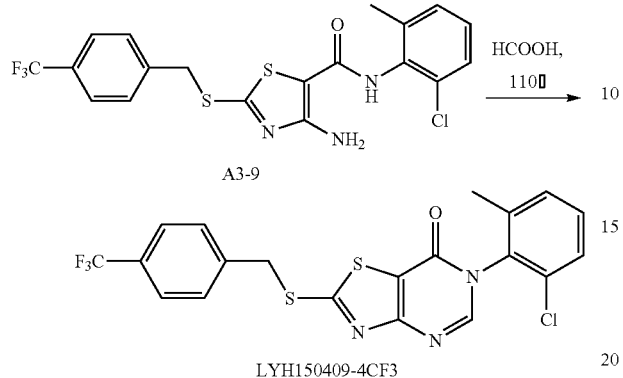

The title compound was prepared following the general procedure of JWX-A1223. LYH150409-4CF3 was obtained as a yellow solid. Yield: 52.4%.

$^1$H-NMR (400 MHz, DMSO-$d_6$) δ 8.53 (s, 1H), 7.77 (q, J=8.6 Hz, 4H), 7.58 (dd, J=7.8, 1.0 Hz, 1H), 7.54-7.43 (m, 2H), 4.80 (s, 2H), 2.12 (s, 3H). $^{13}$C-NMR (101 MHz, DMSO-$d_6$) δ 175.25, 166.17, 155.05, 151.35, 141.69, 139.06, 133.53, 132.16, 131.63, 130.42, 130.34, 128.11, 126.02, 125.98, 116.96, 36.70, 18.13.

Example 47: Preparation of 6-(2-Chloro-6-methylphenyl)-2-(o-tolylamino)thiazolo[4,5-d]pyrimidin-7(6H)-one (JWX-A0602)

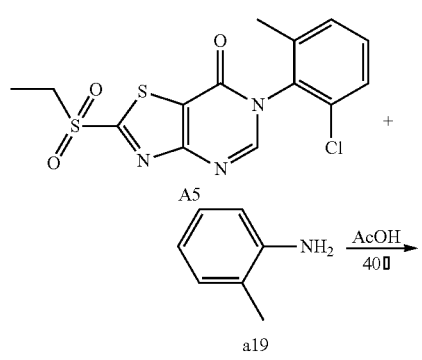

The title compound was prepared following the general procedure of JWX-A0824. JWX-A0602 was obtained as a white solid. Yield: 75.5%. m.p.: 268-270° C.

$^1$H-NMR (400 MHz, DMSO-$d_6$) δ 10.53 (s, 1H), 8.33 (s, 1H), 7.69 (d, J=7.8 Hz, 1H), 7.56 (dd, J=7.7, 1.2 Hz, 1H), 7.51-7.41 (m, 2H), 7.37-7.26 (m, 2H), 7.22 (dd, J=10.7, 4.0 Hz, 1H), 2.30 (s, 3H), 2.12 (s, 3H). $^{13}$C-NMR (101 MHz, DMSO-$d_6$) δ 171.28, 166.73, 155.03, 150.65, 139.11, 137.99, 134.09, 132.57, 132.33, 131.51, 131.34, 130.18, 128.03, 127.37, 126.92, 124.98, 107.91, 18.20, 18.17.

Example 48: Preparation of 6-(2-Chloro-6-methylphenyl)-2-((2-fluorophenyl)amino)thiazolo[4,5-d]pyrimidin-7(6H)-one (JWX-A0611)

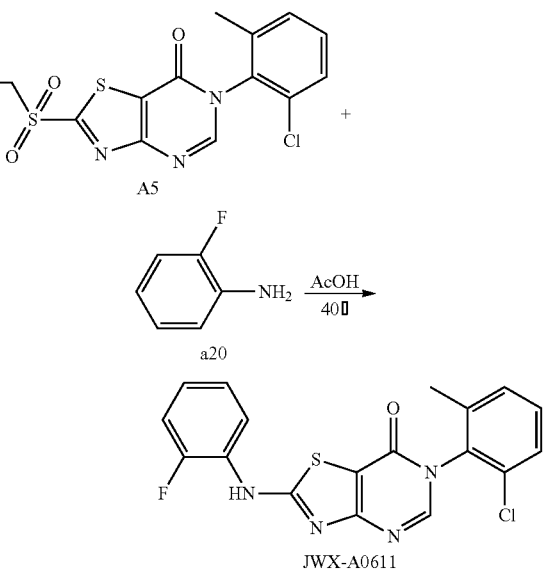

The title compound was prepared following the general procedure of JWX-A0824. JWX-A0611 was obtained as a white solid. Yield: 74.7%. m.p.: 181-183° C.

$^1$H-NMR (400 MHz, DMSO-$d_6$) δ 10.97 (s, 1H), 8.38 (s, 1H), 8.32 (dd, J=11.7, 4.5 Hz, 1H), 7.57 (dd, J=7.8, 1.3 Hz, 1H), 7.52-7.43 (m, 2H), 7.39-7.26 (m, 2H), 7.25-7.18 (m, 1H), 2.13 (s, 3H). $^{13}$C-NMR (101 MHz, DMSO-$d_6$) δ 168.77, 166.08, 155.20, 154.73, 152.29, 150.74, 139.09, 134.01, 132.29, 131.40, 130.22, 128.05, 125.84, 125.77, 125.38, 125.34, 123.16, 116.30, 116.11, 109.15, 18.16.

Example 49: Preparation of 6-(2-Chloro-6-methylphenyl)-2-((4-(trifluoromethoxy)phenyl)amino)thiazolo[4,5-d]pyrimidin-7(6H)-one (JWX-A-C0901)

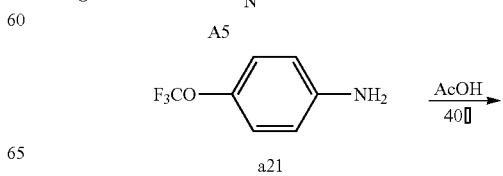

-continued

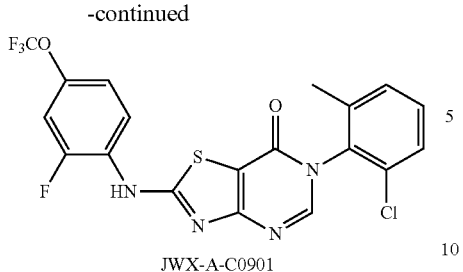

JWX-A-C0901

The title compound was prepared following the general procedure of JWX-A0824. JWX-A-C0901 was obtained as a white solid. Yield: 82.8%. m.p.: 213-215° C.

¹H-NMR (400 MHz, DMSO-d₆) δ 11.39 (s, 1H), 8.41 (s, 1H), 7.93-7.79 (m, 2H), 7.57 (dd, J=7.8, 1.4 Hz, 1H), 7.54-7.41 (m, 4H), 2.13 (s, 3H). ¹³C-NMR (101 MHz, DMSO-d₆) δ 167.56, 166.27, 155.18, 150.87, 144.02, 139.18, 139.10, 133.99, 132.29, 131.44, 130.25, 128.08, 122.63, 120.35, 108.77, 18.19.

Example 50: Preparation of 6-(2-Chloro-6-methylphenyl)-2-((3-(trifluoromethoxy)phenyl)amino)thiazolo[4,5-d]pyrimidin-7(6H)-one (JWX-A-C0907)

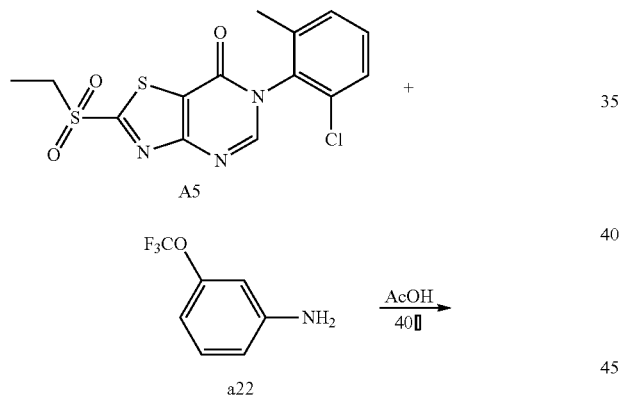

JWX-A-C0907

The title compound was prepared following the general procedure of JWX-A0824. JWX-A-C0907 was obtained as a white solid. Yield: 68.8%. m.p.: 247-249° C.

¹H-NMR (400 MHz, DMSO-d₆) δ 11.45 (s, 1H), 8.42 (s, 1H), 8.00 (s, 1H), 7.76-7.33 (m, 5H), 7.09 (d, J=8.0 Hz, 2H), 2.14 (s, 3H). ¹³C-NMR (101 MHz, DMSO-d₆) δ 167.36, 166.11, 155.19, 150.89, 149.30, 141.56, 139.08, 133.95, 132.27, 131.43, 131.38, 130.23, 128.06, 121.86, 119.31, 117.62, 115.55, 111.05, 18.15.

Example 51: Preparation of 6-(2-Chloro-6-methylphenyl)-2-((3,4-difluorophenyl)amino)thiazolo[4,5-d]pyrimidin-7(6H)-one (JWX-A-C0915)

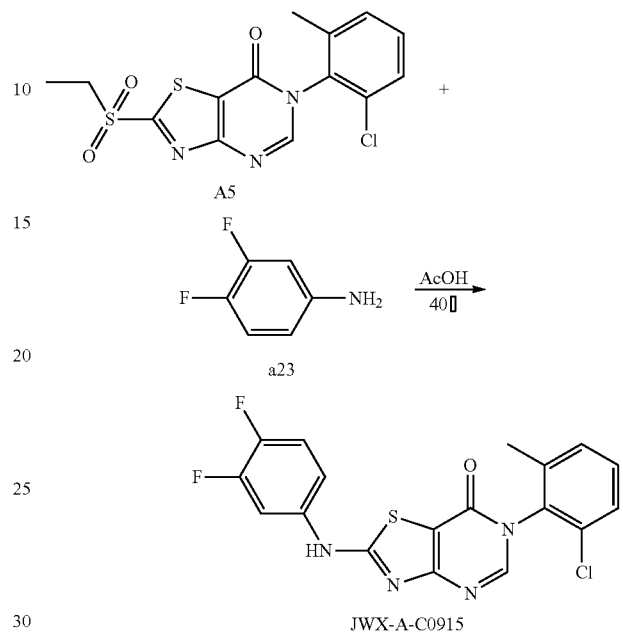

JWX-A-C0915

The title compound was prepared following the general procedure of JWX-A0824. JWX-A-C0915 was obtained as a white solid. Yield: 67.7%. m.p.: 255-258° C.

¹H-NMR (400 MHz, DMSO-d₆) δ 11.35 (s, 1H), 8.42 (s, 1H), 7.99 (ddd, J=12.9, 7.2, 2.5 Hz, 1H), 7.57 (dd, J=7.8, 1.3 Hz, 1H), 7.52-7.37 (m, 4H), 2.13 (s, 3H). ¹³C-NMR (101 MHz, DMSO-d₆) δ 167.45, 166.15, 155.15, 150.88, 148.50, 148.37, 146.99, 144.59, 144.46, 139.07, 133.95, 132.27, 131.42, 130.22, 128.06, 118.47, 118.29, 115.44, 108.76, 108.25, 108.04, 18.16.

Example 52: Preparation of 6-(2-Chloro-6-methylphenyl)-2-((3,5-dimethylphenyl)amino)thiazolo[4,5-d]pyrimidin-7(6H)-one (JWX-A-C1017)

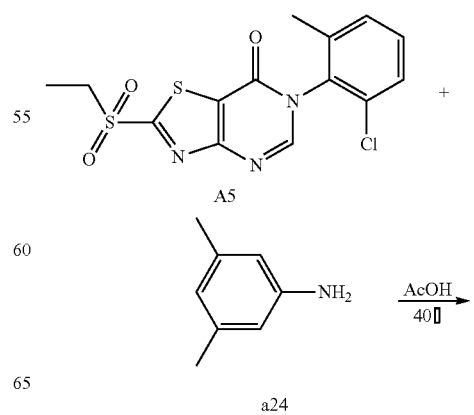

-continued

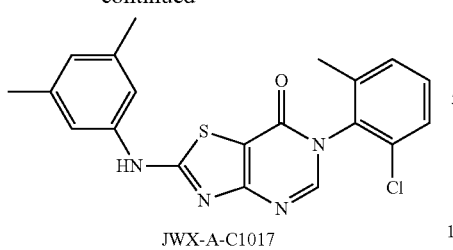

JWX-A-C1017

The title compound was prepared following the general procedure of JWX-A0824. JWX-A-C1017 was obtained as a white solid. Yield: 95.4%. m.p.: 152-154° C.

$^1$H-NMR (400 MHz, DMSO-$d_6$) δ 11.03 (s, 1H), 8.37 (s, 1H), 7.57 (d, J=7.6 Hz, 1H), 7.52-7.41 (m, 2H), 7.32 (s, 2H), 6.78 (s, 1H), 2.30 (s, 6H), 2.13 (s, 3H). $^{13}$C-NMR (101 MHz, DMSO-$d_6$) δ 168.05, 166.47, 155.11, 150.70, 139.84, 139.10, 138.87, 134.05, 132.31, 131.37, 130.20, 128.04, 125.78, 117.04, 108.08, 21.61, 18.16.

Example 53: Preparation of 6-(2-chloro-6-methylphenyl)-2-((3-chloro-4-fluorophenyl)amino)thiazolo[4,5-d]pyrimidin-7(6H)-one (JWX-A-C0104)

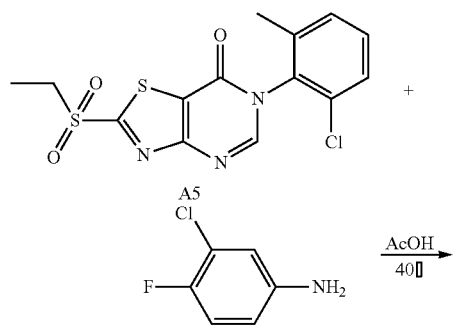

JWX-A-C0104

The title compound was prepared following the general procedure of JWX-A0824. JWX-A-C0104 was obtained as a white solid. Yield: 94.5%. m.p.: 265-267° C.

$^1$H-NMR (400 MHz, DMSO-$d_6$) δ 11.34 (s, 1H), 8.42 (s, 1H), 8.13 (dd, J=6.5, 2.4 Hz, 1H), 7.60-7.54 (m, 2H), 7.52-7.43 (m, 3H), 2.13 (s, 3H). $^{13}$C-NMR (101 MHz, DMSO-$d_6$) δ 167.47, 166.17, 155.17, 154.82, 152.40, 150.92, 139.09, 137.21, 133.96, 132.29, 131.46, 130.25, 128.08, 120.36, 120.19, 120.01, 119.46, 119.39, 117.99, 117.77, 108.84, 18.19.

Example 54: Preparation of N-(6-(2-Chloro-6-methylphenyl)-7-oxo-6,7-dihydrothiazolo[4,5-d]pyrimidin-2-yl)-4-methoxybenzamide (JWX-A0312)

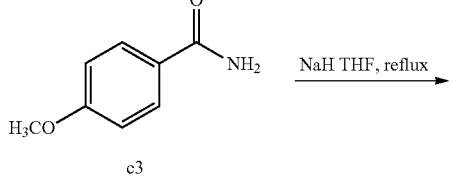

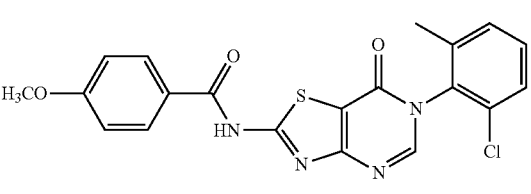 [SMILES: COc1ccc(C(=O)Nc2nc3ncn(-c4c(C)cccc4Cl)c(=O)c3s2)cc1]

JWX-A0312

The title compound was prepared following the general procedure of JWX-A0828. JWX-A0312 was obtained as a yellow solid. Yield: 74.4%. m.p.: 261-264° C.

$^1$H-NMR (400 MHz, DMSO-$d_6$) δ 13.29 (s, 1H), 8.47 (s, 1H), 8.17 (d, J=8.8 Hz, 2H), 7.61-7.40 (m, 3H), 7.09 (d, J=8.8 Hz, 2H), 3.85 (s, 3H), 2.15 (s, 3H). $^{13}$C-NMR (101 MHz, DMSO-$d_6$) δ 166.03, 165.08, 163.83, 163.77, 156.15, 150.89, 139.13, 133.98, 132.32, 131.43, 131.15, 130.24, 128.07, 123.52, 114.54, 111.64, 56.06, 18.19.

Example 55: Preparation of N-(6-(2-Chloro-6-methylphenyl)-7-oxo-6,7-dihydrothiazolo[4,5-d]pyrimidin-2-yl)-4-fluorobenzamide (JWX-A0617)

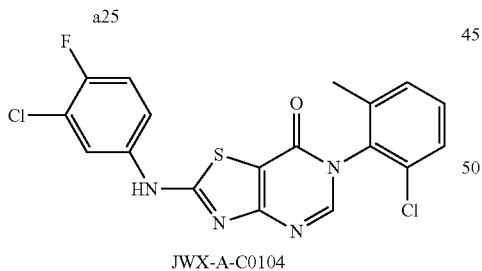

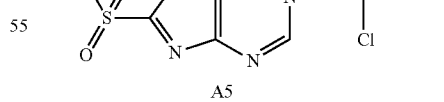

-continued

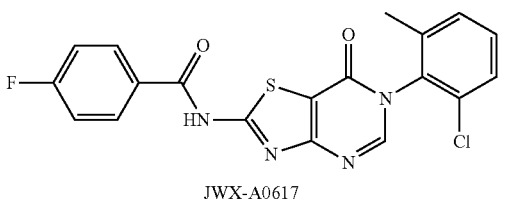

JWX-A0617

The title compound was prepared following the general procedure of JWX-A0828. JWX-A0617 was obtained as a white solid. Yield: 42.9%. m.p.: 335-337° C.

$^1$H-NMR (400 MHz, DMSO-d$_6$) δ 13.54 (s, 1H), 8.50 (s, 1H), 8.32-8.08 (m, 2H), 7.59 (d, J=7.3 Hz, 1H), 7.55-7.39 (m, 4H), 2.15 (s, 3H). $^{13}$C-NMR (101 MHz, DMSO-d$_6$) δ 165.80, 164.86, 163.74, 156.12, 151.07, 139.12, 133.93, 132.29, 132.02, 131.93, 131.50, 130.28, 128.10, 116.49, 116.27, 111.74, 18.19.

Example 56: Preparation of N-(6-(2-Chloro-6-methylphenyl)-7-oxo-6,7-dihydrothiazolo[4,5-d]pyrimidin-2-yl)-4-chlorobenzamide (JWX-A-C1020)

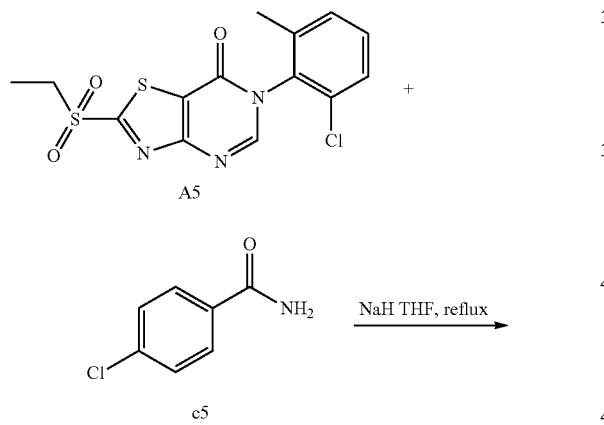

JWX-A-C1020

The title compound was prepared following the general procedure of JWX-A0828. JWX-A-C1020 was obtained as a white solid. Yield: 33.6%. m.p.: 312-314° C.

$^1$H-NMR (400 MHz, DMSO-d$_6$) δ 13.60 (s, 1H), 8.50 (s, 1H), 8.18 (d, J=8.6 Hz, 2H), 7.67 (d, J=8.6 Hz, 2H), 7.59 (dd, J=7.8, 1.3 Hz, 1H), 7.50 (dt, J=7.5, 7.1 Hz, 2H), 2.15 (s, 3H). $^{13}$C-NMR (101 MHz, DMSO-d$_6$) δ 165.95, 164.79, 163.74, 156.11, 151.10, 139.12, 138.79, 133.93, 132.29, 131.50, 130.90, 130.43, 130.29, 129.39, 128.10, 111.79, 18.19.

Example 57: Preparation of N-(6-(2-chloro-6-methylphenyl)-7-oxo-6,7-dihydrothiazolo[4,5-d]pyrimidin-2-yl)-4-bromobenzamide (JWX-A-C1122)

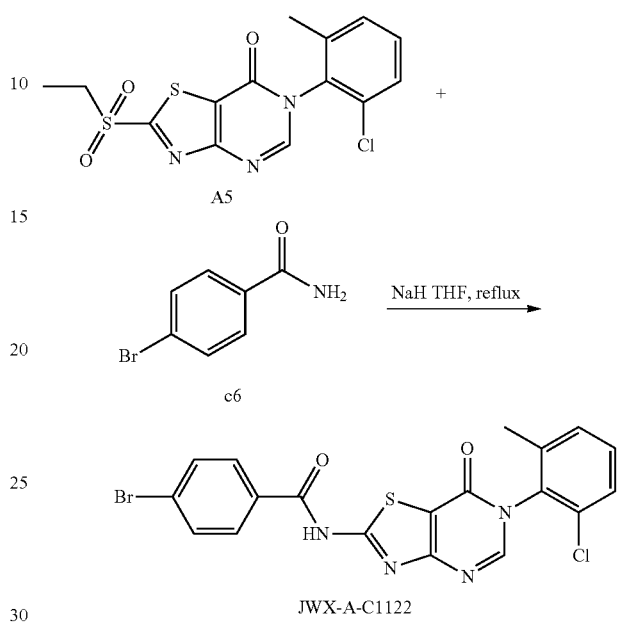

JWX-A-C1122

The title compound was prepared following the general procedure of JWX-A0828. JWX-A-C1122 was obtained as a white solid. Yield: 59.5%. m.p.: 335-337° C.

$^1$H-NMR (400 MHz, DMSO-d$_6$) δ 13.58 (s, 1H), 8.50 (s, 1H), 8.10 (d, J=7.7 Hz, 2H), 7.81 (d, J=7.6 Hz, 2H), 7.59 (d, J=6.8 Hz, 1H), 7.54-7.39 (m, 2H), 2.15 (s, 3H). $^{13}$C-NMR (101 MHz, DMSO-d$_6$) δ 166.12, 164.77, 163.74, 156.11, 151.08, 139.12, 133.93, 132.32, 131.49, 130.99, 130.80, 130.28, 128.09, 127.91, 110.00, 18.19.

Example 58: Preparation of N-(6-(2-Chloro-6-methylphenyl)-7-oxo-6,7-dihydrothiazolo[4,5-d]pyrimidin-2-yl)-4-(trifluoromethyl)benzamide (JWX-A-C1128)

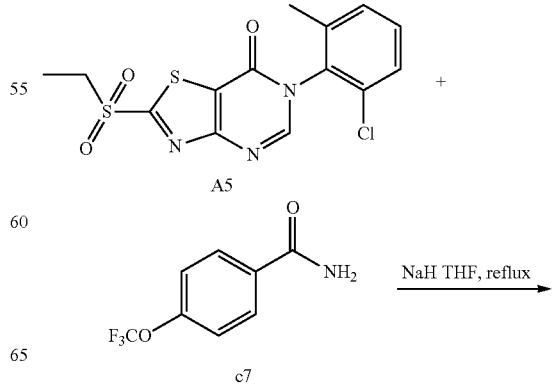

53

-continued

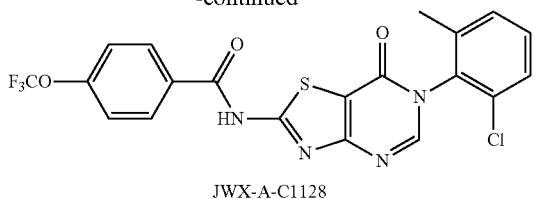

JWX-A-C1128

The title compound was prepared following the general procedure of JWX-A0828. JWX-A-C1128 was obtained as a white solid. Yield: 87.3%. m.p.: 282-285° C.

$^1$H-NMR (400 MHz, DMSO-$d_6$) δ 13.77 (s, 1H), 8.51 (s, 1H), 8.35 (d, J=7.4 Hz, 2H), 7.97 (d, J=7.3 Hz, 2H), 7.59 (d, J=7.1 Hz, 1H), 7.55-7.43 (m, 2H), 2.15 (s, 3H). $^{13}$C-NMR (101 MHz, DMSO-$d_6$) δ 165.98, 164.74, 163.70, 156.16, 151.17, 139.16, 135.51, 133.95, 133.68, 133.36, 133.04, 132.73, 132.33, 131.54, 130.33, 129.97, 128.14, 126.19, 125.58, 122.87, 111.93, 18.23.

Example 59: Preparation of N-(6-(2-Chloro-6-methylphenyl)-7-oxo-6,7-dihydrothiazolo[4,5-d]pyrimidin-2-yl)-4-(trifluoromethoxy)benzamide (JWX-A-C1205)

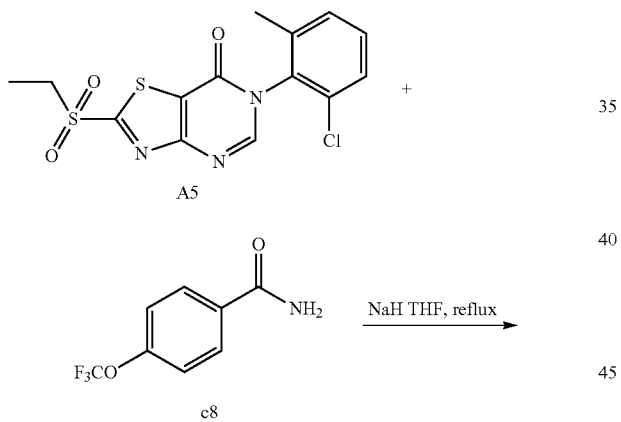

JWX-A-C1205

The title compound was prepared following the general procedure of JWX-A0828. JWX-A-C1205 was obtained as a white solid. Yield: 73.6%. m.p.: 134-136° C.

$^1$H-NMR (400 MHz, DMSO-$d_6$) δ 13.64 (s, 1H), 8.51 (s, 1H), 8.30 (d, J=8.8 Hz, 2H), 7.58 (dd, J=6.7, 4.7 Hz, 3H), 7.53-7.45 (m, 2H), 2.15 (s, 3H). $^{13}$C-NMR (101 MHz, DMSO-$d_6$) δ 165.70, 164.81, 163.77, 156.17, 152.15, 151.13, 139.18, 133.98, 132.35, 131.59, 131.53, 130.63, 130.32, 128.14, 121.71, 121.31, 119.15, 111.88, 18.22.

54

Example 60: Preparation of 6-(o-tolyl)-2-((3-fluoro-4-methylphenyl)amino)-thiazolo[4,5-d]pyrimidin-7(6H)-one (JWX-A-C1026)

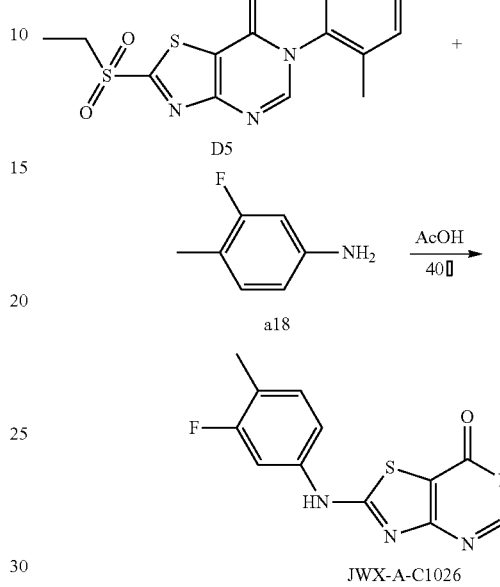

JWX-A-C1026

The title compound was prepared following the general procedure of JWX-A0824. JWX-A-C1026 was obtained as a yellow solid. Yield: 47.8%. m.p.: 252-254° C.

$^1$H-NMR (400 MHz, DMSO-$d_6$) δ 11.20 (s, 1H), 8.35 (s, 1H), 7.75 (d, J=12.7 Hz, 1H), 7.50-7.36 (m, 4H), 7.30 (s, 2H), 2.21 (s, 3H), 2.10 (s, 3H). $^{13}$C-NMR (101 MHz, DMSO-$d_6$) δ 167.14, 166.17, 159.78, 155.85, 150.84, 139.38, 139.27, 136.83, 136.02, 132.34, 132.27, 131.24, 130.01, 128.84, 127.49, 119.11, 118.93, 114.58, 108.61, 105.88, 105.61, 17.64, 14.14.

Example 61: Preparation of 6-(2-Chlorophenyl)-2-((3-fluoro-4-methylphenyl)amino)thiazolo[4,5-d]pyrimidin-7(6H)-one (JWX-A-C0831)

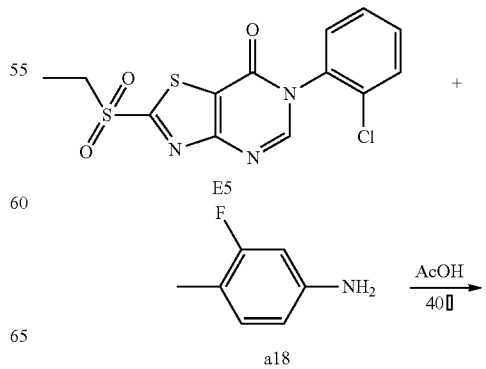

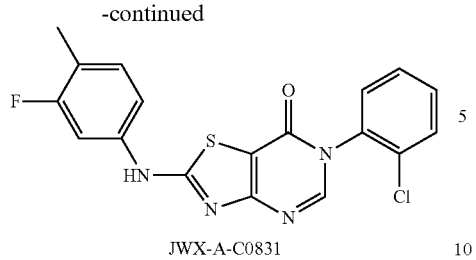

JWX-A-C0831

The title compound was prepared following the general procedure of JWX-A0824. JWX-A-C0831 was obtained as a white solid. Yield: 72.4%. m.p.: 251-253° C.

$^{1}$H-NMR (400 MHz, DMSO-d$_{6}$) δ 11.23 (s, 1H), 8.43 (s, 1H), 7.72 (dd, J=15.6, 8.1 Hz, 3H), 7.64-7.52 (m, 2H), 7.30 (s, 2H), 2.22 (s, 3H). $^{13}$C-NMR (101 MHz, DMSO-d$_{6}$) δ 167.32, 166.14, 162.17, 159.78, 155.53, 150.76, 139.32, 139.22, 135.04, 132.37, 132.30, 131.97, 131.84, 131.12, 130.48, 128.84, 119.23, 119.06, 114.70, 108.40, 105.98, 105.71, 14.14.

Example 62: Preparation of 6-(2-Bromo-6-methylphenyl)-2-((3-fluoro-4-methylphenyl)amino)thiazolo[4,5-d]pyrimidin-7(6H)-one (JWX-A-C0106)

1. Synthesis of 2-chloro-N-(2-bromo-6-methylphenyl)acetamide (F2)

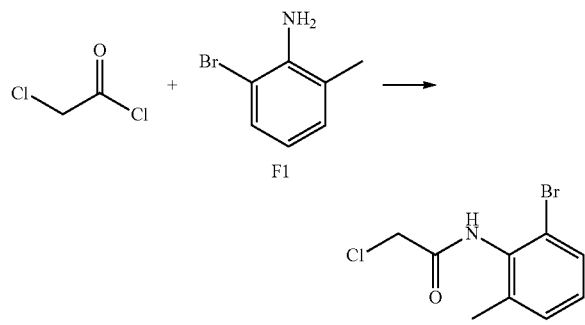

The title compound was prepared following the general procedure of A2. F2 was obtained as a white solid. Yield: 50.3%. The crude product was used in the next step without purification.

2. Synthesis of 4-amino-N-(2-bromo-6-methylphenyl)-2-(ethylthio)thiazole-5-carboxamide (F3)

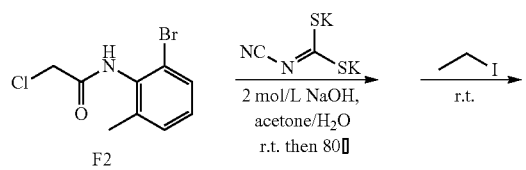

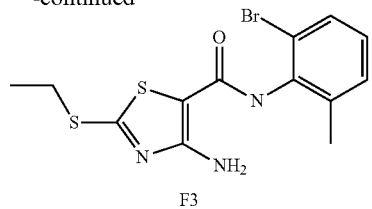

The title compound was prepared following the general procedure of A3. F3 was obtained as a yellow solid. Yield: 80.4%.

3. Synthesis of 6-(2-bromo-6-methylphenyl)-2-(ethylsulfonyl)thiazolo[4,5-d]pyrimidin-7(6H)-one (F5)

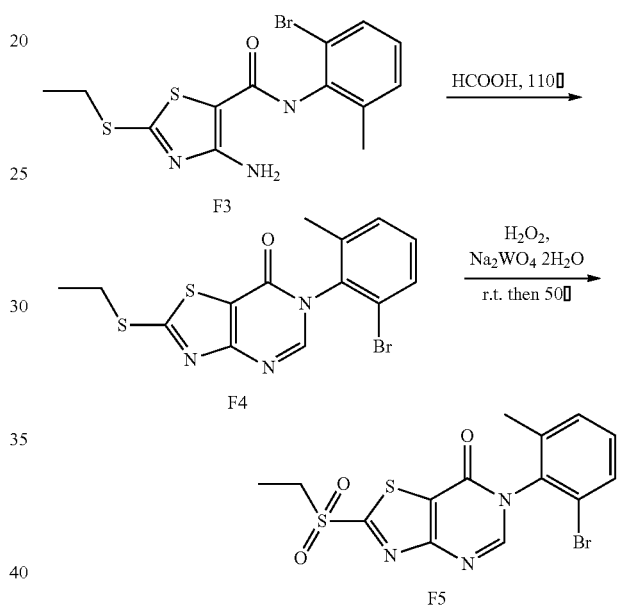

The title compound was prepared following the general procedure of A5. F5 was obtained as a white solid. Yield: 69.9%. The crude product was used in the next step without purification.

4. Synthesis of 6-(2-bromo-6-methylphenyl)-2-((3-fluoro-4-methylphenyl)amino)thiazolo[4,5-d]pyrimidin-7(6H)-one (JWX-A-C0106)

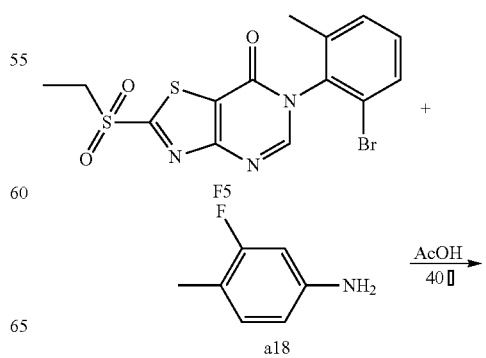

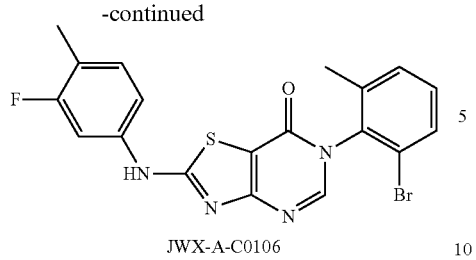

JWX-A-C0106

The title compound was prepared following the general procedure of JWX-A0824. JWX-A-C0106 was obtained as a white solid. Yield: 65.8%. m.p.: 262-264° C.

$^1$H-NMR (400 MHz, DMSO-$d_6$) δ 11.27 (s, 1H), 8.39 (s, 1H), 7.73 (dd, J=16.2, 10.1 Hz, 2H), 7.48 (d, J=7.4 Hz, 1H), 7.41 (t, J=7.8 Hz, 1H), 7.30 (s, 2H), 2.22 (s, 3H), 2.14 (s, 3H). $^{13}$C-NMR (101 MHz, DMSO-$d_6$) δ 167.45, 166.32, 162.20, 159.80, 155.11, 150.88, 139.32, 139.21, 139.14, 135.56, 132.40, 132.34, 131.78, 131.24, 130.80, 123.01, 119.31, 119.13, 114.76, 108.59, 106.03, 105.76, 18.51, 14.18.

Example 63: Preparation of 6-(2-fluoro-6-methylphenyl)-2-((3-fluoro-4-methylphenyl)amino)thiazolo[4,5-d]pyrimidin-7(6H)-one (JWX-A-C0111)

1. Synthesis of 2-chloro-N-(2-fluoro-6-methylphenyl)acetamide (G2)

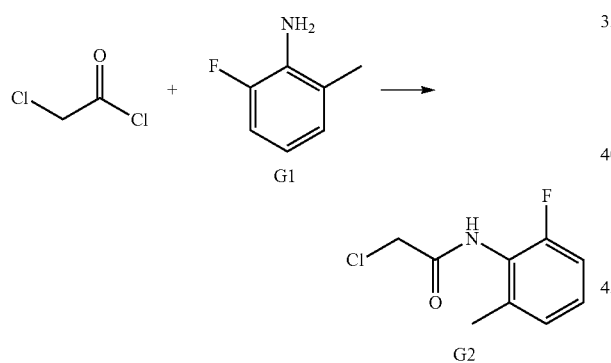

The title compound was prepared following the general procedure of A2. G2 was obtained as a white solid. Yield: 95.0%. The crude product was used in the next step without purification.

2. Synthesis of 4-amino-N-(2-fluoro-6-methylphenyl)-2-(ethylthio)thiazole-5-carboxamide (G3)

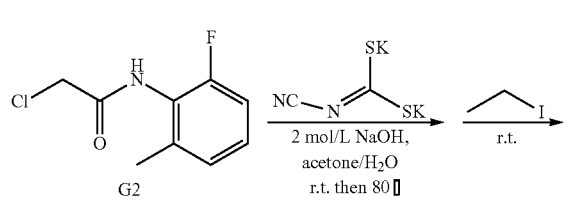

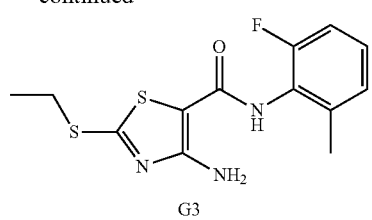

The title compound was prepared following the general procedure of A3. G3 was obtained as a yellow solid. Yield: 63.2%.

3. Synthesis of 6-(2-fluoro-6-methylphenyl)-2-(ethylsulfonyl)thiazolo[4,5-d]pyrimidin-7(6H)-one (G5)

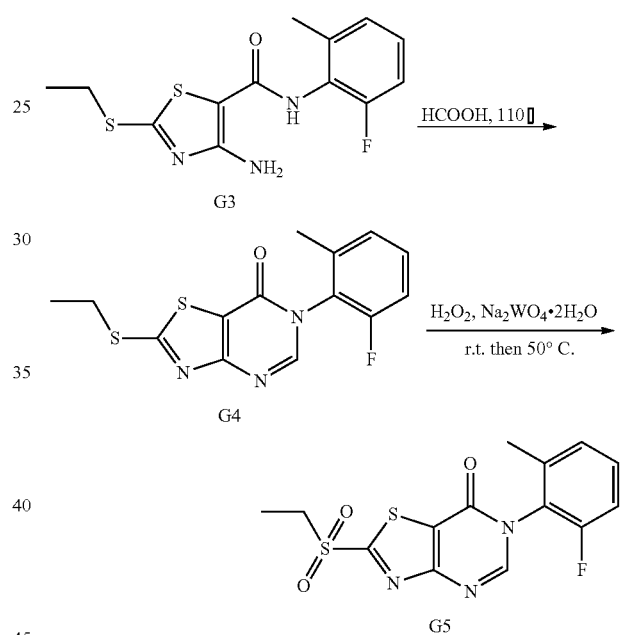

The title compound was prepared following the general procedure of A5. G5 was obtained as a white solid. Yield: 78.6%. The crude product was used in the next step without purification.

4. Synthesis of 6-(2-fluoro-6-methylphenyl)-2-((3-fluoro-4-methylphenyl)amino)thiazolo[4,5-d]pyrimidin-7(6H)-one (JWX-A-C0111)

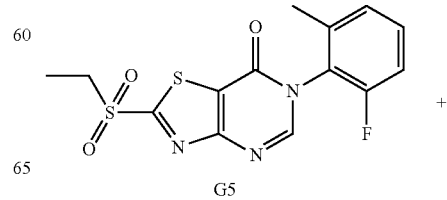

-continued

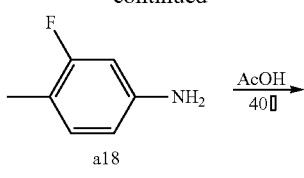

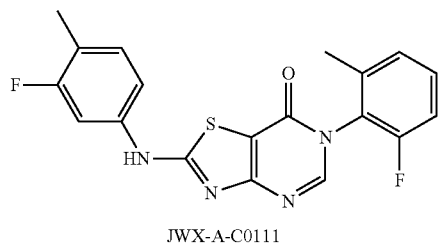

JWX-A-C0111

The title compound was prepared following the general procedure of JWX-A0824. JWX-A-C0111 was obtained as a white solid. Yield: 92.9%. m.p.: 260-263° C.

$^1$H-NMR (400 MHz, DMSO-$d_6$) δ 11.27 (s, 1H), 8.48 (s, 1H), 7.74 (d, J=12.0 Hz, 1H), 7.51 (dd, J=13.6, 7.5 Hz, 1H), 7.36-7.26 (m, 4H), 2.21 (s, 3H), 2.14 (s, 3H). $^{13}$C-NMR (101 MHz, DMSO-$d_6$) δ 167.47, 166.27, 162.20, 159.80, 159.32, 156.85, 155.33, 151.07, 139.32, 139.21, 138.97, 132.38, 132.32, 131.61, 131.53, 127.00, 124.28, 124.14, 119.29, 119.11, 114.73, 114.37, 114.17, 108.52, 106.01, 105.74, 17.43, 14.17.

Example 64: Preparation of 6-(2-Chloro-4-methylphenyl)-2-((3-fluoro-4-methylphenyl)amino)thiazolo[4,5-d]pyrimidin-7(6H)-one (JWX-A-C0229)

1. Synthesis of 2-chloro-N-(2-chloro-4-methylphenyl)acetamide (H2)

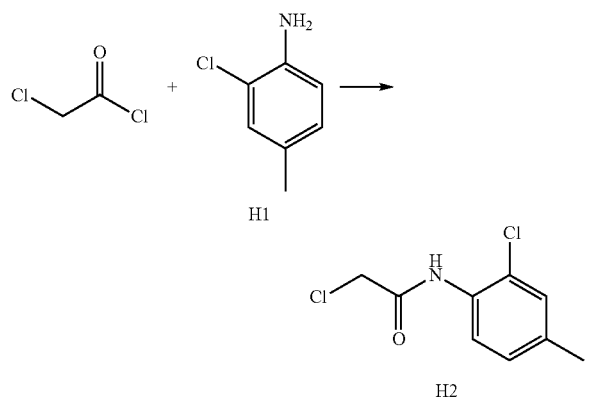

The title compound was prepared following the general procedure of A2. H2 was obtained as a white solid. Yield: 83.3%. The crude product was used in the next step without purification.

2. Synthesis of 4-amino-N-(2-chloro-4-methylphenyl)-2-(ethylthio)thiazole-5-carboxamide (H3)

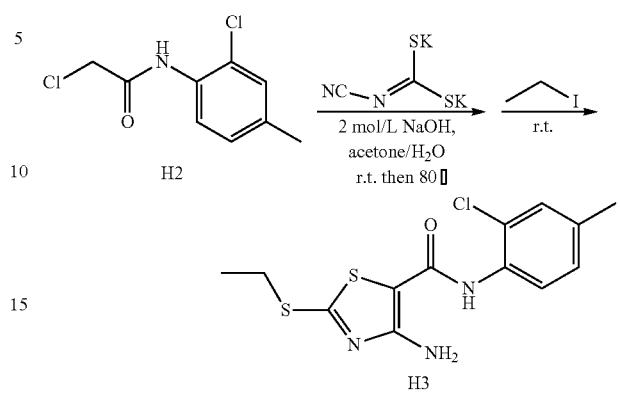

The title compound was prepared following the general procedure of A3. H3 was obtained as a yellow solid. Yield: 82.3%.

3. Synthesis of 6-(2-chloro-4-methylphenyl)-2-(ethylsulfonyl)thiazolo[4,5-d]pyrimidin-7(6H)-one (H5)

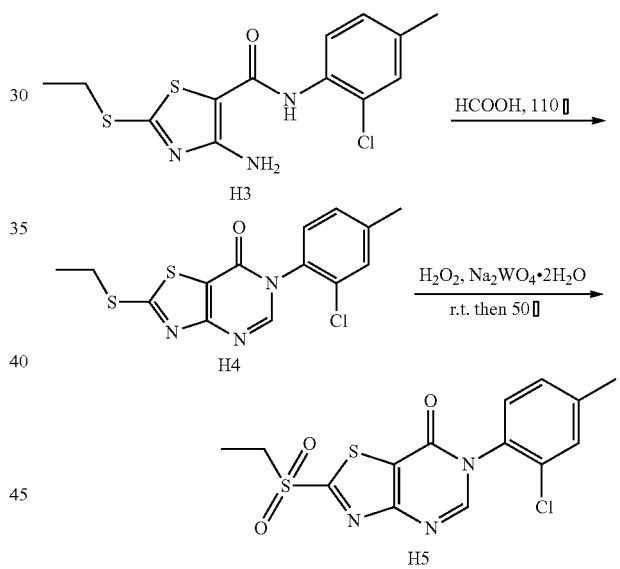

The title compound was prepared following the general procedure of A5. H5 was obtained as a white solid. Yield: 63.8%. The crude product was used in the next step without purification.

4. Synthesis of 6-(2-chloro-4-methylphenyl)-2-((3-fluoro-4-methylphenyl)amino)thiazolo[4,5-d]pyrimidin-7(6H)-one (JWX-A-C0229)

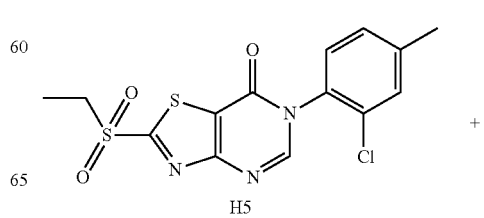

-continued

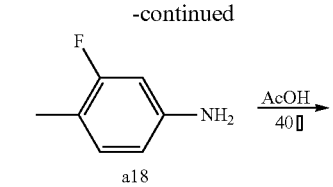

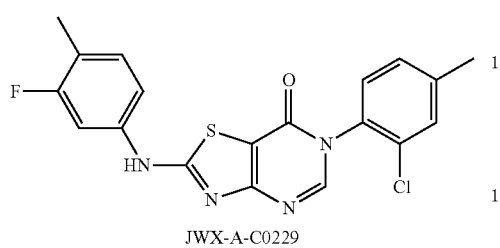

JWX-A-C0229

The title compound was prepared following the general procedure of JWX-A0824. JWX-A-C0229 was obtained as a white solid. Yield: 64.4%. m.p.: 254-256° C.

Example 65: Preparation of 6-(2-Chloro-6-methylphenyl)-2-(phenylthio)thiazolo[4,5-d]pyrimidin-7(6H)-one (LYH151120)

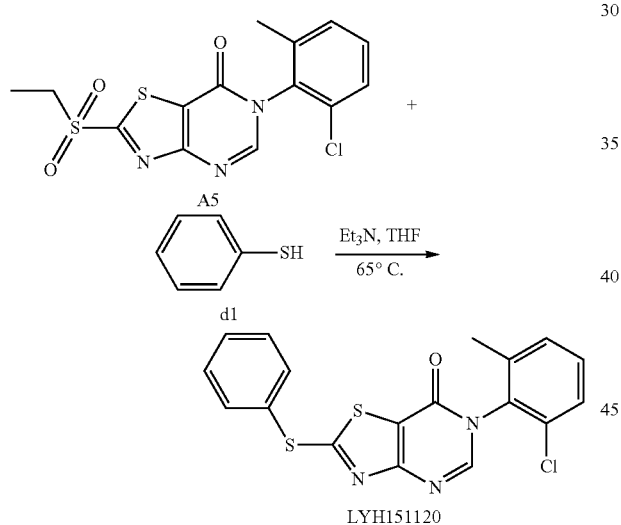

LYH151120

Compound A5 (738 mg, 2.0 mmol) was dissolved in THF (10 mL). Then, benzenethiol (330 mg, 3.0 mmol) and Et$_3$N (2 mL) were added to the solution successively. The reaction was refluxed at 65° C. for 6 h. The reaction mixture was concentrated and purified by silica gel chromatography (petroleum ether:EtOAc=10:1) to afford the compound LYH151120 as a white solid. Yield: 51.6%.

$^1$H-NMR (400 MHz, CDCl$_3$) δ 7.94 (s, 1H), 7.78 (d, J=6.7 Hz, 2H), 7.64-7.52 (m, 3H), 7.43 (d, J=7.3 Hz, 1H), 7.37 (t, J=7.8 Hz, 1H), 2.18 (s, 3H). $^{13}$C-NMR (101 MHz, CDCl$_3$) δ 180.44, 166.82, 155.04, 149.35, 138.44, 135.86, 133.37, 132.73, 131.55, 130.91, 130.58, 129.65, 128.31, 128.10, 77.38, 77.07, 76.75, 18.21. HRMS: m/z calcd. for C$_{18}$H$_{13}$ClN$_3$OS$_2$ [M+H]$^+$ 386.0183; found 386.0197.

Example 66: Preparation of 6-(2-Chloro-6-methylphenyl)-2-((3-fluorophenyl)thio)thiazolo[4,5-d]pyrimidin-7(6H)-one (LYH151215)

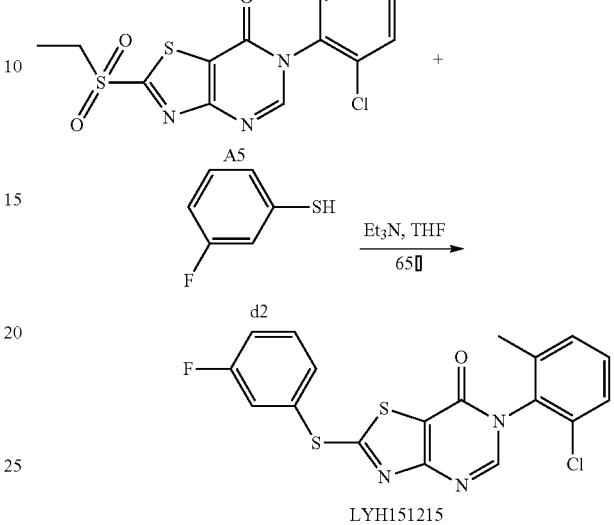

LYH151215

The title compound was prepared following the general procedure of LYH151120. LYH151215 was obtained as a white solid. Yield: 76.7%.

$^1$H-NMR (400 MHz, CDCl$_3$) δ 7.95 (s, 1H), 7.60-7.47 (m, 3H), 7.45-7.34 (m, 2H), 7.33-7.26 (m, 2H), 2.17 (s, 3H). $^{13}$C-NMR (101 MHz, CDCl$_3$) δ 178.56, 166.70, 164.36, 161.86, 155.00, 149.47, 138.42, 133.28, 132.70, 131.92, 131.84, 131.44, 131.40, 130.97, 129.90, 129.82, 129.68, 128.13, 122.67, 122.44, 118.87, 118.66, 77.38, 77.07, 76.75, 18.23.

Example 67: Preparation of 6-(2-Chloro-6-methylphenyl)-2-((4-fluorophenyl)thio)thiazolo[4,5-d]pyrimidin-7(6H)-one (LYH150908)

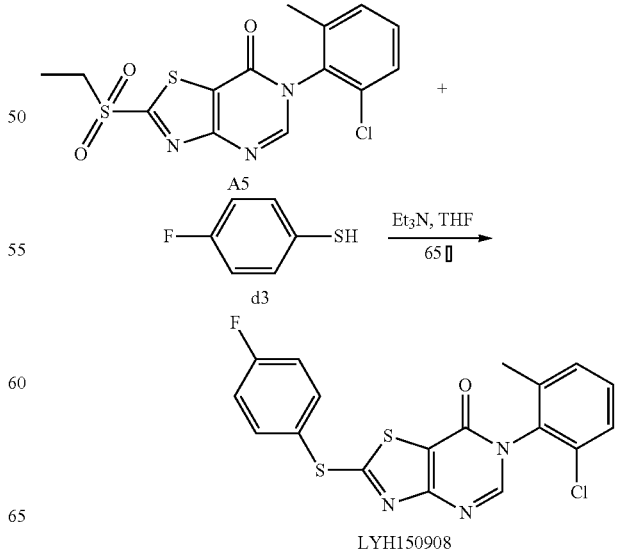

LYH150908

The title compound was prepared following the general procedure of LYH151120. LYH150908 was obtained as a white solid. Yield: 74.4%.

$^1$H-NMR (400 MHz, CDCl$_3$) δ 7.95 (s, 1H), 7.77 (dd, J=8.8, 5.1 Hz, 2H), 7.43 (d, J=8.0 Hz, 1H), 7.38 (t, J=7.8 Hz, 1H), 7.33-7.22 (m, 3H), 2.18 (s, 3H). $^{13}$C-NMR (101 MHz, CDCl$_3$) δ 180.11, 166.82, 166.00, 163.48, 154.99, 149.46, 138.42, 138.29, 138.20, 133.29, 132.70, 130.96, 129.68, 128.12, 123.57, 123.54, 118.06, 118.00, 117.84, 77.40, 77.08, 76.76, 18.22.

Example 68: Preparation of 6-(2-Chloro-6-methyl-phenyl)-2-((4-methoxyphenyl)thio)thiazolo[4,5-d]pyrimidin-7(6H)-one (LYH150909)

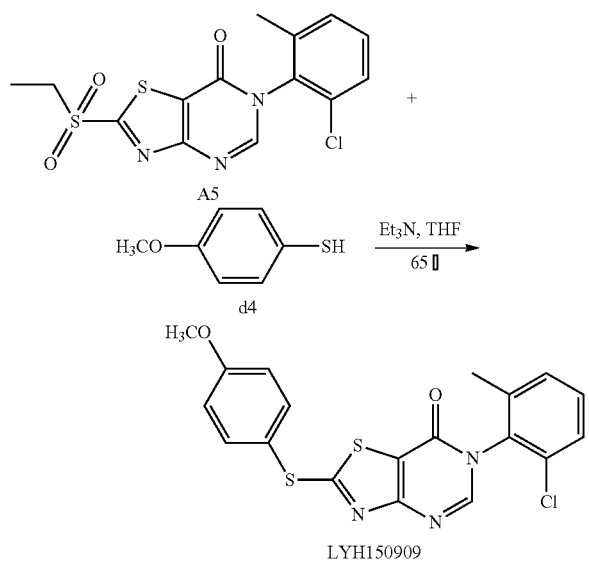

The title compound was prepared following the general procedure of LYH151120. LYH150909 was obtained as a white solid. Yield: 65.6%.

$^1$H-NMR (400 MHz, CDCl$_3$) δ 7.93 (s, 1H), 7.69-7.63 (m, 2H), 7.45-7.39 (m, 1H), 7.35 (t, J=7.8 Hz, 1H), 7.29 (dd, J=5.2, 2.3 Hz, 1H), 7.09-7.01 (m, 2H), 3.89 (s, 3H), 2.17 (s, 3H). $^{13}$C-NMR (101 MHz, CDCl$_3$) δ 182.50, 166.97, 162.33, 155.02, 149.31, 138.45, 137.70, 133.38, 132.70, 130.90, 129.66, 128.08, 118.71, 117.84, 116.16, 77.46, 77.14, 76.82, 55.60, 18.23.

Example 69: Activity Assay

The experimental process was as follows:

(1) *Xenopus* oocytes were injected with cRNA encoding α7 nAChR in order to express α7 nAChR on the cell membrane successfully;

(2) 100 μM ACh alone was added, and the α7 nAChR characteristic current caused by it was recorded as a control;

(3) ACh was washed away;

(4) 10 μM Compound alone was added, if the compound did not induce α7 nAChR characteristic current, it was thought that it did not bind to the agonist site, and the next step could be carried out;

(5) The oocytes were incubated for 1 min with 10 μM compound, then 10 M compound and 100 μM ACh were added simultaneously and the current induced by ACh was recorded at this time;

(6) The differences between the two currents in terms of peak intensity and duration were compared, with the ratio of peak intensity of the two currents representing the adjustment effect (Enhance Rate), in order to determine whether the compound had PAM activity, if the activity was good, then the subsequent test was carried out;

(7) Concentration gradient was set and the effects of compounds at different concentrations on the α7 nAChR characteristic current induced by 100 μM ACh were evaluated. Several determinations were carried out at the same concentration, and the results were presented in the form of "mean±standard deviation";

(8) The EC$_{50}$ (median maximum effect concentration) values and Max mod (the current amplitude caused by the maximal degree of adjustable endogenous agonist acetylcholine) values of the compounds and other activity data were obtained by Hill equation $I_{normalized}=E_{max}/(1+(EC_{50}/C)nH)$. The experimental results are listed in Table 1.

TABLE 1

| Nos. | Stucture | Max Mod (%, at 10 μM) | EC$_{50}$ (μM) |
|---|---|---|---|
| LD286 | | 110 | 100 |
| LD486 | | 320 | 3.20 |

TABLE 1-continued

| Nos. | Stucture | Max Mod (%, at 10 μM) | EC$_{50}$ (μM) |
|---|---|---|---|
| LD293 | | 110 | 100 |
| LD252 | | 110 | 100 |
| LD496 | | 110 | 100 |
| LD493 | | 110 | 100 |
| JWX-A0728 | | 110 | 100 |
| JWX-A0824 | | 300 | 10 |
| JWX-A0828 | | 110 | 100 |

TABLE 1-continued

| Nos. | Stucture | Max Mod (%, at 10 μM) | EC$_{50}$ (μM) |
|---|---|---|---|
| JWX-A0903 | | 110 | 100 |
| JWX-A0912 | | 200 | 10 |
| JWX-A0918 | | 110 | 100 |
| JWX-A1012 | | 110 | 100 |
| JWX-A3N | | 110 | 100 |
| JWX-A1022 | | 110 | 100 |
| JWX-A1029 | | 1920 | 7.47 |

TABLE 1-continued

| Nos. | Stucture | Max Mod (%, at 10 μM) | EC$_{50}$ (μM) |
|---|---|---|---|
| JWX-A1030 | | 200 | 10 |
| JWX-A1104 | | 200 | 10 |
| JWX-A1105 | | 150 | 10 |
| JWX-A1106 | | 150 | 10 |
| JWX-A1113 | | 200 | 10 |
| JWX-A1116 | | 300 | 10 |
| JWX-A1119 | | 250 | 10 |

TABLE 1-continued

| Nos. | Structure | Max Mod (%, at 10 μM) | EC$_{50}$ (μM) |
|---|---|---|---|
| JWX-A1114 | | 150 | 10 |
| JWX-A1211 | | 1540 | 8.39 |
| JWX-A1214 | | 450 | 7.65 |
| JWX-A1218 | | 250 | 10 |
| JWX-A1223 | | 1860 | 1.26 |
| JWX-A1228 | | 110 | 100 |
| JWX-A1229 | | 110 | 100 |
| JWX-A0108 | | 2370 | 3.39 |

TABLE 1-continued

| Nos. | Stucture | Max Mod (%, at 10 μM) | EC$_{50}$ (μM) |
|---|---|---|---|
| JWX-A0121 | | 200 | 10 |
| JWX-A0310 | | 450 | 10 |
| JWX-A0315 | | 650 | 6.99 |
| JWX-A0322 | | 600 | 3.15 |
| JWX-A0414 | | 150 | 10 |
| JWX-A0415 | | 680 | 10 |
| JWX-C1200 | | 110 | 100 |
| LYH150309-2F | | 620 | 4.18 |

TABLE 1-continued

| Nos. | Structure | Max Mod (%, at 10 μM) | EC$_{50}$ (μM) |
|---|---|---|---|
| LYH150310-3F | | 500 | 10 |
| LYH150312-4F | | 670 | 2.87 |
| LYH150318-4Me | | 300 | 10 |
| LYH150324-3Me | | 230 | 10 |
| LYH150325-2Me | | 370 | 10 |
| LYH150326-4OCH3 | | 300 | 10 |
| LYH150409-4CF3 | | 140 | 10 |
| JWX-A0602 | | 300 | 10 |

TABLE 1-continued

| Nos. | Structure | Max Mod (%, at 10 μM) | EC$_{50}$ (μM) |
|---|---|---|---|
| JWX-A0611 | | 200 | 10 |
| JWX-A-C0901 | | 200 | 10 |
| JWX-A-C0907 | | 150 | 10 |
| JWX-A-C0915 | | 300 | 10 |
| JWX-A-C1017 | | 1100 | 5.02 |
| JWX-A-C0104 | | 500 | 10 |
| JWX-A0312 | | 630 | 10 |

TABLE 1-continued

| Nos. | Stucture | Max Mod (%, at 10 μM) | EC$_{50}$ (μM) |
|---|---|---|---|
| JWX-A0617 | | 150 | 10 |
| JWX-A-C1020 | | 350 | 10 |
| JWX-A-C1122 | | 1000 | 9.80 |
| JWX-A-C1128 | | 200 | 10 |
| JWX-A-C1205 | | 980 | 10.76 |
| JWX-A-C1026 | | 300 | 10 |
| JWX-A-C0831 | | 380 | 10 |
| JWX-A-C0106 | | 200 | 10 |

TABLE 1-continued

| Nos. | Structure | Max Mod (%, at 10 μM) | EC$_{50}$ (μM) |
|---|---|---|---|
| JWX-A-C0111 | | 110 | 100 |
| JWX-A-C0229 | | 110 | 100 |
| LYH151120 | | 380 | 10 |
| LYH151215 | | 1100 | 10 |
| LYH150908 | | 200 | 10 |
| LYH150909 | | 110 | 100 |

From the experimental results in the above table, it can be seen that the compounds of the present application have a certain α7 nAChR positive allosteric activity.

Example 70: Examples of Efficacy (LD486)

1. LD486 does not affect the binding of endogenous ligand to radioligand [$^3$H]-Methyllycaconitine (US Radiolabeled Chemicals) ([$^3$H]-MLA).

Using the radioisotope ligand binding assay (Wallace, T. L., Callahan, P. M., Tehim, A., Bertrand, D., Tombaugh, G., Wang, S., Xie, W., Rowe, W. B., Ong, V., Graham, E., Terry, A. V., Jr., Rodefer, J. S., Herbert, B., Murray, M., Porter, R., Santarelli, L., Lowe, D. A., The Journal of pharmacology and experimental therapeutics. 2011, 336, 242-253), the rate curve of radioligand [$^3$H]-Methyllycaconitine bound to rat brain cell membrane was replaced in the case of increasing the concentration of endogenous ligand antagonist PNU-282987 (Sigma, US) or LD486. The results are shown in FIG. 1. It can be seen from FIG. 1 that the binding amount of [$^3$H]-MLA is gradually decreased with the increase of concentration of PNU-282987, with the Ki value being 34.1±4.3 nM. For compound LD486, when the concentration was increased to 10 μM, the combination of [$^3$H]-MLA and α7 nAChR in hippocampus of rats was not reduced, indicating that binding site of LD486 and α7 nAChR is not considered to be the current binding site of agonist at the α7 nAChR.

2. Using the double electrode voltage clamp test (Prickaerts, J., van Goethem, N. P., Chesworth, R., Shapiro, G., Boess, F. G., Methfessel, C., Reneerkens, O. A., Flood, D. G., Hilt, D., Gawryl, M., Bertrand, S., Bertrand, D., Konig, G., Neuropharmacology 2012, 62, 1099-1110), it was found that LD486 was more active as a positive allosteric modulator of α7 nicotinic acetylcholine receptor.

Figure 2:
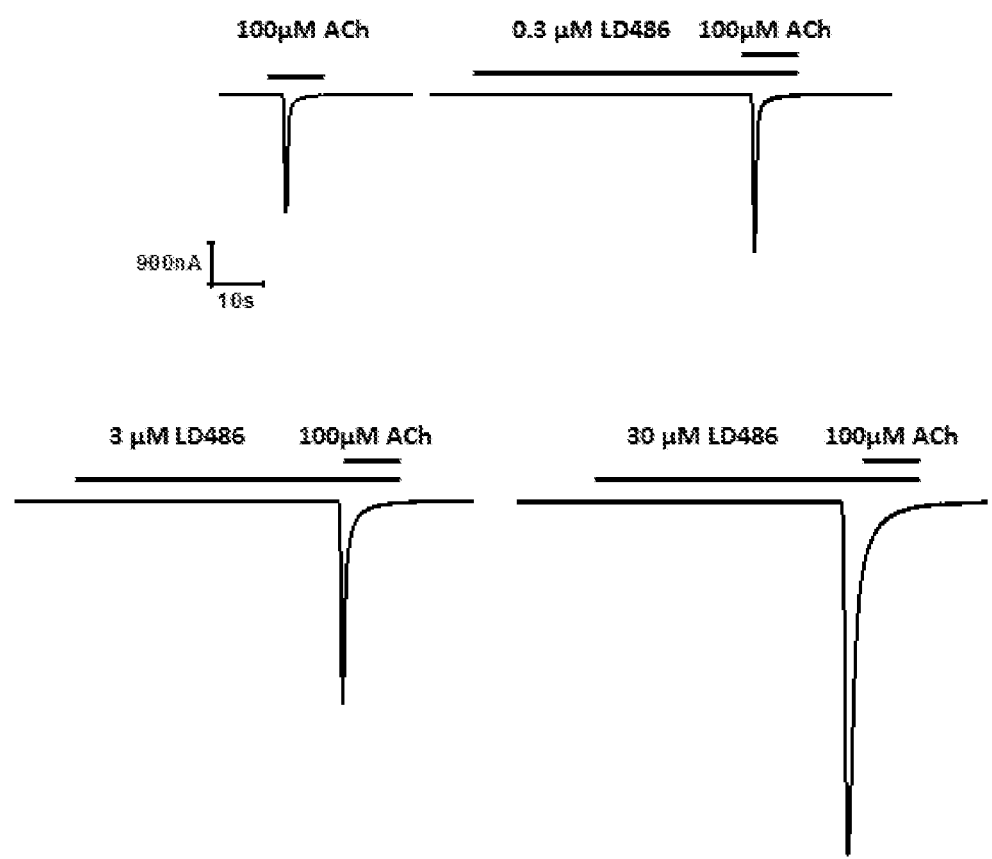
FIG. 2 shows the response intensity of *Xenopus* oocytes patch clamp of 100 μM ACh without LD486 and with LD486 of different concentrations.

FIG. 2 shows the response intensity of *Xenopus* oocytes patch clamp of 100 μM Ach without LD486 and with LD486 of different concentrations. It can be seen from FIG. 2 that with the current induced by addition of 100 μM ACh alone as a control, the addition of LD486 (0.1-10 μM) at different concentrations does not induce the α7 nAChR characteristic current. But after incubation with LD486 for 1 min, and the same concentration of LD486 and 100 μM ACh were added at the same time, it was observed that the current amplitude induced by 100 μM ACh was significantly increased compared with the control group.

Figure 3:
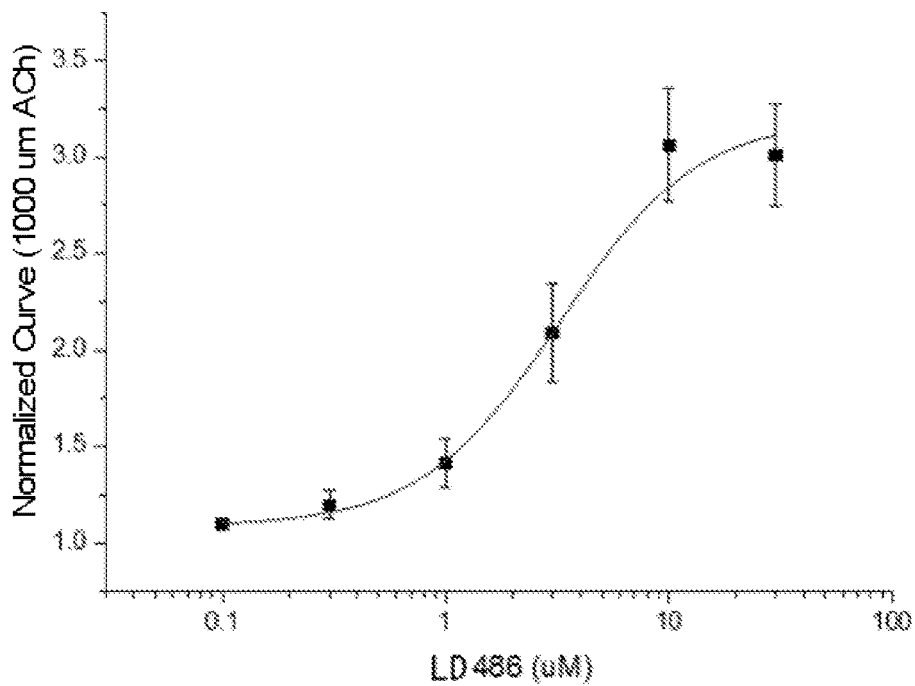
FIG. 3 is the concentration response curve of LD486.

The concentration response curve of LD486 is shown in FIG. 3. The amplitude of the peak current is only normalized by the amplitude produced by 100 μM ACh and different concentrations of LD486. $EC_{50}$=3.2 μM, $E_{max}$=320%, nHill=1.4 (all data measurements are repeated for 6 times). It can be seen from FIG. 3 that the Hill equation is used to fit the dose-response curve and calculate the kinetic parameters. The results show that the maximal degree of adjustable endogenous agonist ACh current amplitude of LD486 is about 3.2 times, with the $EC_{50}$ value being 3.2±0.3 μM, and the Hill coefficient being 1.4±0.2 (n=6).

3. Using a two-electrode voltage clamp experiment (Prickaerts, J., van Goethem, N P, Chesworth, R., Shapiro, G., Boess, F G, Methfessel, C., Reneerkens, O A, Flood, D G, Hilt, D., Gawryl, M., Bertrand, S., Bertrand, D., Konig, G., Neuropharmacology 2012, 62, 1099-1110), it was found that LD486 did not increase the current intensity of α4β2 and α3β4 receptors in *Xenopus* oocytes.

Figure 4:
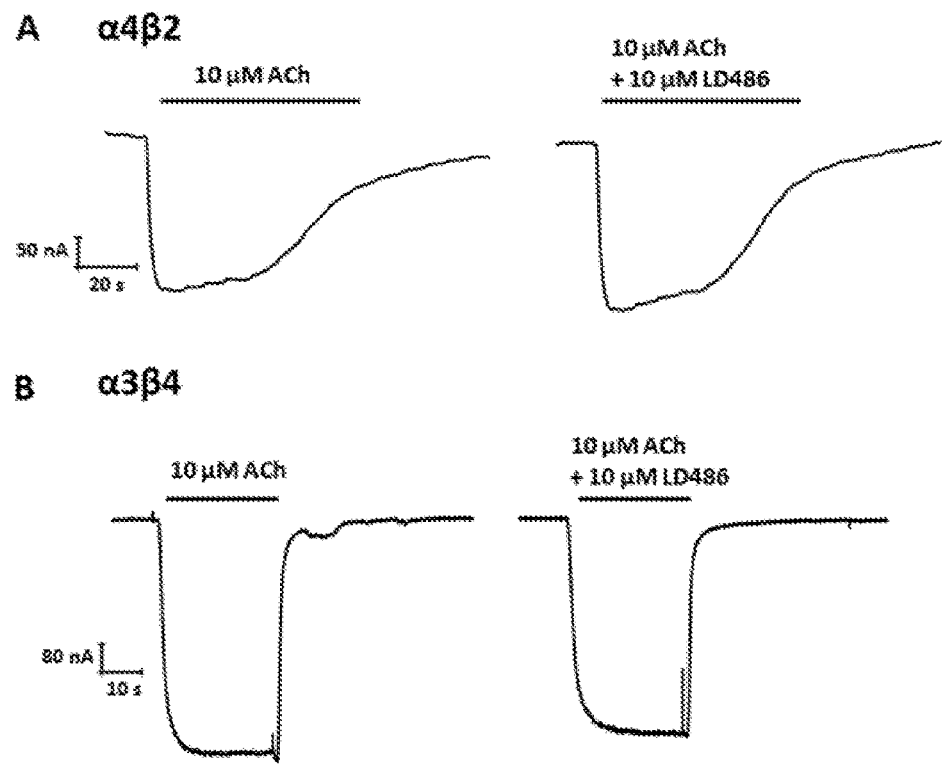
FIG. 4: the left panel is the response intensity curve of α4β2 and α3β4 in *Xenopus* oocytes stimulated by 30 μM ACh. The right panel is the response intensity curve of α4β2 and α3β4 in *Xenopus* oocytes stimulated by 30 μM ACh and 10 μM LD486.

FIGS. 4A and B show the response intensity curves of *Xenopus* oocytes stimulated by only 10 M Ach to α4β2 and α3β4 in the left panel, respectively.

FIGS. 4A and B show the response intensity curves of *Xenopus* oocytes stimulated by 10 μM ACh and 10 M LD486 to α4β2 and α3β4 in the right panel, respectively. *Xenopus* oocytes are pre-stimulated with 10 μM LD486 for 60 seconds.

α4β2 is now considered to be a potential therapeutic target for AD, but the object of the present invention is to screen for α7 nAChR targeting compounds to facilitate the study of α7 nAChR in neuropsychiatric disorders; drugs targeted on nAChR are currently found that they have gastrointestinal adverse reactions clinically. Therefore, we hope that LD486 have better specificity to targets within the nAChR family to reduce the adverse reactions of acting on other unrelated targets.

Used as exogenous expression system, *Xenopus* oocytes are injected with different α subunits and β subunits at 1:1 ratio. After 48 h, the expression of the channel was examined, and it was found that the activity of α4β2 and α3β4 receptors was activated by 10 μM ACh respectively, but LD486 had no significant effect on the amplitude of current induced by 10 μM ACh.

4. Using the automatic patch clamp Qplate-16 assay (Schmalhofer, W A, Swensen, A M, Thomas, B S, Felix, J P, Haedo, R J, Solly, K., Kiss, L., Kaczorowski, G J, Garcia, M L, Assay and drug development technologies 2010, 8, 714-726), LD486 was found to have no inhibitory effect on the hERG (human ether-a-go-go related gene) channel expressed on CHO (Chinese hamster ovary cell) cell lines.

In the absence of LD486 or cisapride or in the presence of LD486 or cisapride at different concentrations, drug-related hERG potassium channel inhibition can lead to ventricular delayed repolarization (long QT interval syndrome), which may lead to a current intensity of fatal arrhythmia such as torsades de pointes, and even sudden death. The results showed that LD486 had a slight inhibitory effect on the hERG channel, but it could be used as a lead compound because of its weak inhibitory effect, and its structure was optimized to obtain a compound capable of modulating α7 nAChR more powerfully.

The invention claimed is:

1. A thiazolopyrimidinone compound having a structure represented by Formula (I):

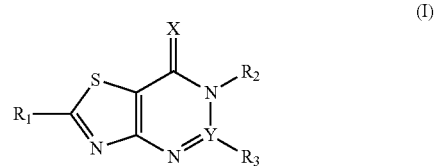

wherein, X=O or S, and Y=C, when Y=C, $R_3$ is selected from the group consisting of H, phenyl, phenyl substituted by one or more of halogen, hydroxyl, carboxyl, C1-C4 alkyl and C1-C4 alkoxy, and five or six membered heterocyclyl;

$R_2$ is selected from the group consisting of C1-C6 alkoxy, C1-C6 alkylthio, C1-C6 alkylamino, phenyl, phenyl substituted by one or more of halogen, hydroxyl, carboxyl, C1-C4 alkyl and C1-C4 alkoxy, benzyl, benzyl substituted by one or more of halogen, hydroxyl, carboxyl, C1-C4 alkyl and C1-C4 alkoxy, five or six membered heterocyclyl, and five or six membered heterocyclyl substituted by one or more of halogen, hydroxyl, carboxyl, C1-C4 alkyl and C1-C4 alkoxy;

$R_1$ is selected from the group consisting of C1-C6 alkyl, C1-C6 alkoxy, C1-C6 alkylamino, phenyl, phenyl substituted by one or more of halogen, carboxyl, C1-C4 alkyl and C1-C4 alkoxy, phenylthio, phenylthio substituted by one or more of halogen, carboxyl, C1-C4 alkyl and C1-C4 alkoxy, benzylthio, benzylthio substituted by one or more of halogen, carboxyl, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, and arylcarboxamido substituted by one or more of halogen, C1-C4 alkyl, C1-C4 alkoxy, five or six membered heterocyclyl and five or six membered heterocyclyl substituted by C1-C4 alkyl or hydroxyl.

2. The thiazolopyrimidinone compound according to claim 1, wherein X=O and Y=C, $R_1$ is selected from the group consisting of C1-C6 alkylamino, phenyl, phenyl substituted by one or more of halogen, carboxyl, C1-C4 alkyl and C1-C4 alkoxy, phenylthio, phenylthio substituted by one or more of halogen, carboxyl, C1-C4 alkyl and C1-C4 alkoxy, benzylthio, benzylthio substituted by one or more of halogen, carboxyl, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, arylcarboxamido substituted by one or more of halogen, C1-C4 alkyl, C1-C4 alkoxy, five or six membered heterocyclyl and five or six membered heterocyclyl substituted by C1-C4 alkyl or hydroxyl; $R_2$ is selected from phenyl substituted by one or more of halogen, hydroxyl, carboxyl, C1-C4 alkyl and C1-C4 alkoxy; $R_3$=H.

3. A method for preparing a thiazolopyrimidinone compound according to claim 1 or 2, comprising the steps of:

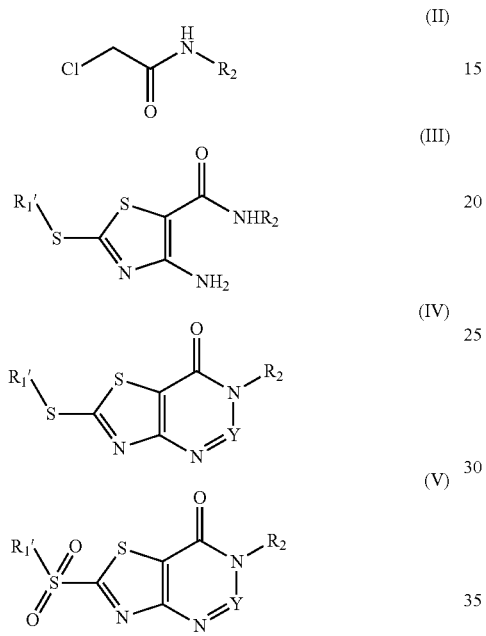

(1) reacting chloroacetyl chloride with $R_2$—$NH_2$, to give a compound II;
(2) reacting compound II with dipotassium cyanodithiomidocarbonate as well as iodomethane, iodoethane, halogenated C1-C6 alkyl, halogenated C1-C6 alkylamine, phenyl substituted by one or more of halogen, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, or benzyl halide substituted by one or more of halogen, carboxyl, C1-C4 alkyl and C1-C4 alkoxy, to give a compound III;
(3) reacting compound III with formic acid or $NaNO_2$, to give a compound IV, which is a ring closure product;
when $R_1$ in Formula (I) is benzylthio substituted by one or more of halogen, carboxyl, C1-C4 alkyl and C1-C4 alkoxy, compound IV is represented by the Formula (I); or
when $R_1$ in Formula (I) is C1-C6 alkylamino, phenyl, phenyl substituted by one or more of halogen, carboxyl, C1-C4 alkyl and C1-C4 alkoxy, phenylthio, phenylthio substituted by one or more of halogen, carboxyl, C1-C4 alkyl and C1-C4 alkoxy, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, arylcarboxamido substituted by one or more of halogen, C1-C4 alkyl, C1-C4 alkoxy, five or six membered heterocyclyl and five or six membered heterocyclyl substituted by C1-C4 alkyl or hydroxyl, compound IV is subjected to step (4), or compound IV is transformed to a compound V under the action of an oxidizing agent and then subjected to step (4);
(4) reacting compound IV or V with C1-C6 alkylamine, phenylboronic acid, phenylboronic acid substituted by one or more of halogen, carboxyl, C1-C4 alkyl and C1-C4 alkoxy, thiophenol, thiophenol substituted by one or more of halogen, carboxyl, C1-C4 alkyl and C1-C4 alkoxy, arylamine, arylamine substituted by one or more of halogen, C1-C4 alkyl, C1-C4 alkoxy, five or six membered heterocyclyl and five or six membered heterocyclyl substituted by C1-C4 alkyl or hydroxyl, arylcarboxamide, arylcarboxamide substituted by one or more of halogen, C1-C4 alkyl, C1-C4 alkoxy, five or six membered heterocyclyl and five or six membered heterocyclyl substituted by C1-C4 alkyl or hydroxyl, to give a compound represented by Formula (I);
wherein, $R_1'$ in compound III, IV and V is selected from the group consisting of C1-C6 alkyl, phenyl, phenyl substituted by one or more of halogen, carboxyl, C1-C4 alkyl and C1-C4 alkoxy, benzyl, benzyl substituted by one or more of halogen, carboxyl, C1-C4 alkyl and C1-C4 alkoxy, five or six membered heterocyclyl and five or six membered heterocyclyl substituted by one or more of halogen, hydroxyl, carboxyl, C1-C4 alkyl and C1-C4 alkoxy.

4. The method according to claim 3, comprising any one of the following four synthetic routes:
Synthetic Route 1:

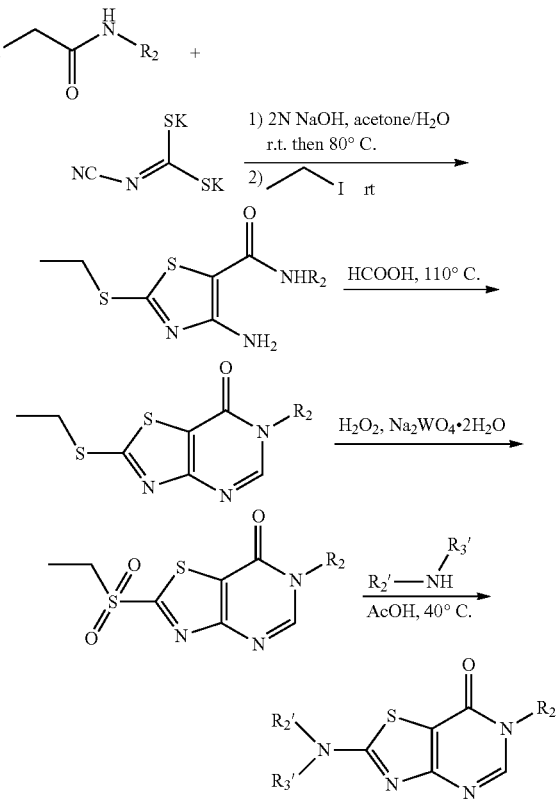

wherein, the substituent

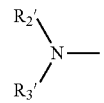

represents C1-C6 alkylamino, arylamino, arylamino substituted by one or more of halogen, C1-C4 alkyl, C1-C4 alkoxy, five or six membered heterocyclyl and five or six membered heterocyclyl substituted by C1-C4 alkyl or hydroxyl, arylcarboxamido, arylcarboxamido substituted by one or more of halogen, C1-C4 alkyl, C1-C4 alkoxy, five or six membered heterocyclyl and five or six membered heterocyclyl substituted by C1-C4 alkyl or hydroxyl, or —NH—R₂;

Synthetic Route 2:

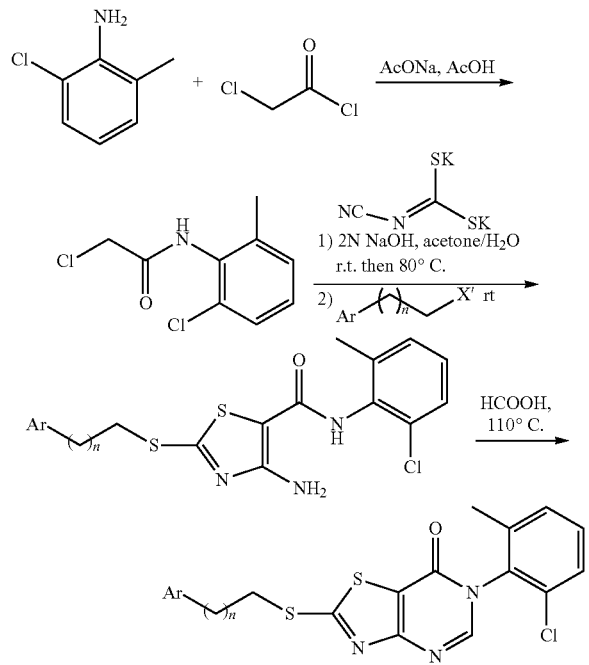

n = 0~5

Synthetic Route 3:

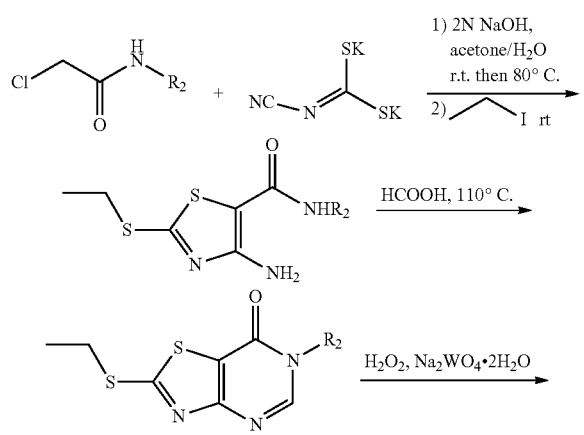

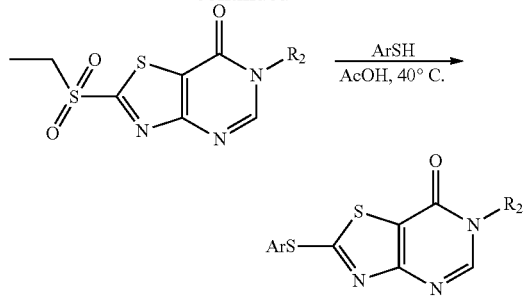

Synthetic Route 4:

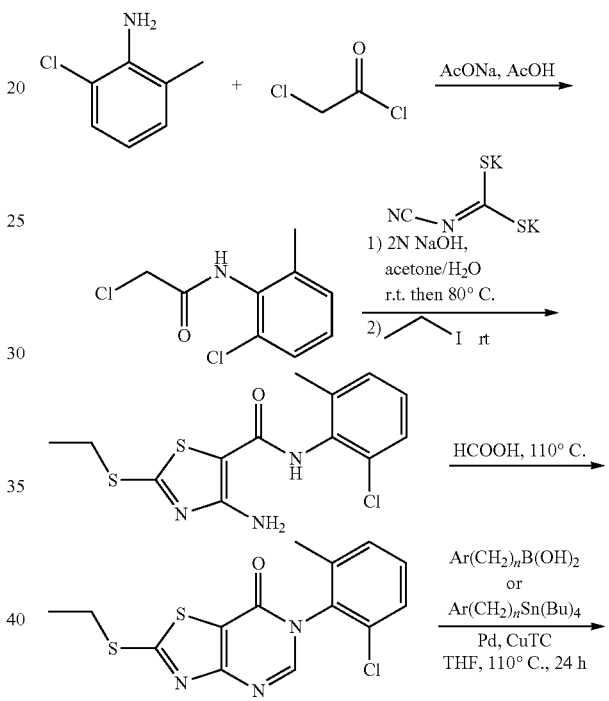

n = 0-3 wherein, in the synthetic routes 2, 3 and 4, Ar represents phenyl or phenyl substituted by F, methyl, methoxyl or trifluoromethyl; and wherein, in the synthetic route 2, X' represents Br or Cl.

5. A method for treating Alzheimer's disease, comprising administering to a subject in need thereof a thiazolopyrimidinone compound according to claim 1.

* * * * *